United States Patent
Yerkes et al.

(10) Patent No.: US 9,644,469 B2
(45) Date of Patent: *May 9, 2017

(54) HERBICIDAL COMPOSITIONS COMPRISING 4-AMINO-3-CHLORO-5-FLUORO-6-(4-CHLORO-2-FLUORO-3-METHOXYPHENYL) PYRIDINE-2-CARBOXYLIC ACID OR A DERIVATIVE THEREOF AND VLCFA AND LIPID SYNTHESIS INHIBITING HERBICIDES

(71) Applicant: Dow Agrosciences LLC, Indianapolis, IN (US)

(72) Inventors: Carla N. Yerkes, Crawfordsville, IN (US); Richard K. Mann, Franklin, IN (US); Ikuo Shiraishi, Tokyo (JP); Shingo Yanagiyama, Tokyo (JP); Norbert M. Satchivi, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 367 days.

This patent is subject to a terminal disclaimer.

(21) Appl. No.: 13/840,306

(22) Filed: Mar. 15, 2013

(65) Prior Publication Data

US 2013/0310256 A1    Nov. 21, 2013

Related U.S. Application Data

(60) Provisional application No. 61/675,105, filed on Jul. 24, 2012.

(51) Int. Cl.
| | |
|---|---|
| *A01N 43/40* | (2006.01) |
| *A01N 37/20* | (2006.01) |
| *A01N 37/22* | (2006.01) |
| *A01N 37/26* | (2006.01) |
| *A01N 43/10* | (2006.01) |
| *A01N 43/12* | (2006.01) |
| *A01N 43/78* | (2006.01) |
| *A01N 43/80* | (2006.01) |

(Continued)

(52) U.S. Cl.
CPC .............. *E21B 44/00* (2013.01); *A01N 37/20* (2013.01); *A01N 37/26* (2013.01); *A01N 43/10* (2013.01); *A01N 43/12* (2013.01); *A01N 43/20* (2013.01); *A01N 43/40* (2013.01); *A01N 43/653* (2013.01); *A01N 43/713* (2013.01); *A01N 43/78* (2013.01); *A01N 43/82* (2013.01); *A01N 57/14* (2013.01); *E21B 10/34* (2013.01)

(58) Field of Classification Search
CPC ........ A01N 37/20; A01N 37/26; A01N 43/10; A01N 43/12; A01N 43/20; A01N 43/40; A01N 43/653; A01N 43/713; A01N 43/78; A01N 43/82; A01N 57/14; E12B 44/00; E21B 10/34

See application file for complete search history.

(56) References Cited

U.S. PATENT DOCUMENTS

| | | | |
|---|---|---|---|
| 7,314,849 | B2 | 1/2008 | Balko et al. |
| 7,622,641 | B2 | 11/2009 | McCutchen et al. |

(Continued)

FOREIGN PATENT DOCUMENTS

| | | | |
|---|---|---|---|
| WO | WO2007/082098 | * | 7/2007 |
| WO | WO2007/082098 A2 | * | 7/2007 |

(Continued)

OTHER PUBLICATIONS

The article of Synthesis of Esters: Esterification Reactions, obtained via google.com.*

(Continued)

*Primary Examiner* — John Pak
(74) *Attorney, Agent, or Firm* — Michael R. Asam; Faegre Baker Daniels LLP

(57) ABSTRACT

A synergistic herbicidal composition containing (a) a compound of formula (I):

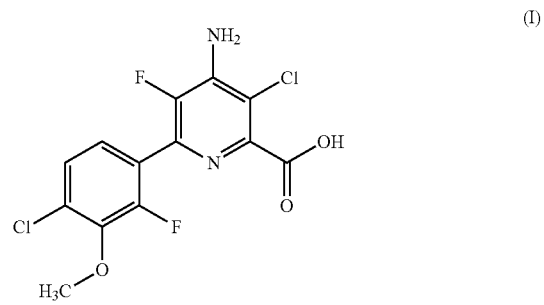

(I)

or an agriculturally acceptable salt or ester thereof and (b) VLCFA and fatty acid/lipid synthesis inhibiting herbicides, including but not limited to, acetochlor, alachlor, anilofos, benfuresate, cafenstrole, dimethenamid-P, fentrazamide, indanofan, flufenacet, mefenacet, s-metolachlor, molinate, pethoxamid, pretilachlor, prosulfocarb, pyroxasulfone, thenylchlor and thiobencarb, or a salt or ester thereof, provide synergistic weed control of undesirable vegetation in direct-seeded, water-seeded and transplanted rice, cereals, wheat, barley, oats, rye, sorghum, corn or maize, sugarcane, sunflower, oilseed rape, canola, sugar beet, soybean, cotton, pineapple, pastures, grasslands, rangelands, fallowland, turf, tree and vine orchards, aquatics, plantation crops, vegetables, industrial vegetation management (IVM) or rights-of-way (ROW).

20 Claims, No Drawings

(51) Int. Cl.
*A01N 43/82* (2006.01)
*A01N 47/12* (2006.01)
*A01N 47/16* (2006.01)
*A01N 47/38* (2006.01)
*E21B 44/00* (2006.01)
*A01N 43/20* (2006.01)
*A01N 43/653* (2006.01)
*A01N 43/713* (2006.01)
*A01N 57/14* (2006.01)
*E21B 10/34* (2006.01)

(56) References Cited

U.S. PATENT DOCUMENTS

| | | | |
|---|---|---|---|
| 2009/0062121 A1* | 3/2009 | Satchivi | A01N 43/40 504/105 |
| 2010/0130361 A1 | 5/2010 | Yerkes et al. | |
| 2010/0137137 A1 | 6/2010 | Rosinger et al. | |
| 2011/0082162 A1 | 4/2011 | Lorsbach et al. | |
| 2011/0207607 A1 | 8/2011 | Satchivi et al. | |
| 2012/0115727 A1 | 5/2012 | Satchivi et al. | |
| 2012/0190551 A1 | 7/2012 | Yerkes et al. | |
| 2013/0109569 A1 | 5/2013 | Dave et al. | |
| 2014/0031210 A1 | 1/2014 | Yerkes et al. | |
| 2014/0031211 A1 | 1/2014 | Yerkes et al. | |
| 2014/0031212 A1 | 1/2014 | Yerkes et al. | |
| 2014/0031213 A1 | 1/2014 | Yerkes et al. | |
| 2014/0031214 A1 | 1/2014 | Yerkes et al. | |
| 2014/0031215 A1 | 1/2014 | Yerkes et al. | |
| 2014/0031216 A1 | 1/2014 | Yerkes et al. | |
| 2014/0031217 A1 | 1/2014 | Yerkes et al. | |
| 2014/0031218 A1 | 1/2014 | Mann et al. | |
| 2014/0031219 A1 | 1/2014 | Yerkes et al. | |
| 2014/0031220 A1 | 1/2014 | Yerkes et al. | |
| 2014/0031221 A1 | 1/2014 | Yerkes et al. | |
| 2014/0031222 A1 | 1/2014 | Yerkes et al. | |
| 2014/0031227 A1 | 1/2014 | Yerkes et al. | |
| 2014/0031228 A1 | 1/2014 | Mann et al. | |
| 2014/0031229 A1 | 1/2014 | Mann et al. | |

FOREIGN PATENT DOCUMENTS

| | | |
|---|---|---|
| WO | 2009029518 | 3/2009 |
| WO | 2014018358 | 1/2014 |

OTHER PUBLICATIONS

The article of Steglich Esterification with DCC, obtained online via google.com.*
"Clopyralid", Compendium of Pesticide Common Names, available at http://www.alanwood.net/pesticides/clopyralid.html, (downloaded Jul. 28, 2016).
"Fluroxypyr", Compendium of Pesticide Common Names, available at http://www.alanwood.net/pesticides/fluroxypyr.html, (downloaded Jul. 28, 2016).
Thomas, S., Written Opinion of the International Search Authority for PCT/US2013/051302, Dec. 6, 2013, pp. 1-5, ISA/US.
Thomas, S., International Search Report for PCT/US2013/051302, Dec. 6, 2013, pp. 1-4, ISA/US.
Pryor, A.N., Non-Final Office Action in U.S. Appl. No. 13/840,488 issued Dec. 31, 2013, pp. 1-6, USPTO.
Pryor, A.N., Non-Final Office Action in U.S. Appl. No. 13/840,346 issued Jan. 2, 2014, pp. 1-5, USPTO.
Pryor, A.N., Non-Final Office Action in U.S. Appl. No. 13/840,303 issued Jan. 3, 2014, pp. 1-5, USPTO.
Pryor, A.N., Non-Final Office Action in U.S. Appl. No. 13/833,372 issued Jan. 2, 2014, pp. 1-5, USPTO.
Pryor, A.N., Non-Final Office Action in U.S. Appl. No. 13/836,653 issued Nov. 7, 2013, pp. 1-7, USPTO.
Pryor, A.N., Non-Final Office Action in U.S. Appl. No. 13/839,043 issued Nov. 6, 2013, pp. 1-7, USPTO.
Pryor, A.N., Non-Final Office Action in U.S. Appl. No. 13/837,990 issued Nov. 6, 2011, pp. 1-7, USPTO.
Pryor, A.N., Non-Final Office Action in U.S. Appl. No. 13/840,236 issued Jan. 3, 2014, pp. 1-6, USPTO.
Pryor, A.N., Non-Final Office Action in U.S. Appl. No. 13/840,419 issued Dec. 31, 2013, pp. 1-5, USPTO.
Pryor, A.N., Notice of Allowance and Fee(s) Due for U.S. Appl. No. 13/832,978, Apr. 9, 2014, pp. 1-13, USPTO.
Pryor, A.N., Notice of Allowance and Fee(s) Due for U.S. Appl. No. 13/833,315, May 12, 2014, pp. 1-8, USPTO.
Pryor, A.N., Notice of Allowance and Fee(s) Due for U.S. Appl. No. 13/833,315, Mar. 20, 2014, pp. 1-11, USPTO.
Pryor, A.N., Notice of Allowance and Fee(s) Due for U.S. Appl. No. 13/833,362, May 29, 2014, pp. 1-8, USPTO.
Pryor, A.N., Notice of Allowance and Fee(s) Due for U.S. Appl. No. 13/833,372, May 14, 2014, pp. 1-8, USPTO.
Pryor, A.N., Notice of Allowance and Fee(s) Due for U.S. Appl. No. 13/833,659, Mar. 17, 2014, pp. 1-12, USPTO.
Pryor, A.N., Notice of Allowance and Fee(s) Due for U.S. Appl. No. 13/833,923, May 2, 2014, pp. 1-9, USPTO.
Pryor, A.N., Notice of Allowance and Fee(s) Due for U.S. Appl. No. 13/833,965, Apr. 1, 2014, pp. 1-8, USPTO.
Pryor, A.N., Notice of Allowance and Fee(s) Due for U.S. Appl. No. 13/834,326, May 13, 2014, pp. 1-4, USPTO.
Pryor, A.N., Notice of Allowance and Fee(s) Due for U.S. Appl. No. 13/834,326, Apr. 2, 2014, pp. 1-9, USPTO.
Pryor, A.N., Notice of Allowance and Fee(s) Due for U.S. Appl. No. 13/834,706, Mar. 12, 2014, pp. 1-13, USPTO.
Pryor, A.N., Notice of Allowance and Fee(s) Due for U.S. Appl. No. 13/836,653, Apr. 2, 2014, pp. 1-8, USPTO.
Pryor, A.N., Notice of Allowance and Fee(s) Due for U.S. Appl. No. 13/837,990, Apr. 1, 2014, pp. 1-8, USPTO.
Pryor, A.N., Notice of Allowance and Fee(s) Due for U.S. Appl. No. 13/839,043, May 27, 2014, pp. 1-5, USPTO.
Pryor, A.N., Notice of Allowance and Fee(s) Due for U.S. Appl. No. 13/839,043, Mar. 24, 2014, pp. 1-8, USPTO.
Pryor, A.N., Notice of Allowance and Fee(s) Due for U.S. Appl. No. 13/840,236, Apr. 25, 2014, pp. 1-8, USPTO.
Pryor, A.N., Notice of Allowance and Fee(s) Due for U.S. Appl. No. 13/840,303, Apr. 25, 2014, pp. 1-8, USPTO.
Pryor, A.N., Notice of Allowance and Fee(s) Due for U.S. Appl. No. 13/840,346, Jun. 4, 2014, pp. 1-8, USPTO.
Pryor, A.N., Notice of Allowance and Fee(s) Due for U.S. Appl. No. 13/840,419, May 5, 2014, pp. 1-8, USPTO.
Pryor, A.N., Notice of Allowance and Fee(s) Due for U.S. Appl. No. 13/840,488, May 2, 2014, pp. 1-8, USPTO.

* cited by examiner

HERBICIDAL COMPOSITIONS COMPRISING 4-AMINO-3-CHLORO-5-FLUORO-6-(4-CHLORO-2-FLUORO-3-METHOXYPHENYL) PYRIDINE-2-CARBOXYLIC ACID OR A DERIVATIVE THEREOF AND VLCFA AND LIPID SYNTHESIS INHIBITING HERBICIDES

PRIORITY CLAIM

This application claims the benefit of U.S. provisional patent application No. 61/675,105 filed on Jul. 24, 2012, this provisional application is incorporated herein by reference in its entirety.

FIELD

Provided herein are herbicidal compositions comprising (a) 4-amino-3-chloro-5-fluoro-6-(4-chloro-2-fluoro-3-methoxyphenyl)pyridine-2-carboxylic acid or an agriculturally acceptable ester or salt thereof and (b) very long chain fatty acid (VLCFA) synthesis-inhibiting herbicides and fatty acid/lipid synthesis inhibiting herbicides.

Provided herein are also methods of controlling undesirable vegetation comprising applying (a) 4-amino-3-chloro-5-fluoro-6-(4-chloro-2-fluoro-3-methoxyphenyl)pyridine-2-carboxylic acid or an agriculturally acceptable ester or salt thereof and (b) VLCFA and fatty acid/lipid synthesis inhibiting herbicides.

BACKGROUND

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use. However, there remains a need for compositions and methods that are effective in controlling undesirable vegetation.

SUMMARY

Several embodiments are recited below. In the embodiments, the ratio of compound (a) to compound (b) can be expressed in terms of weight to weight (g to g), gae/ha to gae/ha, or gae/ha to gai/ha.

A first embodiment of the invention provided herein includes herbicidal compositions comprising an herbicidally effective amount of (a) a compound of the formula (I)

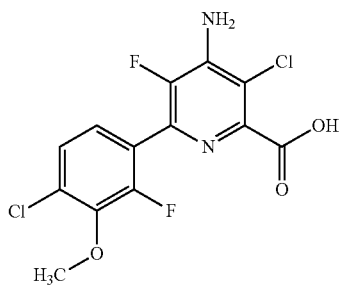

(I)

or an agriculturally acceptable salt or ester thereof and (b) VLCFA and fatty acid/lipid synthesis inhibiting herbicides.

A second embodiment of the invention provided herein includes a method of controlling undesirable vegetation which comprises contacting the vegetation or the locus thereof with or applying to the soil or water to prevent the emergence or growth of vegetation the composition of embodiment 1.

A third embodiment of the invention provided herein includes a method of controlling undesirable vegetation which comprises contacting the vegetation or the locus thereof with or applying to the soil or water to prevent the emergence or growth of vegetation a herbicidally effective amount of (a) a compound of the formula (I)

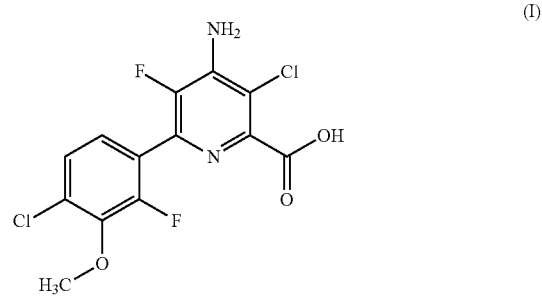 [SMILES: COc1c(Cl)ccc(-c2nc(C(=O)O)c(Cl)c(N)c2F)c1F]

(I)

or an agriculturally acceptable salt or ester thereof and (b) a VLCFA and fatty acid/lipid synthesis inhibiting herbicide.

Provided herein are herbicidal compositions comprising a herbicidally effective amount of (a) a compound of the formula (I)

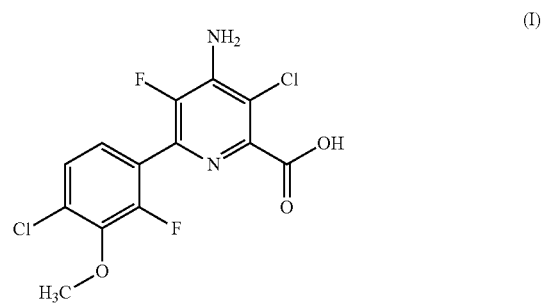 [SMILES: COc1c(Cl)ccc(-c2nc(C(=O)O)c(Cl)c(N)c2F)c1F]

(I)

or an agriculturally acceptable salt or ester of thereof, and (b) VLCFA and fatty acid/lipid synthesis inhibiting herbicides. Exemplary inhibiting herbicides include, but are not limited to, acetochlor, alachlor, anilofos, butachlor, benfuresate, cafenstrole, dimethenamid-P, fentrazamide, indanofan, flufenacet, mefenacet, s-metolachlor, molinate, pethoxamid, pretilachlor, prosulfocarb, pyroxasulfone, thenylchlor and thiobencarb, or acceptable salts and esters thereof. The compositions may also contain an agriculturally acceptable adjuvant or carrier.

Provided herein are also methods of controlling undesirable vegetation comprising applying (a) a compound of formula (I) or an agriculturally acceptable ester or salt thereof and (b) VLCFA and fatty acid/lipid synthesis inhibiting herbicides.

DETAILED DESCRIPTION

Definitions

As used herein, the compound of formula (I) has the following structure:

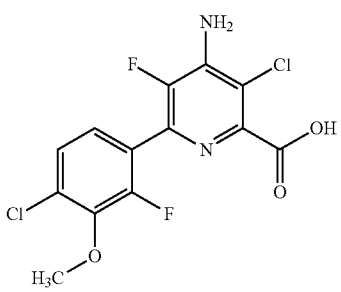

(I)

The compound of formula (I) can be identified by the name 4-amino-3-chloro-6-(4-chloro-2-fluoro-3-methoxyphenyl)-5-fluoropyridine-2-carboxylic acid and has been described in U.S. Pat. No. 7,314,849 (B2), which is incorporated herein by reference in its entirety. Exemplary uses of the compound of the formula (I) include controlling undesirable vegetation, including grass, broadleaf and sedge weeds, in multiple non-crop and cropping situations.

Exemplary VLCFA and fatty acid/lipid synthesis inhibiting herbicides include the chemical classes of acetamides, chloroacetamides, oxyacetamides, tetrazolinones, benzofuranes, thiocarbamates, and phosphorodithioates. Without being limited to any theory, their herbicidal activity is attributed to inhibition of very-long-chain fatty acid (VLCFA, fatty acids, e.g., >C18) synthesis and fatty acid/lipid synthesis. Exemplary VLCFA and fatty acid/lipid synthesis inhibiting herbicides include, but are not limited to acetochlor, alachlor, anilofos, butachlor, benfuresate, cafenstrole, dimethenamid-P, fentrazamide, indanofan, flufenacet, mefenacet, s-metolachlor, molinate, pethoxamid, pretilachlor, prosulfocarb, pyroxasulfone, thenylchlor and thiobencarb, or a salts thereof.

As used herein, acetochlor is 2-chloro-N-(ethoxymethyl)-N-(2-ethyl-6-methylphenyl)acetamide and possesses the following structure:

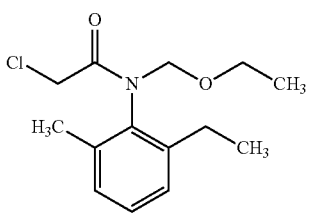 [SMILES: CCOCN(C(=O)CCl)c1c(C)cccc1CC]

Its herbicidal activity is exemplified in Tomlin, C., ed. A World Compendium The Pesticide Manual. 15$^{th}$ ed. Alton: BCPC Publications, 2009 (hereafter "*The Pesticide Manual*, Fifteenth Edition, 2009."). Exemplary uses of acetochlor include its use for pre-emergence or pre-plant control of grasses, certain broadleaf weeds and yellow nutsedge, e.g., in maize, soybeans, peanuts, cotton, potatoes and sugar cane.

As used herein, alachlor is 2-chloro-N-(2,6-diethylphenyl)-N-(methoxymethyl)acetamide and possesses the following structure:

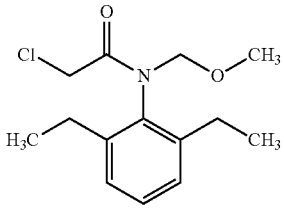 [SMILES: CCc1cccc(CC)c1N(COC)C(=O)CCl]

Its herbicidal activity is exemplified in *The Pesticide Manual*, Fifteenth Edition, 2009. Exemplary uses of alachlor include its use for pre-emergence control of annual grasses and many broadleaf weeds, e.g., in cotton, brassica's, maize, oilseed rape, peanuts, radish, soybeans and sugar cane.

As used herein, anilofos is S-[2-[(4-chlorophenyl)(1-methylethyl)amino]-2-oxoethyl]O,O-dimethyl phosphorodithioate and possesses the following structure:

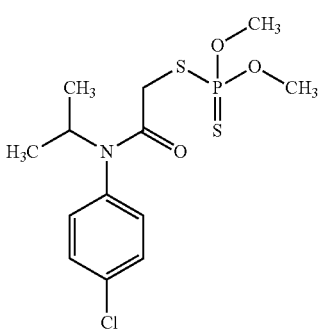 [SMILES: COP(=S)(OC)SCC(=O)N(c1ccc(Cl)cc1)C(C)C]

Its herbicidal activity is described in *Journal of Applied Toxicology* 2007, 27, 255-261. Exemplary uses of anilofos include, e.g., its use for control of annual grassy weeds and sedges, e.g., in transplanted rice.

As used herein, benfuresate is 2,3-dihydro-3,3-dimethyl-5-benzofuranyl ethanesulfonate and possesses the following structure:

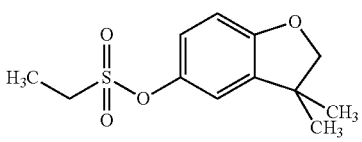

Its herbicidal activity is exemplified in *The Pesticide Manual*, Fifteenth Edition, 2009. Exemplary uses of benfuresate include its use for post-emergence control of grass and broadleaf weeds, e.g., in paddy rice, fruit, beans, maize, sugar cane and perennial crops.

As used herein, butachlor is N-(butoxymethyl)-2-chloro-N-(2,6-diethylphenyl)acetamide and possesses the following structure:

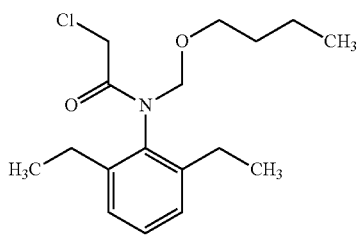 [SMILES: CCCCOCN(C(=O)CCl)c1c(CC)cccc1CC]

Its herbicidal activity is exemplified in *The Pesticide Manual*, Fifteenth Edition, 2009. Exemplary uses of butachlor include its use for pre-emergence control of annual grasses and certain broadleaf weeds, e.g., in rice, both seeded and transplanted.

As used herein, cafenstrole is N,N-diethyl-3-[(2,4,6-trimethylphenyl)sulfonyl]-1H-1,2,4-triazole-1-carboxamide and possesses the following structure:

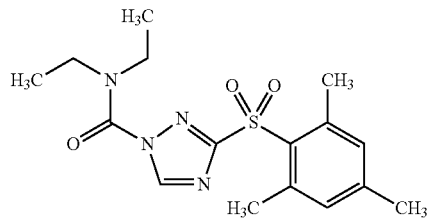

Its herbicidal activity is exemplified in *The Pesticide Manual*, Fifteenth Edition, 2009. Exemplary uses of cafenstrole include its use for pre- and post-emergence control of *Echinochloa oryzicola*, *Cyperus difformis* and other weeds, e.g., in paddy rice.

As used herein, dimethenamid is (RS)-2-chloro-N-(2,4-dimethyl-3-thienyl)-N-(2-methoxy-1-methylethyl)acetamide and possesses the following structure:

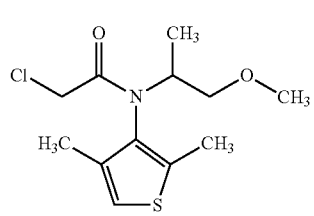 [SMILES: COCC(C)N(C(=O)CCl)c1c(C)csc1C]

The S isomer, i.e., (S) 2-chloro-N-(2,4-dimethyl-3-thienyl)-N-(2-methoxy-1-methylethyl)acetamide has also been used as a herbicide. Herbicidal activity for dimethenamid is exemplified in Tomlin, C., ed. A World Compendium *The Pesticide Manual*. 15$^{th}$ ed. Alton: BCPC Publications, 2009 (hereafter "*The Pesticide Manual*, Fifteenth Edition, 2009."). Exemplary uses of dimethenamid include its use for pre- or early post-emergence control of annual grass and broadleaf weeds, e.g., in maize, soybeans, sugar beet, potatoes, dry beans and other crops.

As used herein, fentrazamide is 4-(2-chlorophenyl)-N-cyclohexyl-N-ethyl-4,5-dihydro-5-oxo-1H-tetrazole-1-carboxamide and possesses the following structure:

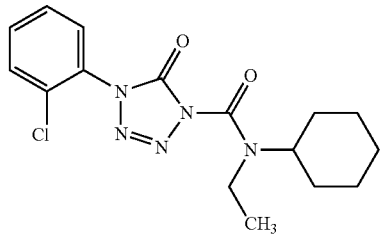 [SMILES: CCN(C(=O)n1nnn(-c2ccccc2Cl)c1=O)C1CCCCC1]

Its herbicidal activity is exemplified in *The Pesticide Manual*, Fifteenth Edition, 2009. Exemplary uses of fentrazamide include its use for control of barnyard grass (*Echinochloa* spp.) and annual sedges, from weed pre-emergence, e.g., in rice.

As used herein, flufenacet is N-(4-fluorophenyl)-N-(1-methylethyl)-2-[[5-(trifluoromethyl)-1,3,4-thiadiazol-2-yl]oxy]acetamide and possesses the following structure:

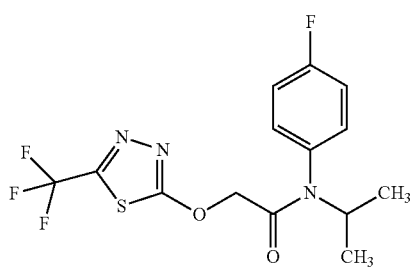 [SMILES: CC(C)N(C(=O)COc1nnc(C(F)(F)F)s1)c1ccc(F)cc1]

Its herbicidal activity is exemplified in *The Pesticide Manual*, Fifteenth Edition, 2009. Exemplary uses of flufenacet include its use for broad-spectrum grass control and control of broadleaf weeds.

As used herein, indanofan is (RS)-2-[[2-(3-chlorophenyl)oxiranyl]methyl]-2-ethyl-1H-indene-1,3(2H)-dione and possesses the following structure:

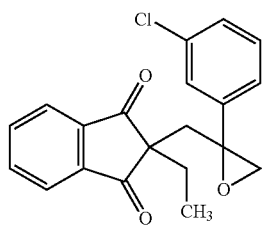 [SMILES: CCC1(CC2(c3cccc(Cl)c3)CO2)C(=O)c2ccccc2C1=O]

Its herbicidal activity is exemplified in *The Pesticide Manual*, Fifteenth Edition, 2009. Exemplary uses of indanofan include its use for pre-emergence and post-emergence weed control, e.g., in transplanted rice, and pre-emergence weed control in turf.

As used herein, mefenacet is 2-(2-benzothiazolyloxy)-N-methyl-N-phenylacetamide and possesses the following structure:

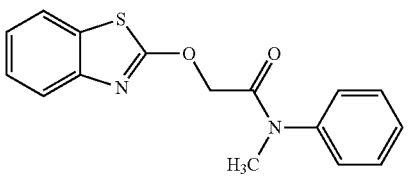

Its herbicidal activity is exemplified in *The Pesticide Manual*, Fifteenth Edition, 2009. Exemplary uses of mefenacet include its use for pre-emergence and early post-emergence control of grass weeds, e.g., in transplanted rice.

As used herein, S-metolachlor is a mixture of 2-chloro-N-(2-ethyl-6-methylphenyl)-N-[(1S)-2-methoxy-1-methyl ethyl]acetamide and 2-chloro-N-(2-ethyl-6-methylphenyl)-N-[(1R)-2-methoxy-1-methylethyl]acetamide, wherein the mixture contains predominantly S-isomer, e.g., 80-100%. Metolachlor has the following formula:

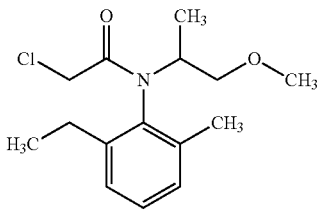 [SMILES: CCc1cccc(C)c1N(C(=O)CCl)C(C)COC]

Its herbicidal activity is exemplified in *The Pesticide Manual*, Fifteenth Edition, 2009. Exemplary uses of S-metolachlor include its use for control of annual grasses and broadleaf weeds, e.g., in maize, sorghum, cotton, sugar beet, fodder beet, sugar cane, potatoes, peanuts, soybeans, safflowers, sunflowers, various vegetables, fruit and nut trees, and woody ornamentals.

As used herein, molinate is S-ethyl hexahydro-1H-azepine-1-carbothioate and possesses the following structure:

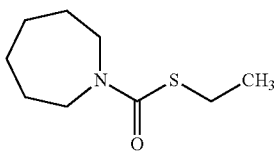

Its herbicidal activity is exemplified in *The Pesticide Manual*, Fifteenth Edition, 2009. Exemplary uses of molinate include its use for control of germinating broadleaf and grass weeds, e.g., in rice.

As used herein, pethoxamid is 2-Chloro-N-(2-ethoxyethyl)-N-(2-methyl-1-phenyl-1-propen-1-yl)acetamide and possesses the following structure:

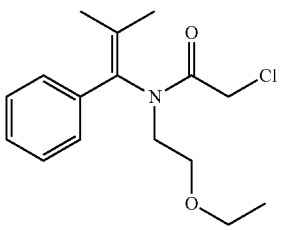 [SMILES: CCOCCN(C(=O)CCl)C(=C(C)C)c1ccccc1]

Its herbicidal activity is exemplified in *The Pesticide Manual*, Fifteenth Edition, 2009. Exemplary uses of pethoxamid include its use for pre-emergence to early post-emergence control of *Echinochloa, Digitaria, Setaria, Amaranthus* and *Chenopodium* spp., and other monocotyledonous and annual broadleaf weeds, e.g., in corn/maize, oilseed rape and soybeans.

As used herein, pretilachlor is 2-chloro-N-(2,6-diethylphenyl)-N-(2-propoxyethyl)acetamide and possesses the following structure:

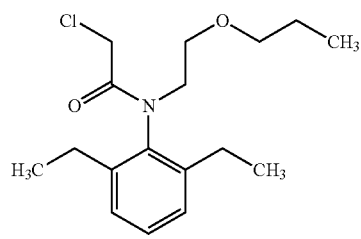 [SMILES: CCCOCCN(C(=O)CCl)c1c(CC)cccc1CC]

Its herbicidal activity is exemplified in *The Pesticide Manual*, Fifteenth Edition, 2009. Exemplary uses of pretilachlor include its use for control of annual grasses, broadleaf weeds and sedges, e.g., in transplanted and seeded rice.

As used herein, prosulfocarb is S-(phenylmethyl) dipropylcarbamothioate and possesses the following structure:

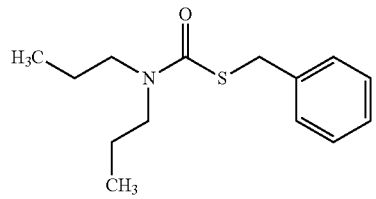 [SMILES: CCCN(CCC)C(=O)SCc1ccccc1]

Its herbicidal activity is exemplified in *The Pesticide Manual*, Fifteenth Edition, 2009. Exemplary uses of prosulfocarb include its use for pre- and early post-emergence control of grass and broadleaf weeds, e.g., in winter wheat, winter barley and rye.

As used herein, pyroxasulfone is 3-[[[5-(difluoromethoxy)-1-methyl-3-(trifluoromethyl)-1H-pyrazol-4-yl]methyl]sulfonyl]-4,5-dihydro-5,5-dimethylisoxazole and possesses the following structure:

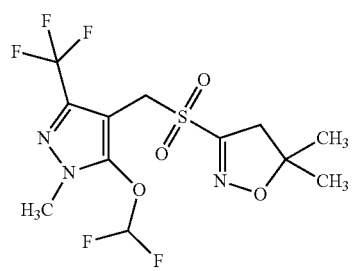 [SMILES: Cn1nc(C(F)(F)F)c(CS(=O)(=O)C2=NOC(C)(C)C2)c1OC(F)F]

Its herbicidal activity is exemplified in *The Pesticide Manual*, Fifteenth Edition, 2009. Pyroxasulfone provides, e.g., pre-emergence control of annual grasses and some broadleaf weeds in maize, soybeans, wheat and other crops.

As used herein, thenylchlor is 2-chloro-N-(2,6-dimethylphenyl)-N-[(3-methoxy-2-thienyl)methyl]acetamide and possesses the following structure:

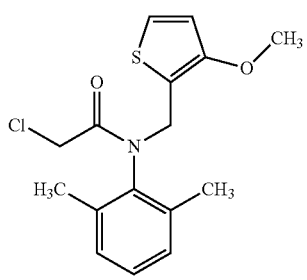 [SMILES: COc1ccsc1CN(C(=O)CCl)c1c(C)cccc1C]

Its herbicidal activity is exemplified in *The Pesticide Manual*, Fifteenth Edition, 2009. Exemplary uses of thenylchlor include its use for pre-emergence control of annual grass and broadleaf weeds, e.g., in paddy rice.

As used herein, thiobencarb is S-[(4-chlorophenyl)methyl]N,N-diethylcarbamothioate and possesses the following structure:

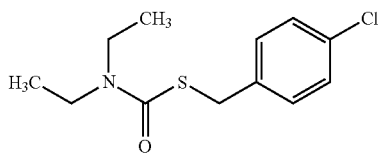 [SMILES: CCN(CC)C(=O)SCc1ccc(Cl)cc1]

Its herbicidal activity is exemplified in *The Pesticide Manual*, Fifteenth Edition, 2009. Exemplary uses of thiobencarb include its use for pre-emergence to early post-emergence control of *Echinochloa, Leptochloa* and *Cyperus* spp., and other monocotyledonous and annual broadleaf weeds, e.g., in direct-seeded and transplanted rice.

As used herein, herbicide means a compound, e.g., active ingredient that kills, controls or otherwise adversely modifies the growth of plants.

As used herein, a herbicidally effective or vegetation controlling amount is an amount of active ingredient which causes an adversely modifying effect to the vegetation e.g., causing deviations from natural development, killing, effecting regulation, causing desiccation, causing retardation, and the like.

As used herein, controlling undesirable vegetation means preventing, reducing, killing, or otherwise adversely modifying the development of plants and vegetation. Described herein are methods of controlling undesirable vegetation through the application of certain herbicide combinations or compositions. Methods of application include, but are not limited to applications to the vegetation or locus thereof, e.g., application to the area adjacent to the vegetation, as well as pre-emergence, post-emergence, foliar (broadcast, directed, banded, spot, mechanical, over-the-top, or rescue), and in-water applications (emerged and submerged vegetation, broadcast, spot, mechanical, water-injected, granular broadcast, granular spot, shaker bottle, or stream spray) via hand, backpack, machine, tractor, or aerial (airplane and helicopter) application methods.

As used herein, plants and vegetation include, but are not limited to, germinant seeds, emerging seedlings, plants emerging from vegetative propagules, immature vegetation, and established vegetation.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can be hydrolyzed, oxidized, metabolized, or otherwise converted, e.g., in plants, water, or soil, to the corresponding carboxylic acid which, depending on the pH, may be in the dissociated or undissociated form.

Exemplary salts include those derived from alkali or alkaline earth metals and those derived from ammonia and amines. Exemplary cations include sodium, potassium, magnesium, and aminium cations of the formula:

$$R^1R^2R^3R^4N^+$$

wherein $R^1$, $R^2$, $R^3$ and $R^4$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts can be prepared by treatment with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide.

Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the acids with the alcohol using any number of suitable activating agents such as those used for peptide couplings such as dicyclohexylcarbodiimide (DCC) or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

Compositions and Methods

Provided herein are herbicidal compositions comprising a herbicidally effective amount of (a) a compound of the formula (I)

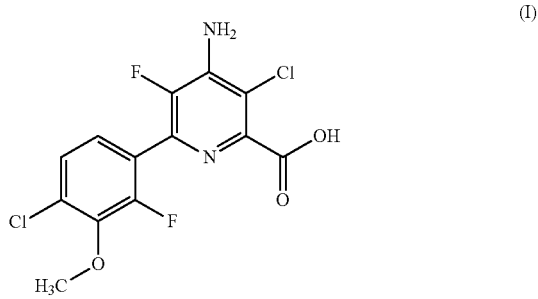 [SMILES: COc1c(Cl)ccc(-c2nc(C(=O)O)c(Cl)c(N)c2F)c1F]

or an agriculturally acceptable salt or ester of thereof, and (b) VLCFA and fatty acid/lipid synthesis inhibiting herbicides. In some embodiments, the VLCFA and fatty acid/lipid synthesis inhibiting herbicide is acetochlor, alachlor, anilofos, butachlor, benfuresate, cafenstrole, dimethenamid, fentrazamide, indanofan, flufenacet, mefenacet, s-metolachlor, molinate, pethoxamid, pretilachlor, prosulfocarb, pyroxasulfone, thenylchlor and thiobencarb, or a salt thereof.

Provided herein are also methods of controlling undesirable vegetation comprising contacting the vegetation or the locus thereof, i.e., the area adjacent to the vegetation with or applying to the soil or water to prevent the emergence or growth of vegetation a herbicidally effective amount of the compound of formula (I) or salt of ester thereof and (b) VLCFA and fatty acid/lipid synthesis inhibiting herbicides. In certain embodiments, the methods employ the compositions described herein.

Furthermore, in some embodiments, the combination of compound (I) or agriculturally acceptable salt or ester thereof and VLCFA and fatty acid/lipid synthesis inhibiting herbicides, or an agriculturally acceptable salt or ester thereof exhibits synergism, e.g., the herbicidal active ingredients are more effective in combination than when applied individually. Synergism has been defined as "an interaction of two or more factors such that the effect when combined is greater than the predicted effect based on the response of each factor applied separately." Senseman, S., ed. Herbicide Handbook. 9$^{th}$ ed. Lawrence: Weed Science Society of America, 2007. In certain embodiments, the compositions exhibit synergy as determined by the Colby's equation. Colby, S. R. 1967. Calculation of the synergistic and antagonistic response of herbicide combinations. Weeds 15:20-22.

In certain embodiments of the compositions and methods described herein, the compound of formula (I), i.e., the carboxylic acid, is employed. In certain embodiments, a carboxylate salt of the compound of formula (I) is employed. In certain embodiments, an aralkyl or alkyl ester is employed. In certain embodiments, a benzyl, substituted benzyl, or $C_{1-4}$ alkyl, e.g., n-butyl ester is employed. In certain embodiments, the benzyl ester is employed.

In some embodiments, the compound of formula (I) or salt or ester thereof and acetochlor, alachlor, anilofos, butachlor, benfuresate, cafenstrole, dimethenamid, fentrazamide, indanofan, flufenacet, mefenacet, s-metolachlor, molinate, pethoxamid, pretilachlor, prosulfocarb, pyroxasulfone, thenylchlor and thiobencarb, or an agriculturally acceptable salt thereof are formulated in one composition, tank mixed, applied simultaneously, or applied sequentially.

Herbicidal activity is exhibited by the compounds when they are applied directly to the plant or to the locus of the plant at any stage of growth. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted to promote non-selective or selective herbicidal action. In some embodiments, the compositions described herein are applied as a post-emergence application, pre-emergence application, or in-water application to flooded paddy rice or water bodies (e.g., ponds, lakes and streams), to relatively immature undesirable vegetation to achieve the maximum control of weeds.

In some embodiments, the compositions and methods provided herein are utilized to control weeds in crops, including but not limited to direct-seeded, water-seeded and transplanted rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, aquatics, plantation crops, vegetables, industrial vegetation management (IVM) and rights-of-way (ROW).

In certain embodiments, the compositions and methods provided herein are utilized to control weeds in rice. In certain embodiments, the rice is direct-seeded, water-seeded, or transplanted rice.

The compositions and methods described herein may be used to control undesirable vegetation in glyphosate-tolerant-, 5-enolpyruvylshikimate-3-phosphate (EPSP) synthase inhibitor-tolerant-, glufosinate-tolerant-, glutamine synthetase inhibitor-tolerant-, dicamba-tolerant-, phenoxy auxin-tolerant-, pyridyloxy auxin-tolerant-, auxin-tolerant-, auxin transport inhibitor-tolerant-, aryloxyphenoxypropionate-tolerant-, cyclohexanedione-tolerant-, phenylpyrazoline-tolerant-, acetyl CoA carboxylase (ACCase) inhibitor-tolerant-, imidazolinone-tolerant-, sulfonylurea-tolerant-, pyrimidinylthiobenzoate-tolerant-, triazolopyrimidine-tolerant-, sulfonylaminocarbonyltriazolinone-tolerant-, acetolactate synthase (ALS) or acetohydroxy acid synthase (AHAS) inhibitor-tolerant-, 4-hydroxyphenyl-pyruvate dioxygenase (HPPD) inhibitor-tolerant-, phytoene desaturase inhibitor-tolerant-, carotenoid biosynthesis inhibitor-tolerant-, protoporphyrinogen oxidase (PPO) inhibitor-tolerant-, cellulose biosynthesis inhibitor-tolerant-, mitosis inhibitor-tolerant-, microtubule inhibitor-tolerant-, very long chain fatty acid inhibitor-tolerant-, fatty acid and lipid biosynthesis inhibitor-tolerant-, photosystem I inhibitor-tolerant-, photosystem II inhibitor-tolerant-, triazine-tolerant-, bromoxynil-tolerant-crops (such as, but not limited to, soybean, cotton, canola/oilseed rape, rice, cereals, corn, sorghum, sunflower, sugar beet, sugarcane, turf, etc.), for example, in conjunction with glyphosate, EPSP synthase inhibitors, glufosinate, glutamine synthase inhibitors, dicamba, phenoxy auxins, pyridyloxy auxins, synthetic auxins, auxin transport inhibitors, aryloxyphenoxypropionates, cyclohexanediones, phenylpyrazolines, ACCase inhibitors, imidazolinones, sulfonylureas, pyrimidinylthiobenzoates, triazolopyrimidines, sulfonylaminocarbonyltriazolinones, ALS or AHAS inhibitors, HPPD inhibitors, phytoene desaturase inhibitors, carotenoid biosynthesis inhibitors, PPO inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil. The compositions and methods may be used in controlling undesirable vegetation in crops possessing multiple or stacked traits conferring tolerance to multiple chemistries and/or inhibitors of multiple modes of action. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation, as a tank mix, or sequentially.

The compositions and methods may be used in controlling undesirable vegetation in crops possessing agronomic stress tolerance (including but not limited to drought, cold, heat, salt, water, nutrient, fertility, pH), pest tolerance (including but not limited to insects, fungi and pathogens) and crop improvement traits (including but not limited to yield; protein, carbohydrate, or oil content; protein, carbohydrate, or oil composition; plant stature and plant architecture).

The compositions and methods provided herein are utilized to control undesirable vegetation. Undesirable vegetation includes, but is not limited to, undesirable vegetation that occurs in direct-seeded, water-seeded, and transplanted rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, ornamental species, aquatics, plantation crops, vegetables, industrial vegetation management (IVM) and rights of way (ROW).

In some embodiments, the methods provided herein are utilized to control undesirable vegetation in rice. In certain embodiments, the undesirable vegetation is *Brachiaria platyphylla* (Groseb.) Nash or *Urochloa platyphylla* (Nash) R. D. Webster (broadleaf signalgrass, BRAPP), *Digitaria sanguinalis* (L.) Scop. (large crabgrass, DIGSA), *Echinochloa* species (ECHSS), *Echinochloa crus-galli* (L.) P. Beauv. (barnyardgrass, ECHCG), *Echinochloa crus-pavonis* (Kunth) Schult. (gulf cockspur, ECHCV), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Echinochloa phyllopogon* (Stapf) Koso-Pol. (rice barnyardgrass, ECHPH), *Echinochloa polystachya* (Kunth) Hitchc. (creeping river grass, ECHPO), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl.) Hitchc. (Amazon sprangletop, LEFPA), *Oryza* species (red and weedy rice, ORYSS), *Panicum dichotomiflorum* (L.) Michx. (fall panicum, PANDI), *Paspalum dilatatum* Poir. (dallisgrass, PASDI), *Rottboellia cochinchinensis* (Lour.) W. D. Clayton (itchgrass, ROOEX), *Cyperus* species (CYPSS), *Cyperus difformis* L. (smallflower flatsedge, CYPDI), *Cyperus dubius* Rottb. (MAPDU), *Cyperus esculentus* L. (yellow nutsedge, CYPES), *Cyperus iria* L. (rice flatsedge, CYPIR), *Cyperus rotundus* L. (purple nutsedge, CYPRO), *Cyperus serotinus* Rottb./C. B. Clarke (tidalmarsh flatsedge CYPSE), *Eleocharis* species (ELOSS), *Fimbristylis miliacea* (L.) Vahl (globe fringerush, FIMMI), *Schoenoplectus* species (SCPSS), *Schoenoplectus juncoides* Roxb. (Japanese bulrush, SCPJU), *Bolboschoenus maritimus* (L.) Palla or *Schoenoplectus maritimus* L. Lye (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Commelina benghalensis* L. (Benghal dayflower, COMBE), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea* species (morningglories, IPOSS), *Ipomoea hederacea* (L.) Jacq. (ivyleaf morningglory, IPOHE), *Lindernia dubia* (L.) Pennell (low false pimpernel, LIDDU), *Ludwigia* species (LUDSS), *Ludwigia linifolia* Poir. (southeastern primrose-willow, LUDLI), *Ludwigia octovalvis* (Jacq.) Raven (longfruited primrose-willow, LUDOC), *Monochoria korsakowii* Regel & Maack (monochoria, MOOKA), *Monochoria vaginalis* (Burm. F.) C. Presl ex Kuhth, (monochoria, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (POLHP, mild smartweed), *Rotala indica* (Willd.) Koehne (Indian toothcup, ROTIN), *Sagittaria* species, (arrowhead, SAGSS), *Sesbania exaltata* (Raf.) Cory/Rydb. Ex Hill (hemp sesbania, SEBEX), or *Sphenoclea zeylanica* Gaertn. (gooseweed, SPDZE).

In some embodiments, the methods provided herein are utilized to control undesirable vegetation in cereals. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multflorum* Lam. (Italian ryegrass, LOLMU), *Phalaris minor* Retz. (littleseed canarygrass, PHAMI), *Poa annua* L. (annual bluegrass, POANN), *Setaria pumila* (Poir.) Roemer & J. A. Schultes (yellow foxtail, SETLU), *Setaria viridis* (L.) Beauv. (green foxtail, SETVI), *Amaranthus retroflexus* L. (redroot pigweed, AMARE), *Brassica* species (BRSSS), *Chenopodium album* L. (common lambsquarters, CHEAL), *Cirsium arvense* (L.) Scop. (Canada thistle, CIRAR), *Galium aparine* L. (catchweed bedstraw, GALAP), *Kochia scoparia* (L.) Schrad. (kochia, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Sinapis* species (SINSS), *Sinapis arvensis* L. (wild mustard, SINAR), *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the methods provided herein are utilized to control undesirable vegetation in range and pasture, fallowland, IVM and ROW. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Daucus carota* L. (wild carrot, DAUCA), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly sida, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the methods provided herein are utilized to control undesirable vegetation found in row crops, tree and vine crops and perennial crops. In certain embodiments, the undesirable vegetation is *Alopecurus myosuroides* Huds. (blackgrass, ALOMY), *Avena fatua* L. (wild oat, AVEFA), *Brachiaria decumbens* Stapf. or *Urochloa decumbens* (Stapf) R. D. Webster (Surinam grass, BRADC), *Brachiaria brizantha* (Hochst. ex A. Rich.) Stapf. or *Urochloa brizantha* (Hochst. ex A. Rich.) R. D. (beard grass, BRABR), *Brachiaria platyphylla* (Groseb.) Nash or *Urochloa platyphylla* (Nash) R. D. Webster (broadleaf signalgrass, BRAPP), *Brachiaria plantaginea* (Link) Hitchc. or *Urochloa plantaginea* (Link) R. D. Webster (alexandergrass, BRAPL), *Cenchrus echinatus* L. (southern sandbar, CENEC), *Digitaria horizontalis* Willd. (Jamaican crabgrass, DIGHO), *Digitaria insularis* (L.) Mez ex Ekman (sourgrass, TRCIN), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Eleusine indica* (L.) Gaertn. (goosegrass, ELEIN), *Lolium multiflorum* Lam. (Italian ryegrass, LOLMU), *Panicum dichotomiflorum* Michx. (fall panicum, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) *Moench* ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Anoda cristata* (L.) Schlecht. (spurred anoda, ANVCR), *Asclepias syriaca* L. (common milkweed, ASCSY), *Bidens pilosa* L. (hairy beggarticks, BIDPI), *Borreria* species (BOISS), *Borreria alata* (Aubl.) DC. or *Spermacoce alata* Aubl. (broadleaf buttonweed, BOILF), *Spermacose latifolia* (broadleaved button weed, BOILF), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Euphorbia hirta* L. or *Chamaesyce hirta* (L.) Millsp. (garden spurge, EPHHI), *Euphorbia dentata* Michx. (toothed spurge, EPHDE), *Erigeron bonariensis* L. or *Conyza bonariensis* (L.) Cronq. (hairy fleabane, ERIBO), *Erigeron canadensis* L. or *Conyza canadensis* (L.) Cronq. (Canadian fleabane, ERICA), *Conyza sumatrensis* (Retz.) E. H. Walker (tall fleabane, ERIFL), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Richardia* species (pusley, RCHSS), *Sida* species (sida, SIDSS), *Sida spinosa* L. (prickly sida, SIDSP), *Sinapis arvensis* L. (wild mustard, SINAR), *Solanum ptychanthum* Dunal (eastern black nightshade, SOLPT), *Tridax procumbens* L. (coat buttons, TRQPR), or *Xanthium strumarium* L. (common cocklebur, XANST).

In some embodiments, the methods provided herein are utilized to control undesirable vegetation in turf. In certain embodiments, the undesirable vegetation is *Bellis perennis* L. (English daisy, BELPE), *Cyperus esculentus* L. (yellow nutsedge, CYPES), *Cyperus* species (CYPSS), *Digitaria sanguinalis* (L.) Scop. (large crabgrass, DIGSA), *Diodia virginiana* L. (Virginia buttonweed, DIQVI), *Euphorbia* species (spurge, EPHSS), *Glechoma hederacea* L. (ground ivy, GLEHE), *Hydrocotyle umbellata* L. (dollarweed, HYDUM), *Kylling a* species (kyllinga, KYLSS), *Lamium amplexicaule* L. (henbit, LAMAM), *Murdannia nudiflora* (L.) Brenan (doveweed, MUDNU), *Oxalis* species (woodsorrel, OXASS), *Plantago major* L. (broadleaf plantain, PLAMA), *Plantago lanceolata* L. (buckhorn/narrowleaf plantain, PLALA), *Phyllanthus urinaria* L. (chamberbitter, PYLTE), *Rumex obtusifolius* L. (broadleaf dock, RUMOB), *Stachys floridana* Shuttlew. (Florida betony, STAFL), *Stellaria media* (L.) Vill. (common chickweed, STEME), *Taraxacum officinale* G. H. Weber ex Wiggers (dandelion, TAROF), *Trifolium repens* L. (white clover, TRFRE), or *Viola* species (wild violet, VIOSS).

In some embodiments, the compositions and methods provided herein are utilized to control undesirable vegetation consisting of grass, broadleaf and sedge weeds. In certain embodiments, the compositions and methods provided herein are utilized to control undesirable vegetation including *Bolboschoenus, Brachiaria, Chenopodium, Cirsium, Cyperus, Digitaria, Echinochloa, Fimbristylis, Galium, Ipomoea, Ischaemum, Kochia, Leptochloa, Papaver, Polygonum, Salsola, Schoenoplectus, Sinapis, Stellaria* and *Xanthium*.

In some embodiments, the combination of compound (I) or agriculturally acceptable ester or salt thereof and VLCFA and fatty acid/lipid synthesis inhibiting herbicides or agriculturally acceptable salt or ester thereof is used to control *Brachiaria platyphylla* (Griseb.) Nash, or *Urochloa platyphylla* (Nash) R. D. Webster (broadleaf signalgrass, BRAPP), *Cyperus esculentus* L. (yellow nutsedge, CYPES), *Cyperus iria* L. (rice flatsedge, CYPIR), *Cyperus rotundus* L. (purple nutsedge, CYPRO), *Digitaria sanguinalis* (L.) Scop. (large crabgrass, DIGSA), *Echinochloa crus-galli* (L.) Beauv. (barnyardgrass, ECHCG), *Echinochloa colona* (L.) Link, (junglerice, ECHCO), *Echinochloa oryzoides* (Ard.) Fritsch (early watergrass, ECHOR), *Fimbristylis miliacea* (L.) Vahl (globe fringerush, FIMMI), *Galium aparine* L. (catchweed bedstraw, GALAP), *Ipomoea hederacea* Jacq. (ivyleaf morningglory, IPOHE), *Ischaemum rugosum* Salisb. (saramollagrass, ISCRU), *Kochia scoparia* (L.) Schrad. (kochia, KCHSC), *Leptochloa chinensis* (L.) Nees (Chinese sprangletop, LEFCH) *Papaver rhoeas* L. (common poppy, PAPRH), *Polygonum hydropiperoides* Michx. (POLHP, mild smartweed), *Salsola tragus* L. (Russian thistle, SASKR), *Schoenoplectus juncoides* (Roxb.) Palla (Japanese bulrush, SCPJU), *Sinapis arvensis* L. (wild mustard, SINAR), *Stellaria media* (L.) Vill. (common chickweed, STEME) and *Xanthium strumarium* L. (common cocklebur, XANST).

The compounds of formula I or agriculturally acceptable salt or ester thereof may be used to control herbicide resistant or tolerant weeds. The methods employing the combination of a compound of formula I or agriculturally acceptable salt or ester thereof and the compositions described herein may also be employed to control herbicide resistant or tolerant weeds. Exemplary resistant or tolerant weeds include, but are not limited to, biotypes resistant or tolerant to acetolactate synthase (ALS) or acetohydroxy acid synthase (AHAS) inhibitors (e.g., imidazolinones, sulfonylureas, pyrimidinylthiobenzoates, triazolopyrimidines, sulfonylaminocarbonyltriazolinones), photosystem II inhibitors (e.g., phenylcarbamates, pyridazinones, triazines, triazinones, uracils, amides, ureas, benzothiadiazinones, nitriles, phenylpyridazines), acetyl CoA carboxylase (ACCase) inhibitors (e.g., aryloxyphenoxypropionates, cyclohexanediones, phenylpyrazolines), synthetic auxins, (e.g., benzoic acids, phenoxycarboxylic acids, pyridine carboxylic acids, quinoline carboxylic acids), auxin transport inhibitors (e.g., phthalamates, semicarbazones), photosystem I inhibitors (e.g., bipyridyliums), 5-enolpyruvylshikimate-3-phosphate (EPSP) synthase inhibitors (e.g., glyphosate), glutamine synthetase inhibitors (e.g., glufosinate, bialafos), microtubule assembly inhibitors (e.g., benzamides, benzoic acids, dinitroanilines, phosphoramidates, pyridines), mitosis inhibitors (e.g., carbamates), very long chain fatty acid (VLCFA) inhibitors (e.g., acetamides, chloroacetamides, oxyacetamides, tetrazolinones), fatty acid and lipid synthesis inhibitors (e.g., phosphorodithioates, thiocarbamates, benzofuranes, chlorocarbonic acids), protoporphyrinogen oxidase (PPO) inhibitors (e.g., diphenylethers, N-phenylphthalimides, oxadiazoles, oxazolidinediones, phenylpyrazoles, pyrimidindiones, thiadiazoles, triazolinones), carotenoid biosynthesis inhibitors (e.g., clomazone, amitrole, aclonifen), inhibitors, phytoene desaturase (PDS) inhibitors (e.g., amides, anilidex, furanones, phenoxybutan-amides, pyridiazinones, pyridines), 4-hydroxyphenyl-pyruvate-dioxygenase (HPPD) inhibitors (e.g., callistemones, isoxazoles, pyrazoles, triketones), mitosis inhibitors, cellulose biosynthesis inhibitors (e.g., nitriles, benzamides, quinclorac, triazolocarboxamides), herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, biotypes with resistance or tolerance to multiple chemical classes, biotypes with resistance or tolerance to multiple herbicide modes-of-action, and biotypes with multiple resistance or tolerance mechanisms (e.g., target site resistance or metabolic resistance).

In some embodiments, an agriculturally acceptable salt of acetochlor, alachlor, anilofos, butachlor, benfuresate, cafenstrole, dimethenamid-P, fentrazamide, indanofan, flufenacet, mefenacet, s-metolachlor, molinate, pethoxamid, pretilachlor, prosulfocarb, pyroxasulfone, thenylchlor and thiobencarb is employed in the methods or compositions described herein.

In certain embodiments of the compositions and methods described herein, the compound of formula (I) or salt or ester thereof is used in combination with acetochlor. With regard to the compositions, in some embodiments, the weight ratio of the compound of formula (I) or salt or ester thereof to acetochlor is within the range of from about 1:1680 to about 6:1. In certain embodiments, the weight ratio of the compound of formula (I) or salt or ester thereof to acetochlor is within the range of from about 1:46 to about 1:1. In certain embodiments, the weight ratio of the compound of formula (I) or salt or ester thereof to acetochlor is within the range of from about 1:90 to about 1:2. In certain embodiments, the weight ratio of the compound of formula (I) or salt or ester thereof to acetochlor is within the range of from about 1:46 to about 1:5.5. In certain embodiments, the compositions provided herein comprise the compound of formula (I) or its benzyl ester and acetochlor. In one embodiment, the composition comprises the compound of formula (I) and acetochlor, wherein the weight ratio of the compound of formula (I) to acetochlor is about 1:46 to about 1:5.5. In one embodiment, the composition comprises the benzyl ester of the compound of formula (I) and acetochlor, wherein the weight ratio of the benzyl ester of the compound of formula (I) to acetochlor is about 1:23 to about 1:5.5. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 52 grams active ingredient per hectare (gai/ha) to about 3,660 gai/ha based on the total amount of active ingredients in the composition. In certain embodiments, the composition is applied at an application rate of from about 54 grams active ingredient per hectare (gai/ha) to about 235 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and acetochlor, e.g., sequentially or simultaneously. In some embodiments, the acetochlor is applied at a rate from about 50 gai/ha to about 3360 gai/ha and the compound of formula (I) of salt or ester thereof is applied at a rate from about 2 grams acid equivalent per hectare (gae/ha) to about 300 gae/ha. In some embodiments, the acetochlor is applied at a rate from about 50 gai/ha to about 400 gai/ha and the compound of formula (I) of salt or ester thereof is applied at a rate from about 2 g acid equivalent per hectare (gae/ha) to about 45 gae/ha. In some embodiments, the acetochlor is applied at a rate from about 100 gai/ha to about 200 gai/ha and the compound of formula (I) of salt or ester thereof is applied at a rate from about 4.38 g acid equivalent per hectare (gae/ha) to about 17.5 gae/ha. In certain embodiments, the methods utilize the compound of formula (I), or its benzyl ester and acetochlor. In one embodiment, the methods utilize the compound of formula (I) and acetochlor, wherein the compound of formula (I) is applied at a rate of from about 4.38 g acid equivalent per hectare (gae/ha) to about 35 gae/ha, and acetochlor is applied at a rate of about 50 gai/ha to about 200 gai/ha. In one embodiment, the methods utilize the benzyl ester of the compound of formula (I) and acetochlor, wherein the benzyl ester of the compound of formula (I) is applied at a rate of from about 4.38 g acid equivalent per hectare (gae/ha) to about 35 gae/ha, and acetochlor is applied at a rate of about 50 gai/ha to about 200 gai/ha. In certain embodiments, the methods and compositions utilizing the compound of formula (I) or salt or ester thereof in combination with acetochlor are used to control BRAPP, DIGSA, ECHCG, ECHOR, CYPRO, LEFCH or FIMMI.

In certain embodiments of the compositions and methods described herein, the compound of formula (I) or salt or ester thereof is used in combination with alachlor. With regard to the compositions, in some embodiments, the weight ratio of the compound of formula (I) or salt or ester thereof to alachlor is within the range of from about 1:3350 to about 2:1. In certain embodiments, the weight ratio of the compound of formula (I) or salt or ester thereof to alachloror salt or ester thereof is within the range of from about 1:1000 to about 1:3. In certain embodiments, the weight ratio of the compound of formula (I) or salt or ester thereof to alachloror salt or ester thereof is within the range of from about 1:39 to about 1:78. In certain embodiments, the compositions comprise the compound of formula (I) or its benzyl or n-butyl ester and alachlor. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 172 grams active ingredient per hectare (gai/ha) to about 7000 gai/ha based on the total amount of active ingredients in the composition. In certain embodiments, the composition is applied at an application rate of from about 174 grams active ingredient per hectare (gai/ha) to about 2290 gai/ha based on the total amount of active ingredients in the composition. In certain embodiments, the composition is applied at an application rate of from about 1272 grams active ingredient per hectare (gai/ha) to about 2512 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and alachlor, e.g., sequentially or simultaneously. In some embodiments, the alachlor is applied at a rate from about 170 gai/ha to about 6700 gai/ha and the compound of formula (I) of salt or ester thereof is applied at a rate from about 2 gae/ha to about 300 gae/ha. In certain embodiments, the methods utilize the compound of formula (I) or its benzyl or n-butyl ester and alachlor. In certain embodiments, the methods and compositions utilizing the compound of formula (I) or salt or ester thereof in combination with alachlor are used to control IPOHE.

In certain embodiments of the compositions and methods described herein, the compound of formula (I) or salt or ester thereof is used in combination with anilofos. With regard to the compositions, in some embodiments, the weight ratio of the compound of formula (I) or salt or ester thereof to anilofos or salt or ester thereof is within the range of from about 1:250 to about 1.5:1. In certain embodiments, the weight ratio of the compound of formula (I) or salt or ester thereof to anilofos is within the range of from about 1:45 to about 1:1. In certain embodiments, the weight ratio of the compound of formula (I) or salt or ester thereof to anilofos is within the range of from about 1:50 to about 1:3. In certain embodiments, the compositions comprise the compound of formula (I) or its benzyl or n-butyl ester and anilofos. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 52 grams active ingredient per hectare (gai/ha) to about 750 gai/ha based on the total amount of active ingredients in the composition. In certain embodiments, the composition is applied at an application rate of from about 54 grams active ingredient per hectare (gai/ha) to about 235 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and anilofos, e.g., sequentially or simultaneously. In some embodiments, the anilofos is applied at a rate from about 50 gai/ha to about 450 gai/ha and the compound of formula (I) of salt or ester thereof is applied at a rate from about 2 gae/ha to about 300 gae/ha. In some embodiments, the anilofos is applied at a rate from about 100 gai/ha to about 400 gai/ha and the compound of formula (I) of salt or ester thereof is applied at a rate from about 8 gae/ha to about 32 gae/ha. In certain embodiments, the methods utilize the compound of formula (I) or its benzyl or n-butyl ester and anilofos. In certain embodiments, the methods and compositions utilizing the compound of formula (I) or salt or ester thereof in combination with aniliphos are used to control ECHCG, ECHOR, CYPRO or FIMMI.

In certain embodiments of the compositions and methods described herein, the compound of formula (I) or salt or ester thereof is used in combination with benfuresate. With regard to the compositions, in some embodiments, the weight ratio of the compound of formula (I) or salt or ester thereof to benfuresate is within the range of from about 1:150 to about 2:1. In certain embodiments, the weight ratio of the compound of formula (I) or salt or ester thereof to benfuresate is within the range of from about 1:113 to about 1.33:1. In certain embodiments, the weight ratio of the compound of formula (I) or salt or ester thereof to benfuresate is within the range of from about 1:70 to about 1:1 In certain embodiments, the weight ratio of the compound of formula (I) or salt or ester thereof to benfuresate is within the range of from about 1:70 to about 1:1. In certain embodiments, the weight ratio of the compound of formula (I) or salt or ester thereof to benfuresate is within the range of from about 1:36 to about 1:1.8. In certain embodiments, the compositions provided herein comprise the compound of formula (I) or its benzyl ester and benfuresate. In one embodiment, the composition comprises the compound of formula (I) and benfuresate, wherein the weight ratio of the compound of formula (I) to benfuresate is about 1:36 to about 1:1.8. In one embodiment, the composition comprises the benzyl ester of the compound of formula (I) and benfuresate, wherein the weight ratio of the benzyl ester of the compound of formula (I) to benfuresate is about 1:36 to about 1:2. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 52 grams active ingredient per hectare (gai/ha) to about 600 gai/ha based on the total amount of active ingredients in the composition. In certain embodiments, the composition is applied at an application rate of from about 55 grams active ingredient per hectare (gai/ha) to about 242 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and benfuresate or salt or ester thereof, e.g., sequentially or simultaneously. In some embodiments, benfuresate is applied at a rate from about 50 gai/ha to about 300 gai/ha and the compound of formula (I) of salt or ester thereof is applied at a rate from about 2 gae/ha to about 300 gae/ha. In some embodiments, the benfuresate is applied at a rate from about 25 gai/ha to about 1200 gai/ha and the compound of formula (I) of salt or ester thereof is applied at a rate from about 2 g acid equivalent per hectare (gae/ha) to about 200 gae/ha. In some embodiments, the benfuresate is applied at a rate from about 50 gai/ha to about 600 gai/ha and the compound of formula (I) of salt or ester thereof is applied at a rate from about 5.3 g acid equivalent per hectare (gae/ha) to about 100 gae/ha. In certain embodiments, the methods utilize the compound of formula (I), or its benzyl ester and benfuresate. In one embodiment, the methods utilize the compound of formula (I) and benfuresate, wherein the compound of formula (I) is applied at a rate of from about 5.3 g acid equivalent per hectare (gae/ha) to about 42.4 gae/ha, and benfuresate is applied at a rate of about 50 gai/ha to about 200 gai/ha. In one embodiment, the methods utilize the benzyl ester of the compound of formula (I) and benfuresate, wherein the benzyl ester of the compound of formula (I) is applied at a rate of from about 5.3 g acid equivalent per hectare (gae/ha) to about 100 gae/ha, and benfuresate is applied at a rate of about 50 gai/ha to about 600 gai/ha. In certain embodiments, the methods and compositions utilizing the compound of formula (I) or salt or ester thereof in combination with benfuresate are used to control ECHCG, ECHCO, LEFCH, CYPIR, POLHP, SCPJU or ECHOR.

In certain embodiments of the compositions and methods described herein, the compound of formula (I) or salt or ester thereof is used in combination with butachlor. With regard to the compositions, in some embodiments, the weight ratio of the compound of formula (I) or salt or ester thereof to butachlor is within the range of from about 1:750 to about 3:1. In certain embodiments, the weight ratio of the compound of formula (I) or salt or ester thereof to butachlor is within the range of from about 1:103 to about 1:6. In certain embodiments, the weight ratio of the compound of formula (I) or salt or ester thereof to butachlor is within the range of from about 1:200 to about 1:3. In certain embodiments, the weight ratio of the compound of formula (I) or salt or ester thereof to butachlor is within the range of from about 1:102 to about 1:6. In certain embodiments, the compositions provided herein comprise the compound of formula (I) or its benzyl or n-butyl ester and butachlor. In one embodiment, the composition comprises the compound of formula (I) and butachlor, wherein the weight ratio of the compound of formula (I) to butachlor is about 1:102 to about 1:6. In one embodiment, the composition comprises the benzyl ester of the compound of formula (I) and butachlor, wherein the weight ratio of the benzyl ester of the compound of formula (I) to butachlor is about 1:102 to about 1:6. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 115 grams active ingredient per hectare (gai/ha) to about 1800 gai/ha based on the total amount of active ingredients in the composition. In certain embodiments, the composition is applied at an application rate of from about 117 grams acid active ingredient per hectare (gai/ha) to about 468 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and butachlor, e.g., sequentially or simultaneously. In some embodiments, the butachlor is applied at a rate from about 113 gai/ha to about 1500 gai/ha and the compound of formula (I) of salt or ester thereof is applied at a rate from about 2 gae/ha to about 300 gae/ha. In some embodiments, the butachloror salt or ester thereof is applied at a rate from about 50 gai/ha to about 900 gai/ha and the compound of formula (I) of salt or ester thereof is applied at a rate from about 2 g acid equivalent per hectare (gae/ha) to about 45 gae/ha. In some embodiments, the butachloror salt or ester thereof is applied at a rate from about 112.5 gai/ha to about 450 gai/ha and the compound of formula (I) of salt or ester thereof is applied at a rate from about 4.38 g acid equivalent per hectare (gae/ha) to about 17.5 gae/ha. In certain embodiments, the methods utilize the compound of formula (I), or its benzyl or n-butyl ester and butachlor. In one embodiment, the methods utilize the compound of formula (I) and butachlor, wherein the compound of formula (I) is applied at a rate of from about 4.38 g acid equivalent per hectare (gae/ha) to about 35 gae/ha, and butachlor is applied at a rate of about 112.5 gai/ha to about 450 gai/ha. In one embodiment, the methods utilize the benzyl ester of the compound of formula (I) and butachlor, wherein the benzyl ester of the compound of formula (I) is applied at a rate of from about 4.38 g acid equivalent per hectare (gae/ha) to about 35 gae/ha, and butachlor is applied at a rate of about 112.5 gai/ha to about 450 gai/ha. In certain embodiments, the methods and compositions utilizing the compound of formula (I) or salt or ester thereof in combination with butachlor are used to control ECHCO, LEFCH, BRAPP, IPOHE, ECHCG, ECHOR, or CYPRO.

In certain embodiments of the compositions and methods described herein, the compound of formula (I) or salt or ester thereof is used in combination with cafenstrole. With regard to the compositions, in some embodiments, the weight ratio of the compound of formula (I) or salt or ester thereof to cafenstrole is within the range of from about 1:150 to about 2:1. In certain embodiments, the weight ratio of the compound of formula (I) or salt or ester thereof to cafenstrole is within the range of from about 1:24 to about 1:1. In certain embodiments, the weight ratio of the compound of formula (I) or salt or ester thereof to cafenstrole is within the range of from about 1:50 to about 2:1. In certain embodiments, the weight ratio of the compound of formula (I) or salt or ester thereof to cafenstrole is within the range of from about 1:24 to about 1:1.5. In certain embodiments, the compositions provided herein comprise the compound of formula (I) or its benzyl ester and cafenstrole. In one embodiment, the composition comprises the compound of formula (I) and cafenstrole, wherein the weight ratio of the compound of formula (I) to cafenstrole is about 1:24 to about 1:1.5. In one embodiment, the composition comprises the benzyl ester of the compound of formula (I) and cafenstrole, wherein the weight ratio of the benzyl ester of the compound of formula (I) to cafenstrole is about 1:24 to about 1:1.5. In one embodiment, the composition comprises the benzyl ester of the compound of formula (I) and cafenstrole, wherein the weight ratio of the benzyl ester of the compound of formula (I) to cafenstrole is about 1:47 to about 2.7:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 28 grams active ingredient per hectare (gai/ha) to about 600 gai/ha based on the total amount of active ingredients in the composition. In certain embodiments, the composition is applied at an application rate of from about 30 grams active ingredient per hectare (gai/ha) to about 150 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and cafenstrole, e.g., sequentially or simultaneously. In some embodiments, the cafenstrole is applied at a rate from about 26 gai/ha to about 300 gai/ha and the compound of formula (I) of salt or ester thereof is applied at a rate from about 2 gae/ha to about 300 gae/ha. In some embodiments, the cafenstrole is applied at a rate from about 10 gai/ha to about 200 gai/ha and the compound of formula (I) of salt or ester thereof is applied at a rate from about 2 g acid equivalent per hectare (gae/ha) to about 45 gae/ha. In some embodiments, the cafenstrole is applied at a rate from about 26.3 gai/ha to about 105 gai/ha and the compound of formula (I) of salt or ester thereof is applied at a rate from about 4.38 g acid equivalent per hectare (gae/ha) to about 17.5 gae/ha. In certain embodiments, the methods utilize the compound of formula (I), or its benzyl ester and cafenstrole. In one embodiment, the methods utilize the compound of formula (I) and cafenstrole, wherein the compound of formula (I) is applied at a rate of from about 4.38 g acid equivalent per hectare (gae/ha) to about 17.5 gae/ha, and cafenstrole is applied at a rate of about 26.3 gai/ha to about 105 gai/ha. In one embodiment, the methods utilize the benzyl ester of the compound of formula (I) and cafenstrole, wherein the benzyl ester of the compound of formula (I) is applied at a rate of from about 4.38 g acid equivalent per hectare (gae/ha) to about 17.5 gae/ha, and cafenstrole is applied at a rate of about 26.3 gai/ha to about 105 gai/ha. In one embodiment, the methods utilize the benzyl ester of the compound of formula (I) and cafenstrole, wherein the benzyl ester of the compound of formula (I) is applied at a rate of from about 4.38 g acid equivalent per hectare (gae/ha) to about 70 gae/ha, and cafenstrole is applied at a rate of about 26.3 gai/ha to about 210 gai/ha. In certain embodiments, the methods and compositions utilizing the compound of formula (I) or salt or ester thereof in combination with cafenstrole are used to control BRAPP, ECHCG, ECHCO, LEFCH, IPOHE, CYPIR, ECHOR, SCPJU or CYPRO.

In certain embodiments of the compositions and methods described herein, the compound of formula (I) or salt or ester thereof is used in combination with dimethenamid-P. With regard to the compositions, in some embodiments, the weight ratio of the compound of formula (I) or salt or ester thereof to dimethenamid-P is within the range of from about 1:850 to about 1:1. In certain embodiments, the weight ratio of the compound of formula (I) or salt or ester thereof to dimethenamid-P is within the range of from about 1:205 to about 1:8. In certain embodiments, the compositions comprise the compound of formula (I) or its benzyl or n-butyl ester and dimethenamid-P. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 282 grams active ingredient per hectare (gai/ha) to about 2,000 gai/ha based on the total amount of active ingredients in the composition. In certain embodiments, the composition is applied at an application rate of from about 283 grams active ingredient per hectare (gai/ha) to about 1,670 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and dimethenamid-P, e.g., sequentially or simultaneously. In some embodiments, the dimethenamid-P is applied at a rate from about 280 gai/ha to about 1,700 gai/ha and the compound of formula (I) of salt or ester thereof is applied at a rate from about 2 gae/ha to about 300 gae/ha. In some embodiments, the dimethenamid-P is applied at a rate from about 275 gai/ha to about 1,640 gai/ha and the compound of formula (I) of salt or ester thereof is applied at a rate from about 8 gae/ha to about 32 gae/ha. In certain embodiments, the methods utilize the compound of formula (I) or its benzyl or n-butyl ester and dimethenamid-P are used to control ECHCO and XANST.

In certain embodiments of the compositions and methods described herein, the compound of formula (I) or salt or ester thereof is used in combination with fentrazamide. With regard to the compositions, in some embodiments, the weight ratio of the compound of formula (I) or salt or ester thereof to fentrazamide is within the range of from about 1:150 to about 3:1. In certain embodiments, the weight ratio of the compound of formula (I) or salt or ester thereof to fentrazamide is within the range of from about 1:15 to about 1:1. In certain embodiments, the weight ratio of the compound of formula (I) or salt or ester thereof to fentrazamide is within the range of from about 1:68 to about 2:1. In certain embodiments, the weight ratio of the compound of formula (I) or salt or ester thereof to fentrazamide is within the range of from about 1:32 to about 2:1. In certain embodiments, the weight ratio of the compound of formula (I) or salt or ester thereof to fentrazamide is within the range of from about 1:16 to about 1:1.5. In certain embodiments, the compositions provided herein comprise the compound of formula (I) or its benzyl ester and fentrazamide. In one embodiment, the composition comprises the compound of formula (I) and fentrazamide, wherein the weight ratio of the compound of formula (I) to fentrazamide is about 1:16 to about 1:1.5. In one embodiment, the composition comprises the benzyl ester of the compound of formula (I) and fentrazamide, wherein the weight ratio of the benzyl ester of the compound of formula (I) to fentrazamide is about 1:8 to about 1:2. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 18 grams active ingredient per hectare (gai/ha) to about 600 gai/ha based on the total amount of active ingredients in the composition. In certain embodiments, the composition is applied at an application rate of from about 20 grams active ingredient per hectare (gai/ha) to about 150 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and fentrazamide, e.g., sequentially or simultaneously. In some embodiments, fentrazamide is applied at a rate from about 16 gai/ha to about 300 gai/ha and the compound of formula (I) of salt or ester thereof is applied at a rate from about 2 gae/ha to about 300 gae/ha. In some embodiments, the fentrazamide is applied at a rate from about 7 gai/ha to about 140 gai/ha and the compound of formula (I) of salt or ester thereof is applied at a rate from about 2 g acid equivalent per hectare (gae/ha) to about 45 gae/ha. In some embodiments, the fentrazamide is applied at a rate from about 16.9 gai/ha to about 67.5 gai/ha and the compound of formula (I) of salt or ester thereof is applied at a rate from about 4.38 g acid equivalent per hectare (gae/ha) to about 17.5 gae/ha. In certain embodiments, the methods utilize the compound of formula (I), or its benzyl ester and fentrazamide. In one embodiment, the methods utilize the compound of formula (I) and fentrazamide, wherein the compound of formula (I) is applied at a rate of from about 4.38 g acid equivalent per hectare (gae/ha) to about 17.5 gae/ha, and fentrazamide is applied at a rate of about 16.9 gai/ha to about 67.5 gai/ha. In one embodiment, the methods utilize the benzyl ester of the compound of formula (I) and fentrazamide, wherein the benzyl ester of the compound of formula (I) is applied at a rate of from about 4.38 g acid equivalent per hectare (gae/ha) to about 35 gae/ha, and fentrazamide is applied at a rate of about 33.8 gai/ha to about 300 gai/ha. In certain embodiments, the methods and compositions utilizing the compound of formula (I) or salt or ester thereof in combination with fentrazamide are used to control BRAPP, ECHCG, ECHCO, LEFCH, DIGSA, or ECHOR.

In certain embodiments of the compositions and methods described herein, the compound of formula (I) or salt or ester thereof is used in combination with flufenacet. With regard to the compositions, in some embodiments, the weight ratio of the compound of formula (I) or salt or ester thereof to flufenacet is within the range of from about 1:125 to about 12:1. In certain embodiments, the weight ratio of the compound of formula (I) or salt or ester thereof to flufenacet is within the range of from about 1:68 to about 6:1. In certain embodiments, the weight ratio of the compound of formula (I) or salt or ester thereof to flufenacet is within the range of from about 1:300 to about 1:2. In certain embodiments, the compositions comprise the compound of formula (I) or its benzyl or n-butyl ester and flufenacet. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 27 grams active ingredient per hectare (gai/ha) to about 550 gai/ha based on the total amount of active ingredients in the composition. In some embodiments, the composition is applied at an application rate of from about 62 grams active ingredient per hectare (gai/ha) to about 800 gai/ha based on the total amount of active ingredients in the composition. In certain embodiments, the composition is applied at an application rate of from about 28 grams active ingredient per hectare (gai/ha) to about 300 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and flufenacet, e.g., sequentially or simultaneously. In some embodiments, the flufenacet is applied at a rate from about 25 gai/ha to about 1,250 gai/ha and the compound of formula (I) of salt or ester thereof is applied at a rate from about 2 gae/ha to about 300 gae/ha. In some embodiments, the flufenacet is applied at a rate from about 60 gai/ha to about 750 gai/ha and the compound of formula (I) of salt or ester thereof is applied at a rate from about 8 gae/ha to about 32 gae/ha. In certain embodiments, the methods utilize the compound of formula (I) or its benzyl or n-butyl ester and flufenacet. In certain embodiments, the methods and compositions utilizing the compound of formula (I) or salt or ester thereof in combination with flufenacet are used to control BRAPP, CIRAR, CHEAL, KCHSC, PAPRH, SASKR, SINAR and STEME In certain embodiments of the compositions and methods described herein, the compound of formula (I) or salt or ester thereof is used in combination with indanofan. With regard to the compositions, in some embodiments, the weight ratio of the compound of formula (I) or salt or ester thereof to indanofan is within the range of from about 1:150 to about 12:1. In certain embodiments, the weight ratio of the compound of formula (I) or salt or ester thereof to indanofan is within the range of from about 1:136 to about 6:1. In certain embodiments, the compositions comprise the compound of formula (I) or its benzyl or n-butyl ester and indanofan. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 27 grams active ingredient per hectare (gai/ha) to about 600 gai/ha based on the total amount of active ingredients in the composition. In certain embodiments, the composition is applied at an application rate of from about 30 grams acid active ingredient per hectare (gai/ha) to about 450 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and indanofan, e.g., sequentially or simultaneously. In some embodiments, the indanofan is applied at a rate from about 25 gai/ha to about 300 gai/ha and the compound of formula (I) of salt or ester thereof is applied at a rate from about 2 gae/ha to about 300 gae/ha. In some embodiments, the indanofan is applied at a rate from about 37.5 gai/ha to about 150 gai/ha and the compound of formula (I) of salt or ester thereof is applied at a rate from about 8 gae/ha to about 32 gae/ha. In certain embodiments, the methods utilize the compound of formula (I) or its benzyl or n-butyl ester and indanofan. In certain embodiments, the methods and compositions utilizing the compound of formula (I) or salt or ester thereof in combination with indanofan are used to control ECHCO and LEFCH.

In certain embodiments of the compositions and methods described herein, the compound of formula (I) or salt or ester thereof is used in combination with mefenacet. With regard to the compositions, in some embodiments, the weight ratio of the compound of formula (I) or salt or ester thereof to mefenacet is within the range of from about 1:800 to about 1:1. In certain embodiments, the weight ratio of the compound of formula (I) or salt or ester thereof to mefenacet is within the range of from about 1:727 to about 1:2. In certain embodiments, the weight ratio of the compound of formula (I) or salt or ester thereof to mefenacet is within the range of from about 1:150 to about 1:2. In certain embodiments, the compositions comprise the compound of formula (I) or its benzyl or n-butyl ester and mefenacet. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 252 grams active ingredient per hectare (gai/ha) to about 1900 gai/ha based on the total amount of active ingredients in the composition. In certain embodiments, the composition is applied at an application rate of from about 255 grams acid active ingredient per hectare (gai/ha) to about 1750 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and mefenacet or salt thereof, e.g., sequentially or simultaneously. In some embodiments, the mefenacet is applied at a rate from about 250 gai/ha to about 1600 gai/ha and the compound of formula (I) of salt or ester thereof is applied at a rate from about 2 gae/ha to about 300 gae/ha. In some embodiments, the mefenacet is applied at a rate from about 50 gai/ha to about 1200 gai/ha and the compound of formula (I) of salt or ester thereof is applied at a rate from about 8 gae/ha to about 32 gae/ha. In certain embodiments, the methods utilize the compound of formula (I) or its benzyl or n-butyl ester and mefenacet. In certain embodiments, the methods and compositions utilizing the compound of formula (I) or salt or ester thereof in combination with mefenacet are used to control BRAPP, LEFCH, CYPIR or ECHOR.

In certain embodiments of the compositions and methods described herein, the compound of formula (I) or salt or ester thereof is used in combination with s-metolachlor. With regard to the compositions, in some embodiments, the weight ratio of the compound of formula (I) or salt or ester thereof to s-metolachlor is within the range of from about 1:1500 to about 4:1. In certain embodiments, the weight ratio of the compound of formula (I) or salt or ester thereof to s-metolachlor is within the range of from about 1:1000 to about 1:1. In certain embodiments, the weight ratio of the compound of formula (I) or salt or ester thereof to s-metolachlor is within the range of from about 1:194 to about 1:12. In certain embodiments, the compositions comprise the compound of formula (I) or its benzyl or n-butyl ester and s-metolachlor. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 72 grams active ingredient per hectare (gai/ha) to about 3300 gai/ha based on the total amount of active ingredients in the composition. In certain embodiments, the composition is applied at an application rate of from about 73 grams active ingredient per hectare (gai/ha) to about 2290 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and s-metolachlor, e.g., sequentially or simultaneously. In some embodiments, the s-metolachlor is applied at a rate from about 70 gai/ha to about 3000 gai/ha and the compound of formula (I) of salt or ester thereof is applied at a rate from about 2 gae/ha to about 300 gae/ha. In some embodiments, the s-metolachlor is applied at a rate from about 387 gai/ha to about 1550 gai/ha and the compound of formula (I) of salt or ester thereof is applied at a rate from about 8 gae/ha to about 32 gae/ha. In certain embodiments, the methods utilize the compound of formula (I) or its benzyl or n-butyl ester and s-metolachlor. In certain embodiments, the methods and compositions utilizing the compound of formula (I) or salt or ester thereof in combination with s-metolachlor are used to control ECHCG or IPOHE.

In certain embodiments of the compositions and methods described herein, the compound of formula (I) or salt or ester thereof is used in combination with molinate. With regard to the compositions, in some embodiments, the weight ratio of the compound of formula (I) or salt or ester thereof to molinate is within the range of from about 1:2780 to about 1:4. In certain embodiments, the weight ratio of the compound of formula (I) or salt or ester thereof to molinate is within the range of from about 1:255 to about 1:8. In certain embodiments, the weight ratio of the compound of formula (I) or salt or ester thereof to molinate is within the range of from about 1:194 to about 1:44. In certain embodiments, the compositions comprise the compound of formula (I) or its benzyl or n-butyl ester and molinate. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 282 grams active ingredient per hectare (gai/ha) to about 5860 gai/ha based on the total amount of active ingredients in the composition. In certain embodiments, the composition is applied at an application rate of from about 284 grams active ingredient per hectare (gai/ha) to about 1155 gai/ha based on the total amount of active ingredients in the composition. In certain embodiments, the composition is applied at an application rate of from about 1408 grams active ingredient per hectare (gai/ha) to about 2832 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and molinate, e.g., sequentially or simultaneously. In some embodiments, the molinate is applied at a rate from about 280 gai/ha to about 5560 gai/ha and the compound of formula (I) of salt or ester thereof is applied at a rate from about 2 gae/ha to about 300 gae/ha. In some embodiments, the molinate is applied at a rate from about 1400 gai/ha to about 2800 gai/ha and the compound of formula (I) of salt or ester thereof is applied at a rate from about 8 gae/ha to about 32 gae/ha. In certain embodiments, the methods utilize the compound of formula (I) or its benzyl or n-butyl ester and molinate. In certain embodiments, the methods and compositions utilizing the compound of formula (I) or salt or ester thereof in combination with s-molinate are used to control ECHOR.

In certain embodiments of the compositions and methods described herein, the compound of formula (I) or salt or ester thereof is used in combination with pethoxamid. With regard to the compositions, in some embodiments, the weight ratio of the compound of formula (I) or salt or ester thereof to pethoxamid is within the range of from about 1:625 to about 1:10. In certain embodiments, the weight ratio of the compound of formula (I) or salt or ester thereof to pethoxamid is within the range of from about 1:150 to about 1:38. In certain embodiments, the compositions comprise the compound of formula (I) or its benzyl or n-butyl ester and pethoxamid. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 202 grams active ingredient per hectare (gai/ha) to about 1,550 gai/ha based on the total amount of active ingredients in the composition. In certain embodiments, the composition is applied at an application rate of from about 313 grams acid active ingredient per hectare (gai/ha) to about 1,252 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and pethoxamid, e.g., sequentially or simultaneously. In some embodiments, the pethoxamid is applied at a rate from about 200 gai/ha to about 1,250 gai/ha and the compound of formula (I) of salt or ester thereof is applied at a rate from about 2 gae/ha to about 300 gae/ha. In some embodiments, the pethoxamid is applied at a rate from about 305 gai/ha to about 1,220 gai/ha and the compound of formula (I) of salt or ester thereof is applied at a rate from about 8 gae/ha to about 32 gae/ha. In certain embodiments, the methods utilize the compound of formula (I) or its benzyl or n-butyl ester in combination with pethoxamid are used to control LEFCH, CYPRO or CYPIR.

In certain embodiments of the compositions and methods described herein, the compound of formula (I) or salt or ester thereof is used in combination with pretilachlor. With regard to the compositions, in some embodiments, the weight ratio of the compound of formula (I) or salt or ester thereof to pretilachlor is within the range of from about 1:375 to about 2:1. In certain embodiments, the weight ratio of the compound of formula (I) or salt or ester thereof to pretilachlor is within the range of from about 1:34 to about 1:1. In certain embodiments, the weight ratio of the compound of formula (I) or salt or ester thereof to pretilachlor is within the range of from about 1:64 to about 1:1. In certain embodiments, the weight ratio of the compound of formula (I) or salt or ester thereof to pretilachlor is within the range of from about 1:32 to about 1:2. In certain embodiments, the weight ratio of the compound of formula (I) or salt or ester thereof to pretilachlor is within the range of from about 1:91 to about 2.7:1. In certain embodiments, the compositions provided herein comprise the compound of formula (I) or its benzyl ester and pretilachlor. In one embodiment, the composition comprises the compound of formula (I) and pretilachlor, wherein the weight ratio of the compound of formula (I) to pretilachlor is about 1:32 to about 1:2. In one embodiment, the composition comprises the benzyl ester of the compound of formula (I) and pretilachlor, wherein the weight ratio of the benzyl ester of the compound of formula (I) to pretilachlor is about 1:32 to about 1:4. In one embodiment, the composition comprises the benzyl ester of the compound of formula (I) and pretilachlor, wherein the weight ratio of the benzyl ester of the compound of formula (I) to pretilachlor is about 1:91 to about 2>7:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 40 grams active ingredient per hectare (gai/ha) to about 1050 gai/ha based on the total amount of active ingredients in the composition. In certain embodiments, the composition is applied at an application rate of from about 43 grams active ingredient per hectare (gai/ha) to about 500 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and pretilachlor, e.g., sequentially or simultaneously. In some embodiments, the pretilachlor is applied at a rate from about 38 gai/ha to about 750 gai/ha and the compound of formula (I) of salt or ester thereof is applied at a rate from about 2 gae/ha to about 300 gae/ha. In some embodiments, the pretilachlor is applied at a rate from about 18 gai/ha to about 300 gai/ha and the compound of formula (I) of salt or ester thereof is applied at a rate from about 2 g acid equivalent per hectare (gae/ha) to about 45 gae/ha. In some embodiments, the pretilachlor is applied at a rate from about 37.5 gai/ha to about 150 gai/ha and the compound of formula (I) of salt or ester thereof is applied at a rate from about 4.38 g acid equivalent per hectare (gae/ha) to about 17.5 gae/ha. In some embodiments, the pretilachlor is applied at a rate from about 37.5 gai/ha to about 400 gai/ha and the compound of formula (I) of salt or ester thereof is applied at a rate from about 4.38 g acid equivalent per hectare (gae/ha) to about 100 gae/ha. In certain embodiments, the methods utilize the compound of formula (I), or its benzyl ester and pretilachlor. In one embodiment, the methods utilize the compound of formula (I) and pretilachlor, wherein the compound of formula (I) is applied at a rate of from about 4.38 g acid equivalent per hectare (gae/ha) to about 17.5 gae/ha, and pretilachlor is applied at a rate of about 37.5 gai/ha to about 150 gai/ha. In one embodiment, the methods utilize the benzyl ester of the compound of formula (I) and pretilachlor, wherein the benzyl ester of the compound of formula (I) is applied at a rate of from about 4.38 g acid equivalent per hectare (gae/ha) to about 100 gae/ha, and pretilachlor is applied at a rate of about 37.5 gai/ha to about 400 gai/ha. In certain embodiments, the methods and compositions utilizing the compound of formula (I) or salt or ester thereof in combination with pretilachlor are used to control BRAPP, ECHCO, DIGSA, CYPIR, ECHCG, ECHOR, CYPRO, FIMMI, or SCPJU.

In certain embodiments of the compositions and methods described herein, the compound of formula (I) or salt or ester thereof is used in combination with prosulfocarb. With regard to the compositions, in some embodiments, the weight ratio of the compound of formula (I) or salt or ester thereof to prosulfocarb is within the range of from about 1:2000 to about 1:1.5. In certain embodiments, the weight ratio of the compound of formula (I) or salt or ester thereof to prosulfocarb is within the range of from about 1:1818 to about 1:10. In certain embodiments, the weight ratio of the compound of formula (I) or salt or ester thereof to prosulfocarb is within the range of from about 1:1600 to about 1:100. In certain embodiments, the compositions comprise the compound of formula (I) or its benzyl or n-butyl ester and prosulfocarb. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 502 grams active ingredient per hectare (gai/ha) to about 4300 gai/ha based on the total amount of active ingredients in the composition. In certain embodiments, the composition is applied at an application rate of from about 510 grams acid active ingredient per hectare (gai/ha) to about 4050 gai/ha based on the total amount of active ingredients in the composition. In certain embodiments, the composition is applied at an application rate of from about 1,002 grams acid active ingredient per hectare (gai/ha) to about 4010 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and prosulfocarb, e.g., sequentially or simultaneously. In some embodiments, the prosulfocarb is applied at a rate from about 500 gai/ha to about 4000 gai/ha and the compound of formula (I) of salt or ester thereof is applied at a rate from about 2 gae/ha to about 300 gae/ha. In some embodiments, the prosulfocarb is applied at a rate from about 1,000 gai/ha to about 4,000 gai/ha and the compound of formula (I) of salt or ester thereof is applied at a rate from about 2.0 gae/ha to about 100 gae/ha. In some embodiments, the prosulfocarb is applied at a rate from about 1,000 gai/ha to about 4,000 gai/ha and the compound of formula (I) of salt or ester thereof is applied at a rate from about 2.5 gae/ha to about 10 gae/ha. In certain embodiments, the methods utilize the compound of formula (I) or its benzyl or n-butyl ester and prosulfocarb. In certain embodiments, the methods and compositions utilizing the compound of formula (I) or salt or ester thereof in combination with prosulfocarb are used to control CHEAL, GALAP, KCHSC, PAPRH, SASKR, SINAR and STEME.

In certain embodiments of the compositions and methods described herein, the compound of formula (I) or salt or ester thereof is used in combination with pyroxasulfone. With regard to the compositions, in some embodiments, the weight ratio of the compound of formula (I) or salt or ester thereof to pyroxasulfone is within the range of from about 1:200 to about 12:1. In certain embodiments, the weight ratio of the compound of formula (I) or salt or ester thereof to pyroxasulfone is within the range of from about 1:15 to about 1:1. In certain embodiments, the compositions comprise the compound of formula (I) or its benzyl or n-butyl ester and pyroxasulfone. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 27 grams active ingredient per hectare (gai/ha) to about 600 gai/ha based on the total amount of active ingredients in the composition. In certain embodiments, the composition is applied at an application rate of from about 37 grams acid active ingredient per hectare (gai/ha) to about 150 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and pyroxasulfone, e.g., sequentially or simultaneously. In some embodiments, the pyroxasulfone is applied at a rate from about 500 gai/ha to about 4000 gai/ha and the compound of formula (I) of salt or ester thereof is applied at a rate from about 2 gae/ha to about 300 gae/ha. In some embodiments, the pyroxasulfone is applied at a rate from about 30 gai/ha to about 120 gai/ha and the compound of formula (I) of salt or ester thereof is applied at a rate from about 8 gae/ha to about 32 gae/ha. In certain embodiments, the methods utilize the compound of formula (I) or its benzyl or n-butyl ester and pyroxasulfone. In certain embodiments, the methods and compositions utilizing the compound of formula (I) or salt or ester thereof in combination with pyroxasulfone are used to control ECHCG or BRAPP.

In certain embodiments of the compositions and methods described herein, the compound of formula (I) or salt or ester thereof is used in combination with thenylchlor. With regard to the compositions, in some embodiments, the weight ratio of the compound of formula (I) or salt or ester thereof to thenylchlor is within the range of from about 1:375 to about 4:1. In certain embodiments, the weight ratio of the compound of formula (I) or salt or ester thereof to thenylchlor is within the range of from about 1:341 to about 1:1. In certain embodiments, the weight ratio of the compound of formula (I) or salt or ester thereof to thenylchlor is within the range of from about 1:34 to about 1:1. In certain embodiments, the compositions comprise the compound of formula (I) or its benzyl or n-butyl ester and thenylchlor. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 77 grams active ingredient per hectare (gai/ha) to about 1050 gai/ha based on the total amount of active ingredients in the composition. In certain embodiments, the composition is applied at an application rate of from about 79 grams acid active ingredient per hectare (gai/ha) to about 800 gai/ha based on the total amount of active ingredients in the composition. In certain embodiments, the composition is applied at an application rate of from about 143 grams acid active ingredient per hectare (gai/ha) to about 302 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and thenylchlor, e.g., sequentially or simultaneously. In some embodiments, the thenylchlor is applied at a rate from about 75 gai/ha to about 750 gai/ha and the compound of formula (I) of salt or ester thereof is applied at a rate from about 2 gae/ha to about 300 gae/ha. In some embodiments, the thenylchlor is applied at a rate from about 135 gai/ha to about 270 gai/ha and the compound of formula (I) of salt or ester thereof is applied at a rate from about 8 gae/ha to about 32 gae/ha. In certain embodiments, the methods utilize the compound of formula (I) or its benzyl or n-butyl ester and thenylchlor. In certain embodiments, the methods and compositions utilizing the compound of formula (I) or salt or ester thereof in combination with thenychloror salt or ester thereof are used to control ECHOR and LEFCH.

In certain embodiments of the compositions and methods described herein, the compound of formula (I) or salt or ester thereof is used in combination with thiobencarb. With regard to the compositions, in some embodiments, the weight ratio of the compound of formula (I) or salt or ester thereof to thiobencarb is within the range of from about 1:2250 to about 1:4. In certain embodiments, the weight ratio of the compound of formula (I) or salt or ester thereof to thiobencarb is within the range of from about 1:511 to about 1:32. In certain embodiments, the weight ratio of the compound of formula (I) or salt or ester thereof to thiobencarb is within the range of from about 1:510 to about 1:17 In certain embodiments, the weight ratio of the compound of formula (I) or salt or ester thereof to thiobencarb is within the range of from about 1:1000 to about 1:16. In certain embodiments, the weight ratio of the compound of formula (I) or salt or ester thereof to thiobencarb is within the range of from about 1:511 to about 1:32. In certain embodiments, the compositions provided herein comprise the compound of formula (I) or its benzyl ester and thiobencarb. In one embodiment, the composition comprises the benzyl ester of the compound of formula (I) and thiobencarb, wherein the weight ratio of the benzyl ester of the compound of formula (I) to thiobencarb is about 1:511 to about 1:17. In one embodiment, the composition comprises the compound of formula (I) and thiobencarb, wherein the weight ratio of the compound of formula (I) to thiobencarb is about 1:511 to about 1:32. In one embodiment, the composition comprises the benzyl ester of the compound of formula (I) and thiobencarb, wherein the weight ratio of the benzyl ester of the compound of formula (I) to thiobencarb is about 1:511 to about 1:64. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 562 grams active ingredient per hectare (gai/ha) to about 4,800 gai/ha based on the total amount of active ingredients in the composition. In certain embodiments, the composition is applied at an application rate of from about 564 grams active ingredient per hectare (gai/ha) to about 2275 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and thiobencarb, e.g., sequentially or simultaneously. In some embodiments, the thiobencarb is applied at a rate from about 560 gai/ha to about 4500 gai/ha and the compound of formula (I) of salt or ester thereof is applied at a rate from about 2 gae/ha to about 300 gae/ha. In some embodiments, the thiobencarb is applied at a rate from about 280 gai/ha to about 5000 gai/ha and the compound of formula (I) of salt or ester thereof is applied at a rate from about 2 g acid equivalent per hectare (gae/ha) to about 45 gae/ha. In some embodiments, the thiobencarb is applied at a rate from about 560 gai/ha to about 2240 gai/ha and the compound of formula (I) of salt or ester thereof is applied at a rate from about 4.38 g acid equivalent per hectare (gae/ha) to about 17.5 gae/ha. In certain embodiments, the methods utilize the compound of formula (I), or its benzyl ester and thiobencarb. In one embodiment, the methods utilize the compound of formula (I) and thiobencarb, wherein the compound of formula (I) is applied at a rate of from about 4.38 g acid equivalent per hectare (gae/ha) to about 17.5 gae/ha, and thiobencarb is applied at a rate of about 560 gai/ha to about 2240 gai/ha. In one embodiment, the methods utilize the compound of formula (I) and thiobencarb, wherein the compound of formula (I) is applied at a rate of from about 4.38 g acid equivalent per hectare (gae/ha) to about 35 gae/ha, and thiobencarb is applied at a rate of about 560 gai/ha to about 2240 gai/ha. In one embodiment, the methods utilize the benzyl ester of the compound of formula (I) and thiobencarb, wherein the benzyl ester of the compound of formula (I) is applied at a rate of from about 4.83 g acid equivalent per hectare (gae/ha) to about 35 gae/ha, and thiobencarb is applied at a rate of about 560 gai/ha to about 2240 gai/ha. In certain embodiments, the methods and compositions utilizing the compound of formula (I) or salt or ester thereof in combination with thiobencarb or salt or ester thereof are used to control ECHOR, CYPRO, DIGSA, CYPIR, ISCRU or ECHCO.

The components of the mixtures described herein can be applied either separately or as part of a multipart herbicidal system.

The mixtures described herein can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the compositions and methods described herein include, but are not limited to: 4-CPA; 4-CPB; 4-CPP; 2,4-D; 2,4-D choline salt, 2,4-D esters and amines, 2,4-DB; 3,4-DA; 3,4-DB; 2,4-DEB; 2,4-DEP; 3,4-DP; 2,3,6-TBA; 2,4,5-T; 2,4,5-TB; acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anisuron, asulam, atraton, atrazine, azafenidin, azimsulfuron, aziprotryne, barban, BCPC, beflubutamid, benazolin, bencarbazone, benfluralin, bensulfuron-methyl, bensulide, benthiocarb, bentazon-sodium, benzadox, benzfendizone, benzipram, benzobicyclon, benzofenap, benzofluor, benzoylprop, benzthiazuron, bialaphos, bicyclopyrone, bifenox, bilanafos, bispyribac-sodium, borax, bromacil, bromobonil, bromobutide, bromofenoxim, bromoxynil, brompyrazon, butafenacil, butamifos, butenachlor, buthidazole, buthiuron, butralin, butroxydim, buturon, butylate, cacodylic acid, calcium chlorate, calcium cyanamide, cambendichlor, carbasulam, carbetamide, carboxazole chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclopyrimorate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop-methyl, diclosulam, diethamquat, diethatyl, difenopenten, difenoxuron, difenzoquat, diflufenican, diflufenzopyr, dimefuron, dimepiperate, dimethachlor, dimethametryn, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenteracol, fenthiaprop, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, fluoroxypyr-meptyl, flurtamone, fluthiacet, fomesafen, foramsulfuron, fosamine, fumiclorac, furyloxyfen, glufosinate, glufosinate-ammonium, glufosinate-P-ammonium, glyphosate salts and esters, halauxifen, halauxifen-methyl, halosafen, halosulfuron-methyl, haloxydine, haloxyfop-methyl, haloxyfop-P-methyl, hexachloroacetone, hexaflurate, hexazinone, imazamethabenz, imazamox, imazapic, imazapyr, imazaquin, imazosulfuron, imazethapyr, indaziflam, iodobonil, iodomethane, iodosulfuron, iodosulfuron-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA esters and amines, MCPA-thioethyl, MCPB, mecoprop, mecoprop-P, medinoterb, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metosulam, metoxuron, metribuzin, metsulfuron, metsulfuron-methyl, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufen-ethyl, parafluoron, paraquat, pebulate, pelargonic acid, pendimethalin, penoxsulam, pentachlorophenol, pentanochlor, pentoxazone, perfluidone, phenisopham, phenmedipham, phenmedipham-ethyl, phenobenzuron, phenylmercury acetate, picloram, picolinafen, pinoxaden, piperophos, potassium arsenite, potassium azide, potassium cyanate, primisulfuron-methyl, procyazine, prodiamine, profluazol, profluralin, profoxydim, proglinazine, prohexadione-calcium, prometon, prometryn, pronamide, propachlor, propanil, propaquizafop, propazine, propham, propisochlor, propoxycarbazone, propyrisulfuron, propyzamide, prosulfalin, prosulfuron, proxan, prynachlor, pydanon, pyraclonil, pyraflufen-ethyl, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac, pyrimisulfan, pyrithiobac-sodium, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, SYN-523, TCA, tebutam, tebuthiuron, tefuryltrione, tembotrione, tepraloxydim, terbacil, terbucarb, terbuchlor, terbumeton, terbuthylazine, terbutryn, tetrafluoron, thiazafluoron, thiazopyr, thidiazimin, thidiazuron, thiencarbazone-methyl, thifensulfuron, thifensulfurn-methyl, tiocarbazil, tioclorim, topramezone, tralkoxydim, triafamone, tri-allate, triasulfuron, triaziflam, tribenuron, tribenuron-methyl, tricamba, triclopyr choline salt, triclopyr esters and salts, tridiphane, trietazine, trifloxysulfuron, trifluralin, triflusulfuron, trifop, trifopsime, trihydroxytriazine, trimeturon, tripropindan, tritac tritosulfuron, vernolate, xylachlor and salts, esters, optically active isomers and mixtures thereof.

The compositions and methods described herein, can further be used in conjunction with glyphosate, 5-enolpyruvylshikimate-3-phosphate (EPSP) synthase inhibitors, glufosinate, glutamine synthetase inhibitors, dicamba, phenoxy auxins, pyridyloxy auxins, synthetic auxins, auxin transport inhibitors, aryloxyphenoxypropionates, cyclohexanediones, phenylpyrazolines, acetyl CoA carboxylase (ACCase) inhibitors, imidazolinones, sulfonylureas, pyrimidinylthiobenzoates, triazolopyrimidines, sulfonylaminocarbonyltriazolinones, acetolactate synthase (ALS) or acetohydroxy acid synthase (AHAS) inhibitors, 4-hydroxyphenyl-pyruvate dioxygenase (HPPD) inhibitors, phytoene desaturase inhibitors, carotenoid biosynthesis inhibitors, protoporphyrinogen oxidase (PPO) inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil on glyphosate-tolerant, EPSP synthase inhibitor-tolerant, glufosinate-tolerant, glutamine synthetase inhibitor-tolerant, dicamba-tolerant, phenoxy auxin-tolerant, pyridyloxy auxin-tolerant, auxin-tolerant, auxin transport inhibitor-tolerant, aryloxyphenoxypropionate-tolerant, cyclohexanedione-tolerant, phenylpyrazoline-tolerant, ACCase-tolerant, imidazolinone-tolerant, sulfonylurea-tolerant, pyrimidinylthiobenzoate-tolerant, triazolopyrimidine-tolerant, sulfonylaminocarbonyltriazolinone-tolerant, ALS- or AHAS-tolerant, HPPD-tolerant, phytoene desaturase inhibitor-tolerant, carotenoid biosynthesis inhibitor tolerant, PPO-tolerant, cellulose biosynthesis inhibitor-tolerant, mitosis inhibitor-tolerant, microtubule inhibitor-tolerant, very long chain fatty acid inhibitor-tolerant, fatty acid and lipid biosynthesis inhibitor-tolerant, photosystem I inhibitor-tolerant, photosystem II inhibitor-tolerant, triazine-tolerant, bromoxynil-tolerant, and crops possessing multiple or stacked traits conferring tolerance to multiple chemistries and/or multiple modes of action via single and/or multiple resistance mechanisms. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation, as a tank mix, or as a sequential application.

In some embodiments, the compositions described herein are employed in combination with one or more herbicide safeners, such as AD-67 (MON 4660), benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, jiecaowan, jiecaoxi, mefenpyr-diethyl, mephenate, naphthalic anhydride (NA), oxabetrinil, R29148 and N-phenyl-sulfonylbenzoic acid amides, to enhance their selectivity. In some embodiments, the safeners are employed in rice, cereal, corn, or maize settings. In some embodiments, the safener is cloquintocet or an ester or salt thereof. In certain embodiments, cloquintocet is utilized to antagonize harmful effects of the compositions on rice and cereals. In some embodiments, the safener is cloquintocet (mexyl).

In some embodiments, the compositions described herein are employed in combination with one or more plant growth regulators, such as 2,3,5-tri-iodobenzoic acid, IAA, IBA, naphthaleneacetamide, α-naphthaleneacetic acids, benzyladenine, 4-hydroxyphenethyl alcohol, kinetin, zeatin, endothal, ethephon, pentachlorophenol, thidiazuron, tribufos, aviglycine, maleic hydrazide, gibberellins, gibberellic acid, abscisic acid, ancymidol, fosamine, glyphosine, isopyrimol, jasmonic acid, maleic hydrazide, mepiquat, 2,3,5-tri-iodobenzoic acid, morphactins, dichlorflurenol, flurprimidol, mefluidide, paclobutrazol, tetcyclacis, uniconazole, brassinolide, brassinolide-ethyl, cycloheximide, ethylene, methasulfocarb, prohexadione, triapenthenol and trinexapac.

In some embodiments, the plant growth regulators are employed in one or more crops or settings, such as rice, cereal crops, corn, maize, broadleaf crops, oilseed rape/canola, turf, pineapple, sugarcane, sunflower, pastures, grasslands, rangelands, fallowland, turf, tree and vine orchards, plantation crops, vegetables, and non-crop (ornamentals) settings. In some embodiments, the plant growth regulator is mixed with the compound of formula (I), or mixed with the compound of formula (I) and VLCFA inhibitors or fatty acid/lipid synthesis inhibitors to cause a preferentially advantageous effect on plants.

In some embodiments, compositions provided herein further comprise at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or tank mixed.

Suitable agricultural adjuvants and carriers include, but are not limited to, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. The organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. In certain embodiments, Water is the carrier for the dilution of concentrates.

Suitable solid carriers include but are not limited to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

In some embodiments, the compositions described herein further comprise one or more surface-active agents. In some embodiments, such surface-active agents are employed in both solid and liquid compositions, and in certain embodiments those designed to be diluted with carrier before application. The surface-active agents can be anionic, cationic or nonionic in character and can be employed as emulsifying agents, wetting agents, suspending agents, or for other purposes. Surfactants which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Surface-active agents include, but are not limited to salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkyl-naphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, and in certain embodiments, methyl esters.

In some embodiments, these materials, such as vegetable or seed oils and their esters, can be used interchangeably as an agricultural adjuvant, as a liquid carrier or as a surface active agent.

Other exemplary additives for use in the compositions provided herein include but are not limited to compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

In some embodiments, the concentration of the active ingredients in the compositions described herein is from about 0.0005 to 98 percent by weight. In some embodiments, the concentration is from about 0.0006 to 90 percent by weight. In compositions designed to be employed as concentrates, the active ingredients, in certain embodiments, are present in a concentration from about 0.1 to 98 weight percent, and in certain embodiment's about 0.5 to 90 weight percent. Such compositions are, in certain embodiments, diluted with an inert carrier, such as water, before application. The diluted compositions usually applied to weeds or the locus of weeds contain, in certain embodiments, about 0.0006 to 10.0 weight percent active ingredient and in certain embodiments contain about 0.01 to 7.0 weight percent.

The present compositions can be applied to weeds or their locus by the use of conventional ground or aerial dusters, sprayers, and granule applicators, by addition to irrigation or paddy water, and by other conventional means known to those skilled in the art.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

Results in Examples I, II, III, and IV are greenhouse trial results.

Example I

Evaluation of Postemergence Foliar-Applied Herbicidal Mixtures for Weed Control in Direct Seeded Rice Seeds or nutlets of the desired test plant species were planted in a soil matrix prepared by mixing a loam or sandy loam soil (e.g., 28.6 percent silt, 18.8 percent clay, and 52.6 percent sand, with a pH of about 5.8 and an organic matter content of about 1.8 percent) and calcareous grit in an 80 to 20 ratio. The soil matrix was contained in plastic pots with a volume of 1 quart and a surface area of 83.6 square centimeters ($cm^2$). When required to ensure good germination and healthy plants, a fungicide treatment and/or other chemical or physical treatment was applied. The plants were grown for 8-22 days in a greenhouse with an approximate 14 hr photoperiod which was maintained at about 29° C. during the day and 26° C. during the night. Nutrients (Peters Excel® 15-5-15 5-Ca 2-Mg and iron chelate) were applied in the irrigation solution as needed and water was added on a regular basis. Supplemental lighting was provided with overhead metal halide 1000-Watt lamps as necessary. The plants were employed for testing when they reached the first through fourth true leaf stage.

Treatments consisted of the acid or esters of 4-amino-3-chloro-5-fluoro-6-(4-chloro-2-fluoro-3-methoxy-phenyl)pyridine-2-carboxylic acid (Compound A), each formulated as an SC (suspension concentrate), and various herbicidal components alone and in combination. Forms of compound A were applied on an acid equivalent basis.

Forms of compound A (compound of formula I) tested include:

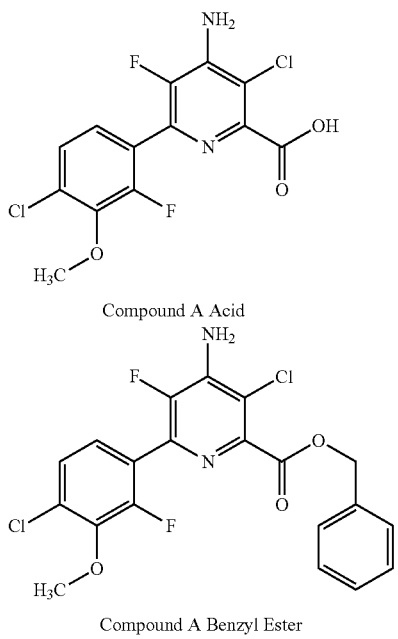

Compound A Acid

Compound A Benzyl Ester

Other herbicidal components were applied on an active ingredient basis and included very long chain fatty acid (VLCFA) synthesis-inhibiting and fatty acid/lipid synthesis-inhibiting herbicides acetochlor (technical grade material), acetochlor+dichlormid formulated as Topnotch®, pretilachlor (technical grade material), butachlor formulated as Butachlor EC, fentrazamide formulated as Fentrazamide EC, thiobencarb formulated as Bolero® 8EC, cafenstrole formulated as Himeadow® WP or Lapost® Flowable, benfuresate formulated as Full Shot®, dimethenamid-P formulated as Outlook®, indanofan (technical grade material), flufenacet formulated as Define® DF, mefenacet (technical grade material), S-metolachlor formulated as Dual® II Magnum, pethoxamid formulated as Successor® 600, and pyroxasulfone (technical grade material).

Treatment requirements were calculated based upon the rates being tested, the concentration of active ingredient or acid equivalent in the formulation, and a 12 mL application volume at a rate of 187 L/ha.

For treatments comprised of formulated compounds, measured amounts of compounds were placed individually in 25 mL glass vials and diluted in a volume of 1.25% (v/v) Agri-Dex® crop oil concentrated to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of 10 mL of an aqueous mixture of 1.25% (v/v) crop oil concentrate so that the final spray solutions contained 1.25+/−0.05% (v/v) crop oil concentrate.

For treatments comprised of technical compounds, weighed amounts can be placed individually in 25 mL glass vials and dissolved in a volume of 97:3 v/v acetone/DMSO to obtain 12× stock solutions. If a test compound does not dissolve readily, the mixture can be warmed and/or sonicated. Application solutions can be prepared by adding an appropriate amount of each stock solution (e.g., 1 mL) and diluted to the appropriate final concentrations with the addition of 10 mL of an aqueous mixture of 1.5% (v/v) crop oil concentrate so that the final spray solutions contain 1.25% (v/v) crop oil concentrate. When technical materials are used, the concentrated stock solutions can be added to the spray solutions so that the final acetone and DMSO concentrations of the application solutions are 16.2% and 0.5%, respectively.

For treatments comprised of formulated and technical compounds, weighed amounts of the technical materials were placed individually in 25 mL glass vials and dissolved in a volume of 97:3 v/v acetone/DMSO to obtain 12× stock solutions, and measured amounts of the formulated compounds were placed individually in 25 mL glass vials and diluted in a volume of 1.5% (v/v) crop oil concentrate or water to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of an appropriate amount of an aqueous mixture of 1.5% (v/v) crop oil concentrate so that the final spray solutions contained 1.25% (v/v) crop oil concentrate. As required, additional water and/or 97:3 v/v acetone/DMSO was added to individual application solutions so that the final acetone and DMSO concentrations of the application solutions being compared were 8.1% and 0.25%, respectively.

All stock solutions and applications solutions were visually inspected for compound compatibility prior to application. Spray solutions were applied to the plant material with an overhead Mandel track sprayer equipped with a 8002E nozzles calibrated to deliver 187 L/ha over an application area of 0.503 m² at a spray height of 18 to 20 inches (46 to 50 cm) above average plant canopy height. Control plants were sprayed in the same manner with the solvent blank.

The treated plants and control plants were placed in a greenhouse as described above and watered by sub-irrigation to prevent wash-off of the test compounds. After approximately 3 weeks, the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture.

B=observed efficacy of active ingredient B at the same concentration as used in the mixture.

The compounds tested, application rates employed, plant species tested, and results are given in Tables 1-25.

TABLE 1

Synergistic Activity of Foliar-Applied Compound A Acid and Acetochlor Herbicidal Compositions on Control of Weeds Common to Rice Cropping Systems.

| Compound A Acid | Acetochlor | Visual Weed Control (%) - 20 DAA BRAPP | |
|---|---|---|---|
| gae/ha | gai/ha | Obs | Exp |
| 4.38 | 0 | 50 | — |
| 8.75 | 0 | 70 | — |
| 0 | 100 | 20 | — |
| 0 | 200 | 30 | — |
| 4.38 | 100 | 65 | 60 |
| 8.75 | 100 | 90 | 76 |
| 4.38 | 200 | 85 | 65 |
| 8.75 | 200 | 95 | 79 |

| Compound A Acid | Acetochlor | Visual Weed Control (%) - 20 DAA DIGSA | |
|---|---|---|---|
| gae/ha | gai/ha | Obs | Exp |
| 4.38 | 0 | 30 | — |
| 17.5 | 0 | 40 | — |
| 0 | 100 | 20 | — |
| 0 | 200 | 20 | — |
| 4.38 | 100 | 50 | 44 |
| 17.5 | 100 | 75 | 52 |
| 4.38 | 200 | 60 | 44 |
| 17.5 | 200 | 80 | 52 |

TABLE 2

Synergistic Activity of Foliar-Applied Compound A Benzyl Ester and Acetochlor Herbicidal Compositions on Control of Weeds Common to Rice Cropping Systems.

| Compound A Benzyl Ester | Acetochlor | Visual Weed Control (%) - 20 DAA DIGSA | |
|---|---|---|---|
| gae/ha | gai/ha | Obs | Exp |
| 4.38 | 0 | 50 | — |
| 8.75 | 0 | 60 | — |
| 0 | 200 | 20 | — |
| 4.38 | 200 | 75 | 60 |
| 8.75 | 200 | 95 | 68 |

| Compound A Benzyl Ester | Acetochlor | Visual Weed Control (%) - 20 DAA ECHCG | |
|---|---|---|---|
| gae/ha | gai/ha | Obs | Exp |
| 4.38 | 0 | 70 | — |
| 8.75 | 0 | 70 | — |
| 0 | 50 | 0 | — |
| 0 | 100 | 10 | — |
| 4.38 | 50 | 85 | 70 |
| 8.75 | 50 | 90 | 70 |
| 4.38 | 100 | 90 | 73 |
| 8.75 | 100 | 90 | 73 |

TABLE 3

Synergistic Activity of Foliar-Applied Compound A Acid and Acetochlor + Dichlormid Herbicidal Compositions on Control of Weeds Common to Rice Cropping Systems.

| Compound A Acid | Acetochlor + dichlormid | Visual Weed Control (%) - 20 DAA ECHCG | |
|---|---|---|---|
| gae/ha | gai/ha* | Obs | Exp |
| 4.38 | 0 | 60 | — |
| 0 | 50 | 0 | — |
| 0 | 100 | 40 | — |
| 0 | 200 | 80 | — |
| 4.38 | 50 | 80 | 60 |
| 4.38 | 100 | 95 | 76 |
| 4.38 | 200 | 95 | 92 |

| Compound A Acid | Acetochlor + dichlormid | Visual Weed Control (%) - 20 DAA LEFCH | |
|---|---|---|---|
| gae/ha | gai/ha* | Obs | Exp |
| 4.38 | 0 | 0 | — |
| 8.75 | 0 | 30 | — |
| 17.5 | 0 | 30 | — |
| 0 | 50 | 0 | — |
| 0 | 100 | 0 | — |
| 0 | 200 | 40 | — |
| 4.38 | 50 | 60 | 0 |
| 8.75 | 50 | 65 | 30 |
| 17.5 | 50 | 60 | 30 |
| 4.38 | 100 | 55 | 0 |
| 8.75 | 100 | 55 | 30 |
| 17.5 | 100 | 70 | 30 |
| 4.38 | 200 | 60 | 40 |
| 8.75 | 200 | 70 | 58 |
| 17.5 | 200 | 65 | 58 |

*gai/ha refers to active ingredient of acetachlor.

TABLE 4

Synergistic Activity of Foliar-Applied Compound A Benzyl Ester and Acetochlor + Dichlormid Herbicidal Compositions on Control of Weeds Common to Rice Cropping Systems.

| Compound A Benzyl Ester | Acetochlor + dichlormid | Visual Weed Control (%) - 20 DAA DIGSA | |
|---|---|---|---|
| gae/ha | gai/ha* | Obs | Exp |
| 4.38 | 0 | 40 | — |
| 8.75 | 0 | 40 | — |
| 0 | 200 | 40 | — |
| 4.38 | 200 | 85 | 64 |
| 8.75 | 200 | 75 | 64 |

| Compound A Benzyl Ester | Acetochlor + dichlormid | Visual Weed Control (%) - 20 DAA LEFCH | |
|---|---|---|---|
| gae/ha | gai/ha* | Obs | Exp |
| 4.38 | 0 | 15 | — |
| 8.75 | 0 | 30 | — |
| 17.5 | 0 | 50 | — |
| 0 | 50 | 0 | — |
| 0 | 100 | 0 | — |
| 0 | 200 | 40 | — |
| 4.38 | 50 | 50 | 15 |
| 8.75 | 50 | 60 | 30 |
| 17.5 | 50 | 70 | 50 |

TABLE 4-continued

Synergistic Activity of Foliar-Applied Compound A Benzyl Ester and Acetochlor + Dichlormid Herbicidal Compositions on Control of Weeds Common to Rice Cropping Systems.

| | | | |
|---|---|---|---|
| 4.38 | 100 | 30 | 15 |
| 8.75 | 100 | 45 | 30 |
| 17.5 | 100 | 50 | 50 |
| 4.38 | 200 | 65 | 49 |
| 8.75 | 200 | 70 | 58 |
| 17.5 | 200 | 75 | 70 |

*gai/ha refers to active ingredient of acetchlor.

TABLE 5

Synergistic Activity of Foliar-Applied Compound A Acid and Pretilachlor Herbicidal Compositions on Weed Control in a Rice Cropping System.

| Compound A Acid | Pretilachlor | Visual Weed Control (%) - 20 DAA | | | |
|---|---|---|---|---|---|
| | | BRAPP | | ECHCO | |
| gae/ha | gai/ha | Obs | Exp | Obs | Exp |
| 4.38 | 0 | 50 | — | 65 | — |
| 8.75 | 0 | 70 | — | 85 | — |
| 0 | 37.5 | 0 | — | 0 | — |
| 0 | 75 | 0 | — | 0 | — |
| 0 | 150 | 0 | — | 0 | — |
| 4.38 | 37.5 | 65 | 50 | 95 | 65 |
| 8.75 | 37.5 | 80 | 70 | 90 | 85 |
| 4.38 | 75 | 65 | 50 | 85 | 65 |
| 8.75 | 75 | 70 | 70 | 95 | 85 |
| 4.38 | 150 | 70 | 50 | 95 | 65 |
| 8.75 | 150 | 90 | 70 | 90 | 85 |

| Compound A Acid | Pretilachlor | Visual Weed Control (%) - 20 DAA DIGSA | |
|---|---|---|---|
| gae/ha | gai/ha | Obs | Exp |
| 4.38 | 0 | 30 | — |
| 17.5 | 0 | 40 | — |
| 0 | 37.5 | 0 | — |
| 0 | 75 | 0 | — |
| 0 | 150 | 0 | — |
| 4.38 | 37.5 | 50 | 30 |
| 17.5 | 37.5 | 50 | 40 |
| 4.38 | 75 | 40 | 30 |
| 17.5 | 75 | 85 | 40 |
| 4.38 | 150 | 50 | 30 |
| 17.5 | 150 | 75 | 40 |

| Compound A Acid | Pretilachlor | Visual Weed Control (%) - 20 DAA CYPIR | |
|---|---|---|---|
| gae/ha | gai/ha | Obs | Exp |
| 4.38 | 0 | 40 | — |
| 0 | 37.5 | 0 | — |
| 0 | 75 | 0 | — |
| 0 | 150 | 0 | — |
| 4.38 | 37.5 | 100 | 40 |
| 4.38 | 75 | 99 | 40 |
| 4.38 | 150 | 100 | 40 |

TABLE 6

Synergistic Activity of Foliar-Applied Compound A Benzyl Ester and Pretilachlor Herbicidal Compositions on Weed Control in a Rice Cropping System.

| Compound A Benzyl Ester | Pretilachlor | Visual Weed Control (%) - 20 DAA DIGSA | |
|---|---|---|---|
| gae/ha | gai/ha | Obs | Exp |
| 4.38 | 0 | 50 | — |
| 8.75 | 0 | 60 | — |
| 0 | 75 | 0 | — |
| 0 | 150 | 0 | — |
| 4.38 | 75 | 80 | 50 |
| 8.75 | 75 | 75 | 60 |
| 4.38 | 150 | 50 | 50 |
| 8.75 | 150 | 75 | 60 |

| Compound A Benzyl Ester | Pretilachlor | Visual Weed Control (%) - 20 DAA | | | |
|---|---|---|---|---|---|
| | | ECHCO | | ECHCG | |
| gae/ha | gai/ha | Obs | Exp | Obs | Exp |
| 4.38 | 0 | 60 | — | 70 | — |
| 8.75 | 0 | 85 | — | 70 | — |
| 0 | 37.5 | 0 | — | 10 | — |
| 0 | 75 | 0 | — | 10 | — |
| 0 | 150 | 0 | — | 0 | — |
| 4.38 | 37.5 | 80 | 60 | 80 | 73 |
| 8.75 | 37.5 | 95 | 85 | 95 | 73 |
| 4.38 | 75 | 80 | 60 | 85 | 73 |
| 8.75 | 75 | 95 | 85 | 99 | 73 |
| 4.38 | 150 | 90 | 60 | 80 | 70 |
| 8.75 | 150 | 90 | 85 | 85 | 70 |

| Compound A Benzyl Ester | Pretilachlor | Visual Weed Control (%) - 20 DAA CYPIR | |
|---|---|---|---|
| gae/ha | gai/ha | Obs | Exp |
| 4.38 | 0 | 80 | — |
| 0 | 37.5 | 0 | — |
| 0 | 75 | 0 | — |
| 4.38 | 37.5 | 95 | 80 |
| 4.38 | 75 | 100 | 80 |

TABLE 7

Synergistic Activity of Foliar-Applied Compound A Acid and Butachlor Herbicidal Compositions on Weed Control in a Rice Cropping System.

| Compound A Acid | Butachlor | Visual Weed Control (%) - 20 DAA | | | |
|---|---|---|---|---|---|
| | | BRAPP | | ECHCG | |
| gae/ha | gai/ha | Obs | Exp | Obs | Exp |
| 4.38 | 0 | 60 | — | 50 | — |
| 0 | 112.5 | 0 | — | 0 | — |
| 0 | 225 | 0 | — | 0 | — |
| 0 | 450 | 0 | — | 0 | — |
| 4.38 | 112.5 | 75 | 60 | 90 | 50 |
| 4.38 | 225 | 65 | 60 | 85 | 50 |
| 4.38 | 450 | 80 | 60 | 85 | 50 |

TABLE 7-continued

Synergistic Activity of Foliar-Applied Compound
A Acid and Butachlor Herbicidal Compositions
on Weed Control in a Rice Cropping System.

| Compound A Acid | Butachlor | Visual Weed Control (%) - 20 DAA ECHCO | |
|---|---|---|---|
| gae/ha | gai/ha | Obs | Exp |
| 4.38 | 0 | 40 | — |
| 8.75 | 0 | 60 | — |
| 0 | 112.5 | 0 | — |
| 0 | 225 | 0 | — |
| 0 | 450 | 0 | — |
| 4.38 | 112.5 | 75 | 40 |
| 8.75 | 112.5 | 85 | 60 |
| 4.38 | 225 | 80 | 40 |
| 8.75 | 225 | 90 | 60 |
| 4.38 | 450 | 85 | 40 |
| 8.75 | 450 | 95 | 60 |

| Compound A Acid | Butachlor | Visual Weed Control (%) - 20 DAA LEFCH | |
|---|---|---|---|
| gae/ha | gai/ha | Obs | Exp |
| 4.38 | 0 | 0 | — |
| 8.75 | 0 | 10 | — |
| 17.5 | 0 | 30 | — |
| 0 | 112.5 | 0 | — |
| 0 | 225 | 0 | — |
| 0 | 450 | 0 | — |
| 4.38 | 112.5 | 10 | 0 |
| 8.75 | 112.5 | 20 | 10 |
| 17.5 | 112.5 | 65 | 30 |
| 4.38 | 225 | NT | 0 |
| 8.75 | 225 | 30 | 10 |
| 17.5 | 225 | 60 | 30 |
| 4.38 | 450 | 75 | 0 |
| 8.75 | 450 | 50 | 10 |
| 17.5 | 450 | 85 | 30 |

| Compound A Acid | Butachlor | Visual Weed Control (%) - 20 DAA IPOHE | |
|---|---|---|---|
| gae/ha | gai/ha | Obs | Exp |
| 4.38 | 0 | 0 | — |
| 8.75 | 0 | 20 | — |
| 0 | 112.5 | 20 | — |
| 0 | 450 | 30 | — |
| 4.38 | 112.5 | 20 | 20 |
| 8.75 | 112.5 | 50 | 36 |
| 4.38 | 450 | 80 | 30 |
| 8.75 | 450 | 50 | 44 |

TABLE 8

Synergistic Activity of Foliar-Applied Compound
A Benzyl and Butachlor Herbicidal Compositions
on Weed Control in a Rice Cropping System.

| Compound A Benzyl Ester | Butachlor | Visual Weed Control (%) - 20 DAA BRAPP | | ECHCO | |
|---|---|---|---|---|---|
| gae/ha | gai/ha | Obs | Exp | Obs | Exp |
| 4.38 | 0 | 60 | — | 60 | — |
| 8.75 | 0 | 65 | — | 70 | — |
| 0 | 112.5 | 0 | — | 0 | — |
| 0 | 225 | 0 | — | 0 | — |
| 0 | 450 | 0 | — | 0 | — |
| 4.38 | 112.5 | 80 | 60 | 70 | 60 |
| 8.75 | 112.5 | 85 | 65 | 85 | 70 |
| 4.38 | 225 | 65 | 60 | 80 | 60 |
| 8.75 | 225 | 80 | 65 | 85 | 70 |
| 4.38 | 450 | 70 | 60 | 80 | 60 |
| 8.75 | 450 | 95 | 65 | 80 | 70 |

| Compound A Benzyl Ester | Butachlor | Visual Weed Control (%) - 20 DAA LEFCH | |
|---|---|---|---|
| gae/ha | gai/ha | Obs | Exp |
| 4.38 | 0 | 0 | — |
| 8.75 | 0 | 10 | — |
| 17.5 | 0 | 25 | — |
| 0 | 112.5 | 0 | — |
| 0 | 225 | 0 | — |
| 0 | 450 | 0 | — |
| 4.38 | 112.5 | 20 | 0 |
| 8.75 | 112.5 | 45 | 10 |
| 17.5 | 112.5 | 40 | 25 |
| 4.38 | 225 | 20 | 0 |
| 8.75 | 225 | 30 | 10 |
| 17.5 | 225 | 40 | 25 |
| 4.38 | 450 | 30 | 0 |
| 8.75 | 450 | 30 | 10 |
| 17.5 | 450 | 45 | 25 |

| Compound A Benzyl Ester | Butachlor | Visual Weed Control (%) - 20 DAA IPOHE | |
|---|---|---|---|
| gae/ha | gai/ha | Obs | Exp |
| 4.38 | 0 | 10 | — |
| 8.75 | 0 | 15 | — |
| 17.5 | 0 | 25 | — |
| 0 | 112.5 | 20 | — |
| 0 | 450 | 30 | — |
| 4.38 | 112.5 | 60 | 28 |
| 8.75 | 112.5 | 25 | 32 |
| 17.5 | 112.5 | 80 | 40 |
| 4.38 | 450 | 70 | 37 |
| 8.75 | 450 | 70 | 41 |
| 17.5 | 450 | 25 | 48 |

TABLE 9

Synergistic Activity of Foliar-Applied Compound
A Acid and Fentrazamide Herbicidal Compositions
on Weed Control in a Rice Cropping System.

| Compound A Acid | Fentrazamide | Visual Weed Control (%) - 20 DAA BRAPP | |
|---|---|---|---|
| gae/ha | gai/ha | Obs | Exp |
| 4.38 | 0 | 75 | — |
| 8.75 | 0 | 80 | — |
| 0 | 16.88 | 0 | — |
| 0 | 33.75 | 0 | — |
| 0 | 67.5 | 55 | — |
| 4.38 | 16.88 | 90 | 75 |
| 8.75 | 16.88 | 90 | 80 |
| 4.38 | 33.75 | 90 | 75 |
| 8.75 | 33.75 | 95 | 80 |
| 4.38 | 67.5 | 95 | 89 |
| 8.75 | 67.5 | 99 | 91 |

TABLE 9-continued

Synergistic Activity of Foliar-Applied Compound A Acid and Fentrazamide Herbicidal Compositions on Weed Control in a Rice Cropping System.

| Compound A Acid | Fentrazamide | Visual Weed Control (%) - 20 DAA | | | |
|---|---|---|---|---|---|
| | | ECHCG | | ECHCO | |
| gae/ha | gai/ha | Obs | Exp | Obs | Exp |
| 4.38 | 0 | 60 | — | 70 | — |
| 0 | 16.88 | 0 | — | 0 | — |
| 0 | 33.75 | 0 | — | 15 | — |
| 0 | 67.5 | 20 | — | 10 | — |
| 4.38 | 16.88 | 90 | 60 | 95 | 70 |
| 4.38 | 33.75 | 90 | 60 | 95 | 75 |
| 4.38 | 67.5 | 90 | 68 | 95 | 73 |

| Compound A Acid | Fentrazamide | Visual Weed Control (%) - 20 DAA LEFCH | |
|---|---|---|---|
| gae/ha | gai/ha | Obs | Exp |
| 4.38 | 0 | 15 | — |
| 8.75 | 0 | 30 | — |
| 17.5 | 0 | 50 | — |
| 0 | 33.75 | 0 | — |
| 0 | 67.5 | 0 | — |
| 4.38 | 33.75 | 10 | 15 |
| 8.75 | 33.75 | 50 | 30 |
| 17.5 | 33.75 | 60 | 50 |
| 4.38 | 67.5 | 30 | 15 |
| 8.75 | 67.5 | 40 | 30 |
| 17.5 | 67.5 | 65 | 50 |

TABLE 10

Synergistic Activity of Foliar-Applied Compound A Benzyl Ester and Fentrazamide Herbicidal Compositions on Weed Control in a Rice Cropping System.

| Compound A Benzyl Ester | Fentrazamide | Visual Weed Control (%) - 20 DAA DIGSA | |
|---|---|---|---|
| gae/ha | gai/ha | Obs | Exp |
| 8.75 | 0 | 30 | — |
| 17.5 | 0 | 30 | — |
| 0 | 33.75 | 0 | — |
| 0 | 67.5 | 30 | — |
| 8.75 | 33.75 | 45 | 30 |
| 17.5 | 33.75 | 45 | 30 |
| 8.75 | 67.5 | 90 | 51 |
| 17.5 | 67.5 | 85 | 51 |

| Compound A Benzyl Ester | Fentrazamide | Visual Weed Control (%) - 20 DAA ECHCG | |
|---|---|---|---|
| gae/ha | gai/ha | Obs | Exp |
| 16 | 0 | 78 | — |
| 32 | 0 | 83 | — |
| 0 | 75 | 0 | — |
| 0 | 150 | 5 | — |
| 0 | 300 | 13 | — |
| 16 | 75 | 95 | 78 |
| 32 | 75 | 95 | 83 |
| 16 | 150 | 90 | 79 |
| 32 | 150 | 95 | 83 |
| 16 | 300 | 95 | 80 |
| 32 | 300 | 95 | 85 |

TABLE 11

Synergistic Activity of Foliar-Applied Compound A Acid and Thiobencarb Herbicidal Compositions on Weed Control in a Rice Cropping System.

| Compound A Acid | Thiobencarb | Visual Weed Control (%) - 20 DAA DIGSA | |
|---|---|---|---|
| gae/ha | gai/ha | Obs | Exp |
| 4.38 | 0 | 30 | — |
| 17.5 | 0 | 40 | — |
| 0 | 560 | 20 | — |
| 4.38 | 560 | 60 | 44 |
| 17.5 | 560 | 70 | 52 |

| Compound A Acid | Thiobencarb | Visual Weed Control (%) - 20 DAA CYPIR | |
|---|---|---|---|
| gae/ha | gai/ha | Obs | Exp |
| 4.38 | 0 | 40 | — |
| 0 | 560 | 0 | — |
| 0 | 1120 | 0 | — |
| 0 | 2240 | 0 | — |
| 4.38 | 560 | 70 | 40 |
| 4.38 | 1120 | 95 | 40 |
| 4.38 | 2240 | 95 | 40 |

TABLE 12

Synergistic Activity of Foliar-Applied Compound A Benzyl Ester and Thiobencarb Herbicidal Compositions on Weed Control in a Rice Cropping System.

| Compound A Benzyl Ester | Thiobencarb | Visual Weed Control (%) - 20 DAA ECHCO | |
|---|---|---|---|
| gae/ha | gai/ha | Obs | Exp |
| 4.38 | 0 | 60 | — |
| 8.75 | 0 | 85 | — |
| 0 | 560 | 45 | — |
| 0 | 1120 | 40 | — |
| 4.38 | 560 | 90 | 78 |
| 8.75 | 560 | 95 | 92 |
| 4.38 | 1120 | 90 | 76 |
| 8.75 | 1120 | 95 | 91 |

| Compound A Benzyl Ester | Thiobencarb | Visual Weed Control (%) - 21 DAA ISCRU | |
|---|---|---|---|
| gae/ha | gai/ha | Obs | Exp |
| 8 | 0 | 20 | — |
| 16 | 0 | 0 | — |
| 0 | 1120 | 0 | — |
| 0 | 2240 | 0 | — |
| 8 | 1120 | 0 | 20 |
| 16 | 1120 | 85 | 0 |
| 8 | 2240 | 100 | 20 |
| 16 | 2240 | 100 | 0 |

TABLE 13

Synergistic Activity of Foliar-Applied Compound A Acid and Cafenstrole (Himeadow ® WP) Herbicidal Compositions on Weed Control in a Rice Cropping System.

| Compound A Acid | Cafenstrole | Visual Weed Control (%) - 20 DAA ECHCG | |
|---|---|---|---|
| gae/ha | gai/ha | Obs | Exp |
| 4.38 | 0 | 50 | — |
| 0 | 26.25 | 10 | — |
| 0 | 52.5 | 15 | — |
| 0 | 105 | 15 | — |
| 4.38 | 26.25 | 65 | 55 |
| 4.38 | 52.5 | 70 | 58 |
| 4.38 | 105 | 70 | 58 |

| Compound A Acid | Cafenstrole | Visual Weed Control (%) - 20 DAA ECHCO | |
|---|---|---|---|
| gae/ha | gai/ha | Obs | Exp |
| 4.38 | 0 | 40 | — |
| 8.75 | 0 | 60 | — |
| 0 | 26.25 | 10 | — |
| 0 | 52.5 | 10 | — |
| 0 | 105 | 10 | — |
| 4.38 | 26.25 | 40 | 46 |
| 8.75 | 26.25 | 75 | 64 |
| 4.38 | 52.5 | 60 | 46 |
| 8.75 | 52.5 | 85 | 64 |
| 4.38 | 105 | 75 | 46 |
| 8.75 | 105 | 90 | 64 |

| Compound A Acid | Cafenstrole | Visual Weed Control (%) - 20 DAA LEFCH | |
|---|---|---|---|
| gae/ha | gai/ha | Obs | Exp |
| 4.38 | 0 | 0 | — |
| 8.75 | 0 | 10 | — |
| 17.5 | 0 | 30 | — |
| 0 | 52.5 | 0 | — |
| 0 | 105 | 0 | — |
| 4.38 | 52.5 | 30 | 0 |
| 8.75 | 52.5 | 20 | 10 |
| 17.5 | 52.5 | 45 | 30 |
| 4.38 | 105 | 45 | 0 |
| 8.75 | 105 | 30 | 10 |
| 17.5 | 105 | 30 | 30 |

| Compound A Acid | Cafenstrole | Visual Weed Control (%) - 20 DAA IPOHE | |
|---|---|---|---|
| gae/ha | gai/ha | Obs | Exp |
| 4.38 | 0 | 0 | — |
| 8.75 | 0 | 20 | — |
| 17.5 | 0 | 40 | — |
| 0 | 26.25 | 0 | — |
| 0 | 105 | 30 | — |
| 4.38 | 26.25 | 20 | 0 |
| 8.75 | 26.25 | 30 | 20 |
| 17.5 | 26.25 | 70 | 40 |
| 4.38 | 105 | 20 | 30 |
| 8.75 | 105 | 60 | 44 |
| 17.5 | 105 | 65 | 58 |

TABLE 14

Synergistic Activity of Foliar-Applied Compound A Acid and Cafenstrole (Lapost ® Flowable) Herbicidal Compositions on Weed Control in a Rice Cropping System.

| Compound A Acid | Cafenstrole | Visual Weed Control (%) - 21 DAA CYPIR | |
|---|---|---|---|
| gae/ha | gai/ha | Obs | Exp |
| 4.38 | 0 | 70 | — |
| 0 | 26.25 | 0 | — |
| 0 | 52.5 | 0 | — |
| 0 | 105 | 0 | — |
| 4.38 | 26.25 | 80 | 70 |
| 4.38 | 52.5 | 90 | 70 |
| 4.38 | 105 | 95 | 70 |

| Compound A Acid | Cafenstrole | Visual Weed Control (%) - 21 DAA | | | |
|---|---|---|---|---|---|
| | | ECHCG | | LEFCH | |
| gae/ha | gai/ha | Obs | Exp | Obs | Exp |
| 17.5 | 0 | 88 | — | 20 | — |
| 35 | 0 | 85 | — | 45 | — |
| 0 | 210 | 0 | — | 23 | — |
| 17.5 | 210 | 90 | 88 | 68 | 38 |
| 35 | 210 | 97 | 85 | 73 | 57 |

TABLE 15

Synergistic Activity of Foliar-Applied Compound A Benzyl Ester and Cafenstrole (Himeadow ® WP) Herbicidal Compositions on Weed Control in a Rice Cropping System.

| Compound A Benzyl Ester | Cafenstrole | Visual Weed Control (%) - 20 DAA BRAPP | |
|---|---|---|---|
| gae/ha | gai/ha | Obs | Exp |
| 4.38 | 0 | 60 | — |
| 8.75 | 0 | 65 | — |
| 0 | 26.25 | 0 | — |
| 0 | 52.5 | 0 | — |
| 0 | 105 | 0 | — |
| 4.38 | 26.25 | 65 | 60 |
| 8.75 | 26.25 | 85 | 65 |
| 4.38 | 52.5 | 70 | 60 |
| 8.75 | 52.5 | 85 | 65 |
| 4.38 | 105 | 75 | 60 |
| 8.75 | 105 | 75 | 65 |

| Compound A Benzyl Ester | Cafenstrole | Visual Weed Control (%) - 20 DAA LEFCH | |
|---|---|---|---|
| gae/ha | gai/ha | Obs | Exp |
| 4.38 | 0 | 0 | — |
| 8.75 | 0 | 10 | — |
| 17.5 | 0 | 25 | — |
| 0 | 26.25 | 0 | — |
| 0 | 52.5 | 0 | — |
| 0 | 105 | 0 | — |
| 4.38 | 26.25 | 20 | 0 |
| 8.75 | 26.25 | 30 | 10 |
| 17.5 | 26.25 | 35 | 25 |
| 4.38 | 52.5 | 25 | 0 |
| 8.75 | 52.5 | 20 | 10 |
| 17.5 | 52.5 | 35 | 25 |
| 4.38 | 105 | 20 | 0 |
| 8.75 | 105 | 25 | 10 |
| 17.5 | 105 | 50 | 25 |

TABLE 15-continued

Synergistic Activity of Foliar-Applied Compound A Benzyl Ester and Cafenstrole (Himeadow ® WP) Herbicidal Compositions on Weed Control in a Rice Cropping System.

| Compound A Benzyl Ester | Cafenstrole | Visual Weed Control (%) - 20 DAA IPOHE | |
|---|---|---|---|
| gae/ha | gai/ha | Obs | Exp |
| 17.5 | 0 | 25 | — |
| 0 | 26.25 | 0 | — |
| 0 | 105 | 30 | — |
| 17.5 | 26.25 | 50 | 25 |
| 17.5 | 105 | 90 | 48 |

TABLE 16

Synergistic Activity of Foliar-Applied Compound A Benzyl Ester and Cafenstrole (Lapost ® Flowable) Herbicidal Compositions on Weed Control in a Rice Cropping System.

| Compound A Benzyl Ester | Cafenstrole | Visual Weed Control (%) - 21 DAA IPOHE | |
|---|---|---|---|
| gae/ha | gai/ha | Obs | Exp |
| 4.38 | 0 | 0 | — |
| 8.75 | 0 | 10 | — |
| 17.5 | 0 | 30 | — |
| 0 | 26.25 | 0 | — |
| 4.38 | 26.25 | 20 | 0 |
| 8.75 | 26.25 | 40 | 10 |
| 17.5 | 26.25 | 45 | 30 |

| Compound A Benzyl Ester | Cafenstrole | Visual Weed Control (%) - 21 DAA IPOHE | |
|---|---|---|---|
| gae/ha | gai/ha | Obs | Exp |
| 17.5 | 0 | 10 | — |
| 0 | 210 | 10 | — |
| 17.5 | 210 | 30 | 19 |

| Compound A Benzyl Ester | Cafenstrole | Visual Weed Control (%) - 21 DAA SCPJU | |
|---|---|---|---|
| gae/ha | gai/ha | Obs | Exp |
| 4.38 | 0 | 40 | — |
| 0 | 26.25 | 0 | — |
| 0 | 52.5 | 0 | — |
| 0 | 105 | 0 | — |
| 4.38 | 26.25 | 100 | 40 |
| 4.38 | 52.5 | 100 | 40 |
| 4.38 | 105 | 100 | 40 |

TABLE 17

Synergistic Activity of Foliar-Applied Compound A Acid and Benfuresate Herbicidal Compositions on Weed Control in a Rice Cropping System.

| Compound A Acid | Benfuresate | Visual Weed Control (%) - 22 DAA | | | |
|---|---|---|---|---|---|
| | | ECHCG | | ECHCO | |
| gae/ha | gai/ha | Obs | Exp | Obs | Exp |
| 5.3 | 0 | 65 | — | 65 | — |
| 10.6 | 0 | 55 | — | 65 | — |
| 0 | 75 | 0 | — | 0 | — |
| 0 | 150 | 0 | — | 0 | — |
| 0 | 300 | 0 | — | 0 | — |
| 5.3 | 75 | 65 | 65 | 80 | 65 |
| 10.6 | 75 | 80 | 55 | 80 | 65 |
| 5.3 | 150 | 75 | 65 | 85 | 65 |
| 10.6 | 150 | 90 | 55 | 85 | 65 |
| 5.3 | 300 | 90 | 65 | 85 | 65 |
| 10.6 | 300 | 90 | 55 | 90 | 65 |

| Compound A Acid | Benfuresate | Visual Weed Control (%) - 22 DAA LEFCH | |
|---|---|---|---|
| gae/ha | gai/ha | Obs | Exp |
| 10.6 | 0 | 10 | — |
| 21.2 | 0 | 10 | — |
| 0 | 300 | 10 | — |
| 10.6 | 300 | 50 | 19 |
| 21.2 | 300 | 60 | 19 |

| Compound A Acid | Benfuresate | Visual Weed Control (%) - 22 DAA CYPIR | |
|---|---|---|---|
| gae/ha | gai/ha | Obs | Exp |
| 5.3 | 0 | 60 | — |
| 0 | 150 | 0 | — |
| 0 | 300 | 10 | — |
| 5.3 | 150 | 99 | 60 |
| 5.3 | 300 | 100 | 64 |

TABLE 18

Synergistic Activity of Foliar-Applied Compound A Benzyl Ester and Benfuresate Herbicidal Compositions on Weed Control in a Rice Cropping System.

| Compound A Benzyl Ester | Benfuresate | Visual Weed Control (%) - 22 DAA | | | |
|---|---|---|---|---|---|
| | | ECHCG | | ECHCO | |
| gae/ha | gai/ha | Obs | Exp | Obs | Exp |
| 5.3 | 0 | 40 | — | 30 | — |
| 10.6 | 0 | 60 | — | 55 | — |
| 0 | 75 | 0 | — | 0 | — |
| 0 | 150 | 0 | — | 0 | — |
| 0 | 300 | 0 | — | 0 | — |
| 5.3 | 75 | 40 | 40 | 55 | 30 |
| 10.6 | 75 | 55 | 60 | 60 | 55 |
| 5.3 | 150 | 65 | 40 | 85 | 30 |
| 10.6 | 150 | 85 | 60 | 70 | 55 |
| 5.3 | 300 | 85 | 40 | 75 | 30 |
| 10.6 | 300 | 90 | 60 | 85 | 55 |

| Compound A Benzyl Ester | Benfuresate | Visual Weed Control (%) - 21 DAA LEFCH | |
|---|---|---|---|
| gae/ha | gai/ha | Obs | Exp |
| 5.3 | 0 | 0 | — |
| 10.6 | 0 | 20 | — |
| 21.2 | 0 | 35 | — |
| 0 | 75 | 0 | — |
| 0 | 150 | 10 | — |
| 0 | 300 | 10 | — |
| 5.3 | 75 | 40 | 0 |
| 10.6 | 75 | 40 | 20 |

TABLE 18-continued

Synergistic Activity of Foliar-Applied Compound
A Benzyl Ester and Benfuresate Herbicidal Compositions
on Weed Control in a Rice Cropping System.

| | | | |
|---|---|---|---|
| 21.2 | 75 | 75 | 35 |
| 5.3 | 150 | 20 | 10 |
| 10.6 | 150 | 60 | 28 |
| 21.2 | 150 | 80 | 42 |
| 5.3 | 300 | 70 | 10 |
| 10.6 | 300 | 40 | 28 |
| 21.2 | 300 | 70 | 42 |

TABLE 19

Synergistic Activity of Foliar-Applied Compound A
Benzyl Ester and Dimethenamid-P Herbicidal Compositions
on Weed Control in a Rice Cropping System.

| Compound A Benzyl Ester | Dimethenamid-P | Visual Weed Control (%) - 20 DAA ECHCO | |
|---|---|---|---|
| gae/ha | gai/ha | Obs | Exp |
| 8 | 0 | 40 | |
| 16 | 0 | 60 | |
| 32 | 0 | 90 | |
| 0 | 275 | 70 | |
| 8 | 275 | 95 | 82 |
| 16 | 275 | 95 | 88 |
| 32 | 275 | 95 | 97 |

| Compound A Benzyl Ester | Dimethenamid-P | Visual Weed Control (%) - 20 DAA CYPES | |
|---|---|---|---|
| gae/ha | gai/ha | Obs | Exp |
| 8 | 0 | 0 | — |
| 16 | 0 | 75 | — |
| 0 | 275 | 0 | — |
| 8 | 275 | 100 | 0 |
| 16 | 275 | 100 | 75 |

TABLE 20

Synergistic Activity of Foliar-Applied Compound
A Benzyl Ester and Flufenacet Herbicidal Compositions
on Weed Control in a Rice Cropping System.

| Compound A Benzyl Ester | Flufenacet | Visual Weed Control (%) - 22 DAA BRAPP | |
|---|---|---|---|
| gae/ha | gai/ha | Obs | Exp |
| 8 | 0 | 60 | — |
| 16 | 0 | 60 | — |
| 32 | 0 | 90 | — |
| 0 | 187.5 | 10 | — |
| 0 | 375 | 20 | — |
| 0 | 750 | 40 | — |
| 8 | 187.5 | 80 | 64 |
| 16 | 187.5 | 90 | 64 |
| 32 | 187.5 | 90 | 91 |
| 8 | 375 | 75 | 68 |
| 16 | 375 | 90 | 68 |
| 32 | 375 | 95 | 92 |
| 8 | 750 | 80 | 76 |
| 16 | 750 | 95 | 76 |
| 32 | 750 | 95 | 94 |

TABLE 21

Synergistic Activity of Foliar-Applied Compound
A Benzyl Ester and Indanofan Herbicidal Compositions
on Weed Control in a Rice Cropping System.

| Compound A Benzyl Ester | Indanofan | Visual Weed Control (%) - 19 DAA ECHCO | |
|---|---|---|---|
| gae/ha | gai/ha | Obs | Exp |
| 8 | 0 | 65 | — |
| 0 | 37.5 | 0 | — |
| 0 | 75 | 0 | — |
| 0 | 150 | 35 | — |
| 8 | 37.5 | 80 | 65 |
| 8 | 75 | 85 | 65 |
| 8 | 150 | 90 | 77 |

| Compound A Benzyl Ester | Indanofan | Visual Weed Control (%) - 19 DAA LEFCH | |
|---|---|---|---|
| gae/ha | gai/ha | Obs | Exp |
| 16 | 0 | 45 | — |
| 32 | 0 | 50 | — |
| 0 | 37.5 | 0 | — |
| 0 | 75 | 0 | — |
| 16 | 37.5 | 60 | 45 |
| 32 | 37.5 | 50 | 50 |
| 16 | 75 | 65 | 45 |
| 32 | 75 | 60 | 50 |

TABLE 22

Synergistic Activity of Foliar-Applied Compound
A Benzyl Ester and Mefenacet Herbicidal Compositions
on Weed Control in a Rice Cropping System.

| Compound A Benzyl Ester | Mefenacet | Visual Weed Control (%) - 22 DAA BRAPP | |
|---|---|---|---|
| gae/ha | gai/ha | Obs | Exp |
| 8 | 0 | 65 | — |
| 16 | 0 | 80 | — |
| 32 | 0 | 85 | — |
| 0 | 50 | 0 | — |
| 0 | 100 | 0 | — |
| 0 | 200 | 0 | — |
| 8 | 50 | 80 | 65 |
| 16 | 50 | 90 | 80 |
| 32 | 50 | 85 | 85 |
| 8 | 100 | 75 | 65 |
| 16 | 100 | 90 | 80 |
| 32 | 100 | 99 | 85 |
| 8 | 200 | 80 | 65 |
| 16 | 200 | 90 | 80 |
| 32 | 200 | 90 | 85 |

| Compound A Benzyl Ester | Mefenacet | Visual Weed Control (%) - 22 DAA LEFCH | |
|---|---|---|---|
| gae/ha | gai/ha | Obs | Exp |
| 8 | 0 | 35 | — |
| 16 | 0 | 40 | — |
| 0 | 50 | 10 | — |
| 0 | 100 | 0 | — |
| 8 | 50 | 20 | 42 |
| 16 | 50 | 60 | 46 |
| 8 | 100 | 55 | 35 |
| 16 | 100 | 40 | 40 |

TABLE 22-continued

Synergistic Activity of Foliar-Applied Compound A Benzyl Ester and Mefenacet Herbicidal Compositions on Weed Control in a Rice Cropping System.

| Compound A Benzyl Ester | Mefenacet | Visual Weed Control (%) - 22 DAA CYPIR | |
|---|---|---|---|
| gae/ha | gai/ha | Obs | Exp |
| 16 | 0 | 60 | — |
| 0 | 100 | 0 | — |
| 0 | 200 | 20 | — |
| 16 | 100 | 100 | 60 |
| 16 | 200 | 100 | 68 |

TABLE 23

Synergistic Activity of Foliar-Applied Compound A Benzyl Ester and S-Metolachlor Herbicidal Compositions on Weed Control in a Rice Cropping System.

| Compound A Benzyl Ester | S-metolachlor | Visual Weed Control (%) - 20 DAA ECHCG | |
|---|---|---|---|
| gae/ha | gai/ha | Obs | Exp |
| 8 | 0 | 63 | — |
| 16 | 0 | 78 | — |
| 32 | 0 | 83 | — |
| 0 | 387.5 | 20 | — |
| 0 | 775 | 55 | — |
| 8 | 387.5 | 95 | 70 |
| 16 | 387.5 | 95 | 82 |
| 32 | 387.5 | 95 | 86 |
| 8 | 775 | 90 | 83 |
| 16 | 775 | 95 | 90 |
| 32 | 775 | 95 | 92 |

TABLE 24

Synergistic Activity of Foliar-Applied Compound A Benzyl Ester and Pethoxamid Herbicidal Compositions on Weed Control in a Rice Cropping System.

| Compound A Benzyl Ester | Pethoxamid | Visual Weed Control (%) - 21 DAA LEFCH | |
|---|---|---|---|
| gae/ha | gai/ha | Obs | Exp |
| 8 | 0 | 20 | — |
| 0 | 305 | 10 | — |
| 0 | 610 | 10 | — |
| 8 | 305 | 40 | 28 |
| 8 | 610 | 45 | 28 |

| Compound A Benzyl Ester | Pethoxamid | Visual Weed Control (%) - 21 DAA | | | |
|---|---|---|---|---|---|
| | | CYPES | | CYPIR | |
| gae/ha | gai/ha | Obs | Exp | Obs | Exp |
| 8 | 0 | 85 | — | 30 | — |
| 0 | 305 | 0 | — | 40 | — |
| 0 | 610 | 25 | — | 80 | — |
| 0 | 1220 | 65 | — | 85 | — |
| 8 | 305 | 100 | 85 | 100 | 58 |
| 8 | 610 | 100 | 89 | 100 | 86 |
| 8 | 1220 | 95 | 95 | 100 | 90 |

TABLE 25

Synergistic Activity of Foliar-Applied Compound A Benzyl Ester and Pyroxasulfone Herbicidal Compositions on Weed Control in a Rice Cropping System.

| Compound A Benzyl Ester | Pyroxasulfone | Visual Weed Control (%) - 22 DAA BRAPP | |
|---|---|---|---|
| gae/ha | gai/ha | Obs | Exp |
| 8 | 0 | 60 | — |
| 16 | 0 | 60 | — |
| 32 | 0 | 90 | — |
| 0 | 29.5 | 0 | — |
| 0 | 59 | 0 | — |
| 0 | 118 | 20 | — |
| 8 | 29.5 | 75 | 60 |
| 16 | 29.5 | 50 | 60 |
| 32 | 29.5 | 90 | 90 |
| 8 | 59 | 75 | 60 |
| 16 | 59 | 85 | 60 |
| 32 | 59 | 99 | 90 |
| 8 | 118 | 80 | 68 |
| 16 | 118 | 95 | 68 |
| 32 | 118 | 99 | 92 |

| Compound A Benzyl Ester | Pyroxasulfone | Visual Weed Control (%) - 22 DAA ECHCG | |
|---|---|---|---|
| gae/ha | gai/ha | Obs | Exp |
| 8 | 0 | 25 | — |
| 16 | 0 | 50 | — |
| 32 | 0 | 85 | — |
| 0 | 59 | 70 | — |
| 8 | 59 | 90 | 78 |
| 16 | 59 | 85 | 85 |
| 32 | 59 | 99 | 96 |

| | | |
|---|---|---|
| BRAPP | *Urochloa platyphylla* (Nash) R. D. Webster or *Brachiaria platyphylla* (Griseb.) Nash | signalgrass, broadleaf |
| CYPIR | *Cyperus iria* L. | flatsedge, rice |
| CYPES | *Cyperus esculentus* L. | nutsedge, yellow |
| DIGSA | *Digitaria sanguinalis* (L.) Scop. | crabgrass, large |
| ECHCG | *Echinochloa crusgalli* (L.) Beauv. | barnyardgrass |
| ECHCO | *Echinochloa colona* (L.) Link | junglerice |
| IPOHE | *Ipomoea hederacea* Jacq. | morningglory, ivyleaf |
| ISCRU | *Ischaemum rugosum* Salisb. | saramollagrass |
| LEFCH | *Leptochloa chinensis* (L.) Nees | sprangletop, Chinese |
| SCPJU | *Schoenoplectus juncoides* (Roxb.) Palla | bulrush, Japanese | gae/ha = grams acid equivalent per hectare
gai/ha = grams active ingredient per hectare
Obs = observed value
Exp = expected value as calculated by Colby's equation
DAA = days after application
NT = not tested Example II Evaluation of In-Water Applied Herbicidal Mixtures for Weed Control in Transplanted Paddy Rice Weed seeds or nutlets of the desired test plant species were planted in puddled soil (mud) prepared by mixing a shredded, non-sterilized mineral soil (50.5 percent silt, 25.5 percent clay, and 24 percent sand, with a pH of about 7.6 and an organic matter content of about 2.9 percent) and water at a 1:1 volumetric ratio. The prepared mud was dispensed in 365 mL aliquots into 16-ounce (oz.) non-perforated plastic pots with a surface area of 86.59 square centimeters ($cm^2$) leaving a headspace of 3 centimeters (cm) in each pot. Mud was allowed to dry overnight prior to planting or transplanting. Rice seeds were planted in Sun Gro MetroMix® 306 planting mixture, which typically has a pH of 6.0 to 6.8 and an organic matter content of about 30 percent, in plastic plug trays. Seedlings at the second or third leaf stage of growth were transplanted into 840 mL of mud contained in 32-oz. non-perforated plastic pots with a surface area of 86.59 cm² 4 days prior to herbicide application. The paddy was created by filling the headspace of the pots with 2.5 to 3 cm of water. When required to ensure good germination and healthy plants, a fungicide treatment and/or other chemical or physical treatment was applied. The plants were grown for 4-22 days in a greenhouse with an approximate 14 hr photoperiod which was maintained at about 29'C during the day and 26° C. during the night. Nutrients were added as Osmocote® (19:6:12, N:P:K+ minor nutrients) at 2 g per 16-oz. pot and 4 g per 32-oz. pot. Water was added on a regular basis to maintain the paddy flood, and supplemental lighting was provided with overhead metal halide 1000-Watt lamps as necessary. The plants were employed for testing when they reached the first through fourth true leaf stage.

Treatments consisted of the acid or esters of 4-amino-3-chloro-5-fluoro-6-(4-chloro-2-fluoro-3-methoxy-phenyl) pyridine-2-carboxylic acid (compound A) each formulated as an SC (suspension concentrate) and various herbicidal components alone and in combination. Forms of compound A were applied on an acid equivalent basis.

Forms of compound A (compound of formula I) tested include:

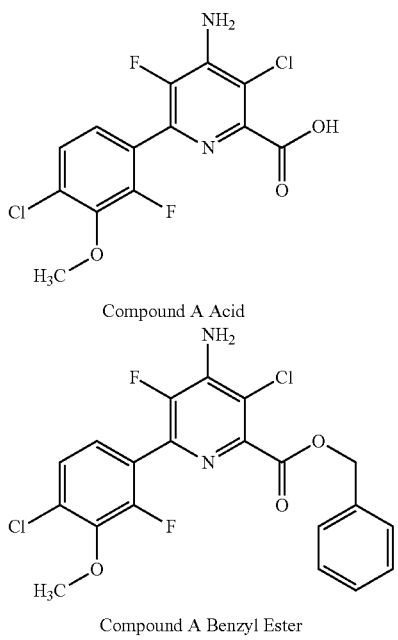

Compound A Acid

Compound A Benzyl Ester

The herbicidal components were applied on an active ingredient basis and included very long chain fatty acid (VLCFA) synthesis-inhibiting and fatty acid/lipid synthesis-inhibiting herbicides acetochlor (technical grade material), acetochlor+dichlormid formulated as Topnotch®, pretilachlor (technical grade material), butachlor formulated as Butachlor EC, fentrazamide formulated as Fentrazamide EC, thiobencarb formulated as Bolero® 8EC, cafenstrole formulated as Himeadow® WP or Lapost® Flowable, benfuresate formulated as Full Shot®, anilofos (technical grade material), mefenacet (technical grade material), molinate (technical grade material), and thenylchlor (technical grade material).

Treatment requirements for each compound or herbicidal component were calculated based upon the rates being tested, the concentration of active ingredient or acid equivalent in the formulation, an application volume of 2 mL per component per pot, and an application area of 86.59 cm² per pot.

For formulated compounds, a measured amount was placed in an individual 100 or 200 mL glass vial and was dissolved in a volume of 1.25% (v/v) Agri-Dex® crop oil concentrate to obtain application solutions. If the test compound did not dissolve readily, the mixture was warmed and/or sonicated.

For technical grade compounds, a weighed amount was placed in an individual 100 to 200 mL glass vial and was dissolved in a volume of acetone to obtain concentrated stock solutions. If the test compound did not dissolve readily, the mixture was warmed and/or sonicated. The concentrated stock solutions obtained were diluted with an equivalent volume of an aqueous mixture containing 2.5% (v/v) crop oil concentrate so that the final application solutions contained 1.25% (v/v) crop oil concentrate.

Applications were made by injecting with a pipetter appropriate amounts of the application solutions, individually and sequentially, into the aqueous layer of the paddy. Control plants were treated in the same manner with the solvent blank. Applications were made so that all treated plant material received the same concentrations of acetone and crop oil concentrate.

The treated plants and control plants were placed in a greenhouse as described above and water was added as needed to maintain a paddy flood. After approximately 3 weeks the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

Expected=$A+B-(A \times B/100)$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Tables 26-48.

TABLE 26

Synergistic Activity of In-Water Applications of Compound A Acid and Acetochlor Herbicidal Compositions on Control of Weeds Common to Rice Cropping Systems.

| Compound A Acid | Acetochlor | Visual Weed Control (%) - 20 DAA ECHOR | |
|---|---|---|---|
| gae/ha | gai/ha | Obs | Exp |
| 8.75 | 0 | 10 | — |
| 17.5 | 0 | 25 | — |
| 35 | 0 | 25 | — |
| 0 | 100 | 80 | — |

TABLE 26-continued

Synergistic Activity of In-Water Applications of Compound A Acid and Acetochlor Herbicidal Compositions on Control of Weeds Common to Rice Cropping Systems.

| | 8.75 | 100 | 100 | 82 |
| | 17.5 | 100 | 100 | 85 |
| | 35 | 100 | 100 | 85 |

| Compound A Acid | Acetochlor | Visual Weed Control (%) - 22 DAA ECHCG | |
|---|---|---|---|
| gae/ha | gai/ha | Obs | Exp |
| 8.75 | 0 | 0 | — |
| 17.5 | 0 | 15 | — |
| 35 | 0 | 15 | — |
| 0 | 100 | 65 | — |
| 8.75 | 100 | 99 | 65 |
| 17.5 | 100 | 100 | 70 |
| 35 | 100 | 100 | 70 |

| Compound A Acid | Acetochlor | Visual Weed Control (%) - 20 DAA CYPRO | |
|---|---|---|---|
| gae/ha | gai/ha | Obs | Exp |
| 8.75 | 0 | 0 | — |
| 17.5 | 0 | 70 | — |
| 0 | 100 | 20 | — |
| 0 | 200 | 75 | — |
| 8.75 | 100 | 100 | 20 |
| 17.5 | 100 | 100 | 76 |
| 8.75 | 200 | 100 | 75 |
| 17.5 | 200 | 99 | 93 |

TABLE 27

Synergistic Activity of In-Water Applications of Compound A Benzyl Ester and Acetochlor Herbicidal Compositions on Control of Weeds Common to Rice Cropping Systems.

| Compound A Benzyl Ester | Acetochlor | Visual Weed Control (%) - 20 DAA | | | |
|---|---|---|---|---|---|
| | | ECHOR | | CYPRO | |
| gae/ha | gai/ha | Obs | Exp | Obs | Exp |
| 4.38 | 0 | 10 | — | 0 | — |
| 8.75 | 0 | 20 | — | 20 | — |
| 17.5 | 0 | 50 | — | 95 | — |
| 0 | 100 | 80 | — | 20 | — |
| 4.38 | 100 | 100 | 82 | 95 | 20 |
| 8.75 | 100 | 100 | 84 | 99 | 36 |
| 17.5 | 100 | 100 | 90 | 100 | 96 |

| Compound A Benzyl Ester | Acetochlor | Visual Weed Control (%) - 22 DAA ECHCG | |
|---|---|---|---|
| gae/ha | gai/ha | Obs | Exp |
| 4.38 | 0 | 10 | — |
| 8.75 | 0 | 25 | — |
| 17.5 | 0 | 60 | — |
| 0 | 100 | 65 | — |
| 4.38 | 100 | 100 | 69 |
| 8.75 | 100 | 100 | 74 |
| 17.5 | 100 | 100 | 86 |

TABLE 27-continued

Synergistic Activity of In-Water Applications of Compound A Benzyl Ester and Acetochlor Herbicidal Compositions on Control of Weeds Common to Rice Cropping Systems.

| Compound A Benzyl Ester | Acetochlor | Visual Weed Control (%) - 20 DAA FIMMI | |
|---|---|---|---|
| gae/ha | gai/ha | Obs | Exp |
| 4.38 | 0 | 30 | — |
| 8.75 | 0 | 60 | — |
| 0 | 100 | 80 | — |
| 0 | 200 | 20 | — |
| 4.38 | 100 | 100 | 86 |
| 8.75 | 100 | 100 | 92 |
| 4.38 | 200 | 100 | 44 |
| 8.75 | 200 | 100 | 68 |

TABLE 28

Synergistic Activity of In-Water Applications of Compound A Acid and Acetochlor + Dichlormid Herbicidal Compositions on Control of Weeds Common to Rice Cropping Systems.

| Compound A Acid | Acetochlor + dichlormid | Visual Weed Control (%) - 20 DAA CYPRO | |
|---|---|---|---|
| gae/ha | gai/ha* | Obs | Exp |
| 8.75 | 0 | 0 | — |
| 17.5 | 0 | 20 | — |
| 35 | 0 | 80 | — |
| 0 | 100 | 0 | — |
| 0 | 200 | 70 | — |
| 8.75 | 100 | 90 | 0 |
| 17.5 | 100 | 100 | 20 |
| 35 | 100 | 95 | 80 |
| 8.75 | 200 | 100 | 70 |
| 17.5 | 200 | 100 | 76 |
| 35 | 200 | 100 | 94 |

*gai/ha refers to active ingredient of acetochlor.

TABLE 29

Synergistic Activity of In-Water Applications of Compound A Benzyl Ester and Acetochlor + Dichlormid Herbicidal Compositions on Control of Weeds Common to Rice Cropping Systems.

| Compound A Benzyl Ester | Acetochlor + dichlormid | Visual Weed Control (%) - 20 DAA CYPRO | |
|---|---|---|---|
| gae/ha | gai/ha* | Obs | Exp |
| 4.38 | 0 | 70 | — |
| 8.75 | 0 | 30 | — |
| 0 | 100 | 0 | — |
| 0 | 200 | 70 | — |
| 4.38 | 100 | 99 | 70 |
| 8.75 | 100 | 100 | 30 |
| 4.38 | 200 | 100 | 91 |
| 8.75 | 200 | 100 | 79 |

*gai/ha refers to active ingredient of acetochlor.

TABLE 30

Synergistic Activity of In-Water Applications of Compound A Acid and Pretilachlor Herbicidal Compositions on Weed Control in a Rice Cropping System.

| Compound A Acid | Pretilachlor | \multicolumn{4}{c}{Visual Weed Control (%) - 20 DAA} | | | |
|---|---|---|---|---|---|
| | | ECHOR | | CYPRO | |
| gae/ha | gai/ha | Obs | Exp | Obs | Exp |
| 8.75 | 0 | 10 | — | 0 | — |
| 17.5 | 0 | 25 | — | 70 | — |
| 35 | 0 | 25 | — | 90 | — |
| 0 | 75 | 0 | — | 0 | — |
| 0 | 150 | 30 | — | 0 | — |
| 8.75 | 75 | 35 | 10 | 0 | 0 |
| 17.5 | 75 | 85 | 25 | 100 | 70 |
| 35 | 75 | 80 | 25 | 100 | 90 |
| 8.75 | 150 | 95 | 37 | 75 | 0 |
| 17.5 | 150 | 80 | 48 | 100 | 70 |
| 35 | 150 | 100 | 48 | 100 | 90 |

| Compound A Acid | Pretilachlor | \multicolumn{4}{c}{Visual Weed Control (%) - 20 DAA} | | | |
|---|---|---|---|---|---|
| | | FIMMI | | SCPJU | |
| gae/ha | gai/ha | Obs | Exp | Obs | Exp |
| 8.75 | 0 | 50 | — | 40 | — |
| 0 | 75 | 40 | — | 50 | — |
| 0 | 150 | 45 | — | 20 | — |
| 8.75 | 75 | 100 | 70 | 90 | 70 |
| 8.75 | 150 | 100 | 73 | 95 | 52 |

TABLE 31

Synergistic Activity of In-Water Applications of Compound A Benzyl Ester and Pretilachlor Herbicidal Compositions on Weed Control in a Rice Cropping System.

| Compound A Benzyl Ester | Pretilachlor | \multicolumn{2}{c}{Visual Weed Control (%) - 20 DAA ECHOR} | |
|---|---|---|---|
| gae/ha | gai/ha | Obs | Exp |
| 4.38 | 0 | 10 | — |
| 8.75 | 0 | 20 | — |
| 17.5 | 0 | 50 | — |
| 0 | 75 | 0 | — |
| 0 | 150 | 30 | — |
| 4.38 | 75 | 85 | 10 |
| 8.75 | 75 | 75 | 20 |
| 17.5 | 75 | 95 | 50 |
| 4.38 | 150 | 85 | 37 |
| 8.75 | 150 | 95 | 44 |
| 17.5 | 150 | 99 | 65 |

| Compound A Benzyl Ester | Pretilachlor | \multicolumn{4}{c}{Visual Weed Control (%) - 20 DAA} | | | |
|---|---|---|---|---|---|
| | | CYPRO | | FIMMI | |
| gae/ha | gai/ha | Obs | Exp | Obs | Exp |
| 4.38 | 0 | 0 | — | 30 | — |
| 8.75 | 0 | 20 | — | 60 | — |
| 0 | 75 | 0 | — | 40 | — |
| 0 | 150 | 0 | — | 45 | — |
| 4.38 | 75 | 0 | 0 | 100 | 58 |
| 8.75 | 75 | 85 | 20 | 100 | 76 |
| 4.38 | 150 | 40 | 0 | 100 | 62 |
| 8.75 | 150 | 75 | 20 | 100 | 78 |

TABLE 32

Synergistic Activity of In-Water Applications of Compound A Acid and Butachlor Herbicidal Compositions on Weed Control in a Rice Cropping System.

| Compound A Acid | Butachlor | \multicolumn{4}{c}{Visual Weed Control (%) - 21 DAA} | | | |
|---|---|---|---|---|---|
| | | ECHCG | | ECHOR | |
| gae/ha | gai/ha | Obs | Exp | Obs | Exp |
| 8.75 | 0 | 0 | — | 30 | — |
| 17.5 | 0 | 0 | — | 25 | — |
| 35 | 0 | 20 | — | 30 | — |
| 0 | 225 | 40 | — | 0 | — |
| 0 | 450 | 20 | — | 20 | — |
| 8.75 | 225 | 20 | 40 | 85 | 30 |
| 17.5 | 225 | 40 | 40 | 95 | 25 |
| 35 | 225 | 95 | 52 | 95 | 30 |
| 8.75 | 450 | 50 | 20 | 70 | 44 |
| 17.5 | 450 | 60 | 20 | 99 | 40 |
| 35 | 450 | 95 | 36 | 99 | 44 |

| Compound A Acid | Butachlor | \multicolumn{2}{c}{Visual Weed Control (%) - 21 DAA CYPRO} | |
|---|---|---|---|
| gae/ha | gai/ha | Obs | Exp |
| 8.75 | 0 | 0 | — |
| 0 | 225 | 0 | — |
| 0 | 450 | 0 | — |
| 8.75 | 225 | 70 | 0 |
| 8.75 | 450 | 15 | 0 |

TABLE 33

Synergistic Activity of In-Water Applications of Compound A Benzyl Ester and Butachlor Herbicidal Compositions on Weed Control in a Rice Cropping System.

| Compound A Benzyl Ester | Butachlor | \multicolumn{4}{c}{Visual Weed Control (%) - 21 DAA} | | | |
|---|---|---|---|---|---|
| | | ECHCG | | ECHOR | |
| gae/ha | gai/ha | Obs | Exp | Obs | Exp |
| 4.38 | 0 | 15 | — | 0 | — |
| 8.75 | 0 | 20 | — | 15 | — |
| 17.5 | 0 | 75 | — | 10 | — |
| 0 | 225 | 40 | — | 0 | — |
| 0 | 450 | 20 | — | 20 | — |
| 4.38 | 225 | 45 | 49 | 75 | 0 |
| 8.75 | 225 | 75 | 52 | 99 | 15 |
| 17.5 | 225 | 95 | 85 | 95 | 10 |
| 4.38 | 450 | 50 | 32 | 50 | 20 |
| 8.75 | 450 | 70 | 36 | 95 | 32 |
| 17.5 | 450 | 95 | 80 | 95 | 28 |

| Compound A Benzyl Ester | Butachlor | \multicolumn{2}{c}{Visual Weed Control (%) - 21 DAA CYPRO} | |
|---|---|---|---|
| gae/ha | gai/ha | Obs | Exp |
| 4.38 | 0 | 0 | — |
| 8.75 | 0 | 30 | — |
| 0 | 225 | 0 | — |
| 0 | 450 | 0 | — |
| 4.38 | 225 | 30 | 0 |
| 8.75 | 225 | 85 | 30 |
| 4.38 | 450 | 80 | 0 |
| 8.75 | 450 | 60 | 30 |

TABLE 34

Synergistic Activity of In-Water Applications of Compound A Acid and Fentrazamide Herbicidal Compositions on Weed Control in a Rice Cropping System.

| Compound A Acid | Fentrazamide | Visual Weed Control (%) - 21 DAA ECHOR | |
|---|---|---|---|
| gae/ha | gai/ha | Obs | Exp |
| 8.75 | 0 | 10 | — |
| 17.5 | 0 | 20 | — |
| 35 | 0 | 35 | — |
| 0 | 50 | 50 | — |
| 8.75 | 50 | 90 | 55 |
| 17.5 | 50 | 80 | 60 |
| 35 | 50 | 95 | 68 |

TABLE 35

Synergistic Activity of In-Water Applications of Compound A Benzyl Ester and Fentrazamide Herbicidal Compositions on Weed Control in a Rice Cropping System.

| Compound A Benzyl Ester | Fentrazamide | Visual Weed Control (%) - 21 DAA ECHOR | |
|---|---|---|---|
| gae/ha | gai/ha | Obs | Exp |
| 4.38 | 0 | 25 | — |
| 8.75 | 0 | 25 | — |
| 17.5 | 0 | 60 | — |
| 0 | 50 | 50 | — |
| 4.38 | 50 | 70 | 63 |
| 8.75 | 50 | 85 | 63 |
| 17.5 | 50 | 95 | 80 |

TABLE 36

Synergistic Activity of In-Water Applications of Compound A Acid and Thiobencarb Herbicidal Compositions on Weed Control in a Rice Cropping System.

| Compound A Acid | Thiobencarb | Visual Weed Control (%) - 20 DAA ECHOR | |
|---|---|---|---|
| gae/ha | gai/ha | Obs | Exp |
| 8.75 | 0 | 10 | — |
| 17.5 | 0 | 25 | — |
| 35 | 0 | 25 | — |
| 0 | 1120 | 60 | — |
| 8.75 | 1120 | 85 | 64 |
| 17.5 | 1120 | 99 | 70 |
| 35 | 1120 | 99 | 70 |

TABLE 37

Synergistic Activity of In-Water Applications of Compound A Benzyl Ester and Thiobencarb Herbicidal Compositions on Weed Control in a Rice Cropping System.

| Compound A Benzyl Ester | Thiobencarb | Visual Weed Control (%) - 20 DAA ECHOR | |
|---|---|---|---|
| gae/ha | gai/ha | Obs | Exp |
| 4.38 | 0 | 10 | — |
| 8.75 | 0 | 20 | — |
| 17.5 | 0 | 50 | — |
| 0 | 1120 | 60 | — |
| 0 | 2240 | 90 | — |
| 4.38 | 1120 | 99 | 64 |
| 8.75 | 1120 | 95 | 68 |
| 17.5 | 1120 | 100 | 80 |
| 4.38 | 2240 | 99 | 91 |
| 8.75 | 2240 | 99 | 92 |
| 17.5 | 2240 | 100 | 95 |

| Compound A Benzyl Ester | Thiobencarb | Visual Weed Control (%) - 20 DAA CYPRO | |
|---|---|---|---|
| gae/ha | gai/ha | Obs | Exp |
| 4.38 | 0 | 0 | — |
| 8.75 | 0 | 20 | — |
| 17.5 | 0 | 95 | — |
| 0 | 1120 | 0 | — |
| 0 | 2240 | 0 | — |
| 4.38 | 1120 | 0 | 0 |
| 8.75 | 1120 | 95 | 20 |
| 17.5 | 1120 | 95 | 95 |
| 4.38 | 2240 | 90 | 0 |
| 8.75 | 2240 | 85 | 20 |
| 17.5 | 2240 | 100 | 95 |

TABLE 38

Synergistic Activity of In-Water Applications of Compound A Acid and Cafenstrole (Himeadow ® WP) Herbicidal Compositions on Weed Control in a Rice Cropping System.

| Compound A Acid | Cafenstrole | Visual Weed Control (%) - 21 DAA | | | |
|---|---|---|---|---|---|
| | | ECHCG | | ECHOR | |
| gae/ha | gai/ha | Obs | Exp | Obs | Exp |
| 8.75 | 0 | 0 | — | 30 | — |
| 17.5 | 0 | 0 | — | 25 | — |
| 35 | 0 | 20 | — | 30 | — |
| 0 | 52.5 | 20 | — | 10 | — |
| 0 | 105 | 25 | — | 30 | — |
| 8.75 | 52.5 | 50 | 20 | 75 | 37 |
| 17.5 | 52.5 | 45 | 20 | 50 | 33 |
| 35 | 52.5 | 99 | 36 | 100 | 37 |
| 8.75 | 105 | 80 | 25 | 100 | 51 |
| 17.5 | 105 | 95 | 25 | 99 | 48 |
| 35 | 105 | 100 | 40 | 95 | 51 |

TABLE 39

Synergistic Activity of In-Water Applications of Compound A Benzyl Ester and Cafenstrole (Himeadow ® WP) Herbicidal Compositions on Weed Control in a Rice Cropping System.

| Compound A Benzyl Ester | Cafenstrole | Visual Weed Control (%) - 21 DAA | | | |
|---|---|---|---|---|---|
| | | ECHCG | | ECHOR | |
| gae/ha | gai/ha | Obs | Exp | Obs | Exp |
| 4.38 | 0 | 15 | — | 0 | — |
| 8.75 | 0 | 20 | — | 15 | — |
| 17.5 | 0 | 75 | — | 10 | — |
| 0 | 52.5 | 20 | — | 10 | — |
| 0 | 105 | 25 | — | 30 | — |
| 4.38 | 52.5 | 95 | 32 | 50 | 10 |

TABLE 39-continued

Synergistic Activity of In-Water Applications of Compound A Benzyl Ester and Cafenstrole (Himeadow ® WP) Herbicidal Compositions on Weed Control in a Rice Cropping System.

| 8.75 | 52.5 | 95 | 36 | 100 | 24 |
| 17.5 | 52.5 | 100 | 80 | 100 | 19 |
| 4.38 | 105 | 60 | 36 | 85 | 30 |
| 8.75 | 105 | 99 | 40 | 100 | 41 |
| 17.5 | 105 | 100 | 81 | 99 | 37 |

| Compound A Benzyl Ester | Cafenstrole | Visual Weed Control (%) - 21 DAA CYPRO | |
|---|---|---|---|
| gae/ha | gai/ha | Obs | Exp |
| 4.38 | 0 | 0 | — |
| 8.75 | 0 | 30 | — |
| 0 | 52.5 | 0 | — |
| 0 | 105 | 0 | — |
| 4.38 | 52.5 | 0 | 0 |
| 8.75 | 52.5 | 90 | 30 |
| 4.38 | 105 | 20 | 0 |
| 8.75 | 105 | 80 | 30 |

TABLE 40

Synergistic Activity of In-Water Applications of Compound A Acid and Cafenstrole (Lapost ® Flowable) Herbicidal Compositions on Weed Control in a Rice Cropping System.

| Compound A Acid | Cafenstrole | Visual Weed Control (%) - 21 DAA ECHOR | |
|---|---|---|---|
| gae/ha | gai/ha | Obs | Exp |
| 8.75 | 0 | 10 | — |
| 17.5 | 0 | 10 | — |
| 35 | 0 | 15 | — |
| 0 | 52.5 | 70 | — |
| 8.75 | 52.5 | 95 | 73 |
| 17.5 | 52.5 | 99 | 73 |
| 35 | 52.5 | 95 | 75 |

| Compound A Acid | Cafenstrole | Visual Weed Control (%) - 21 DAA CYPRO | |
|---|---|---|---|
| gae/ha | gai/ha | Obs | Exp |
| 8.75 | 0 | 0 | — |
| 17.5 | 0 | 20 | — |
| 0 | 52.5 | 0 | — |
| 0 | 105 | 0 | — |
| 8.75 | 52.5 | 95 | 0 |
| 17.5 | 52.5 | 100 | 20 |
| 8.75 | 105 | 95 | 0 |
| 17.5 | 105 | 90 | 20 |

| Compound A Acid | Cafenstrole | Visual Weed Control (%) - 21 DAA LEFCH | |
|---|---|---|---|
| gae/ha | gai/ha | Obs | Exp |
| 35 | 0 | 5 | — |
| 70 | 0 | 23 | — |
| 0 | 210 | 38 | — |
| 35 | 210 | 58 | 41 |
| 70 | 210 | 55 | 52 |

TABLE 41

Synergistic Activity of In-Water Applications of Compound A Benzyl Ester and Cafenstrole (Lapost ® Flowable) Herbicidal Compositions on Weed Control in a Rice Cropping System.

| Compound A Benzyl Ester | Cafenstrole | Visual Weed Control (%) - 21 DAA ECHOR | |
|---|---|---|---|
| gae/ha | gai/ha | Obs | Exp |
| 4.38 | 0 | 25 | — |
| 8.75 | 0 | 25 | — |
| 17.5 | 0 | 25 | — |
| 0 | 52.5 | 70 | — |
| 4.38 | 52.5 | 90 | 78 |
| 8.75 | 52.5 | 99 | 78 |
| 17.5 | 52.5 | 99 | 78 |

| Compound A Benzyl | Cafenstrole | Visual Weed Control (%) - 21 DAA LEFCH | |
|---|---|---|---|
| gae/ha | gai/ha | Obs | Exp |
| 35 | 0 | 50 | — |
| 70 | 0 | 50 | — |
| 0 | 210 | 38 | — |
| 35 | 210 | 88 | 69 |
| 70 | 210 | 80 | 69 |

TABLE 42

Synergistic Activity of In-Water Applications of Compound A Acid and Benfuresate (Full Slot ®) Herbicidal Compositions on Weed Control in a Rice Cropping System.

| Compound A Acid | Benfuresate | Visual Weed Control (%) - 22 DAA ECHCG | |
|---|---|---|---|
| gae/ha | gai/ha | Obs | Exp |
| 42.4 | 0 | 30 | — |
| 0 | 75 | 0 | — |
| 0 | 150 | 0 | — |
| 42.4 | 75 | 50 | 30 |
| 42.4 | 150 | 95 | 30 |

| Compound A Acid | Benfuresate | Visual Weed Control (%) - 22 DAA LEFCH | |
|---|---|---|---|
| gae/ha | gai/ha | Obs | Exp |
| 10.6 | 0 | 20 | — |
| 21.2 | 0 | 40 | — |
| 42.4 | 0 | 60 | — |
| 0 | 75 | 0 | — |
| 0 | 150 | 0 | — |
| 10.6 | 75 | 20 | 20 |
| 21.2 | 75 | 40 | 40 |
| 42.4 | 75 | 100 | 60 |
| 10.6 | 150 | 60 | 20 |
| 21.2 | 150 | 80 | 40 |
| 42.4 | 150 | 100 | 60 |

TABLE 43

Synergistic Activity of In-Water Applications of Compound A Benzyl Ester and Benfuresate (Full Slot) Herbicidal Compositions on Weed Control in a Rice Cropping System.

| Compound A Benzyl Ester | Benfuresate | Visual Weed Control (%) - 22 DAA ECHOR | |
|---|---|---|---|
| gae/ha | gai/ha | Obs | Exp |
| 8.75 | 0 | 35 | — |
| 17.5 | 0 | 30 | — |
| 0 | 75 | 0 | — |
| 0 | 150 | 0 | — |
| 8.75 | 75 | 15 | 35 |
| 17.5 | 75 | 95 | 30 |
| 8.75 | 150 | 80 | 35 |
| 17.5 | 150 | 95 | 30 |

| Compound A Benzyl Ester | Benfuresate | Visual Weed Control (%) - 22 DAA LEFCH | |
|---|---|---|---|
| gae/ha | gai/ha | Obs | Exp |
| 4.38 | 0 | 20 | — |
| 0 | 75 | 0 | — |
| 0 | 150 | 0 | — |
| 4.38 | 75 | 45 | 20 |
| 4.38 | 150 | 100 | 20 |

TABLE 44

Synergistic Activity of In-Water Applications of Compound A Benzyl Ester and Anilofos Herbicidal Compositions on Weed Control in a Rice Cropping System.

| Compound A Benzyl Ester | Anilofos | Visual Weed Control (%) - 19 DAA ECHCG | |
|---|---|---|---|
| gae/ha | gai/ha | Obs | Exp |
| 8 | 0 | 30 | — |
| 16 | 0 | 20 | — |
| 32 | 0 | 40 | — |
| 0 | 100 | 20 | — |
| 8 | 100 | 20 | 44 |
| 16 | 100 | 95 | 36 |
| 32 | 100 | 99 | 52 |

| Compound A Benzyl Ester | Anilofos | Visual Weed Control (%) - 19 DAA ECHOR | |
|---|---|---|---|
| gae/ha | gai/ha | Obs | Exp |
| 8 | 0 | 10 | — |
| 16 | 0 | 20 | — |
| 32 | 0 | 25 | — |
| 0 | 100 | 40 | — |
| 0 | 200 | 80 | — |
| 8 | 100 | 60 | 46 |
| 16 | 100 | 50 | 52 |
| 32 | 100 | 50 | 55 |
| 8 | 200 | 95 | 82 |
| 16 | 200 | 99 | 84 |
| 32 | 200 | 95 | 85 |

| Compound A Benzyl Ester | Anilofos | Visual Weed Control (%) - 19 DAA CYPRO | |
|---|---|---|---|
| gae/ha | gai/ha | Obs | Exp |
| 8 | 0 | 50 | — |
| 0 | 100 | 0 | — |
| 0 | 200 | 0 | — |
| 0 | 400 | 0 | — |
| 8 | 100 | 85 | 50 |
| 8 | 200 | 100 | 50 |
| 8 | 400 | 80 | 50 |

| Compound A Benzyl Ester | Anilofos | Visual Weed Control (%) - 19 DAA FIMMI | |
|---|---|---|---|
| gae/ha | gai/ha | Obs | Exp |
| 8 | 0 | 0 | — |
| 16 | 0 | 0 | — |
| 32 | 0 | 85 | — |
| 0 | 100 | 0 | — |
| 0 | 200 | 0 | — |
| 0 | 400 | 10 | — |
| 8 | 100 | 0 | 0 |
| 16 | 100 | 20 | 0 |
| 32 | 100 | 100 | 85 |
| 8 | 200 | 10 | 0 |
| 16 | 200 | 40 | 0 |
| 32 | 200 | 100 | 85 |
| 8 | 400 | 25 | 10 |
| 16 | 400 | 30 | 10 |
| 32 | 400 | 100 | 87 |

TABLE 45

Synergistic Activity of In-Water Applications of Compound A Benzyl Ester and Indanofan Herbicidal Compositions on Weed Control in a Rice Cropping System.

| Compound A Benzyl Ester | Indanofan | Visual Weed Control (%) - 19 DAA LEFCH | |
|---|---|---|---|
| gae/ha | gai/ha | Obs | Exp |
| 8 | 0 | 0 | — |
| 16 | 0 | 0 | — |
| 32 | 0 | 15 | — |
| 0 | 37.5 | 10 | — |
| 0 | 75 | 20 | — |
| 0 | 150 | 95 | — |
| 8 | 37.5 | 15 | 10 |
| 16 | 37.5 | 25 | 10 |
| 32 | 37.5 | 25 | 24 |
| 8 | 75 | 30 | 20 |
| 16 | 75 | 20 | 20 |
| 32 | 75 | 60 | 32 |
| 8 | 150 | 100 | 95 |
| 16 | 150 | 40 | 95 |
| 32 | 150 | 100 | 96 |

TABLE 46

Synergistic Activity of In-Water Applications of Compound A Benzyl Ester and Mefenacet Herbicidal Compositions on Weed Control in a Rice Cropping System.

| Compound A Benzyl Ester | Mefenacet | Visual Weed Control (%) - 21 DAA ECHOR | |
|---|---|---|---|
| gae/ha | gai/ha | Obs | Exp |
| 8 | 0 | 75 | — |
| 16 | 0 | 95 | — |
| 32 | 0 | 100 | — |

TABLE 46-continued

Synergistic Activity of In-Water Applications of Compound
A Benzyl Ester and Mefenacet Herbicidal Compositions
on Weed Control in a Rice Cropping System.

| Compound A Benzyl Ester | Mefenacet | Visual Weed Control (%) - 21 DAA ECHOR | |
|---|---|---|---|
| gae/ha | gai/ha | Obs | Exp |
| 0 | 300 | 80 | |
| 0 | 600 | 100 | |
| 0 | 1200 | 100 | |
| 8 | 300 | 100 | 48 |
| 16 | 300 | 99 | 64 |
| 32 | 300 | 100 | 74 |
| 8 | 600 | 100 | 68 |
| 16 | 600 | 100 | 78 |
| 32 | 600 | 100 | 84 |
| 8 | 1200 | 100 | 84 |
| 16 | 1200 | 100 | 89 |
| 32 | 1200 | 100 | 92 |

TABLE 47

Synergistic Activity of In-Water Applications of Compound
A Benzyl Ester and Molinate Herbicidal Compositions
on Weed Control in a Rice Cropping System.

| Compound A Benzyl Ester | Molinate | Visual Weed Control (%) - 21 DAA ECHOR | |
|---|---|---|---|
| gae/ha | gai/ha | Obs | Exp |
| 8 | 0 | 25 | — |
| 16 | 0 | 30 | — |
| 32 | 0 | 45 | — |
| 0 | 1400 | 55 | — |
| 0 | 2800 | 85 | — |
| 8 | 1400 | 65 | 66 |
| 16 | 1400 | 75 | 69 |
| 32 | 1400 | 90 | 75 |
| 8 | 2800 | 90 | 89 |
| 16 | 2800 | 99 | 90 |
| 32 | 2800 | 99 | 92 |

TABLE 48

Synergistic Activity of In-Water Applications of Compound
A Benzyl Ester and Thenylchlor Herbicidal Compositions
on Weed Control in a Rice Cropping System.

| Compound A Benzyl Ester | Thenylchlor | Visual Weed Control (%) - 19 DAA | | | |
|---|---|---|---|---|---|
| | | ECHOR | | LEFCH | |
| gae/ha | gai/ha | Obs | Exp | Obs | Exp |
| 8 | 0 | 30 | — | 0 | — |
| 16 | 0 | 95 | — | 0 | — |
| 32 | 0 | 70 | — | 15 | — |
| 0 | 135 | 35 | — | 15 | — |
| 0 | 270 | 90 | — | 25 | — |
| 8 | 135 | 99 | 55 | 60 | 15 |
| 16 | 135 | 95 | 97 | 30 | 15 |
| 32 | 135 | 95 | 81 | 50 | 28 |
| 8 | 270 | 99 | 93 | 20 | 25 |
| 16 | 270 | 99 | 100 | 80 | 25 |
| 32 | 270 | 99 | 97 | 90 | 36 |

CYPRO  Cyperus rotundus L.  nutsedge, purple
ECHCG  Echinochloa crusgalli (L.) Beauv.  barnyardgrass
ECHOR  Echinochloa oryzoides (Ard.) Fritsch  watergrass, early TABLE 48-continued Synergistic Activity of In-Water Applications of Compound
A Benzyl Ester and Thenylchlor Herbicidal Compositions
on Weed Control in a Rice Cropping System.

FIMMI  Fimbristylis miliacea (L.) Vahl  fringerush, globe
LEFCH  Leptochloa chinensis (L.) Nees  sprangletop, Chinese
SCPJU  Schoenoplectus juncoides (Roxb.) Palla  bulrush, Japanese gae/ha = grams acid equivalent per hectare
gai/ha = grams active ingredient per hectare
Obs = observed value
Exp = expected value as calculated by Colby's equation
DAA = days after application Example III Evaluation of Post-Emergence Foliar-Applied Herbicidal Mixtures for Weed Control in Cereal Crops in the Greenhouse Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters (cm²). When required to ensure good germination and healthy plants, a fungicide treatment and/or other chemical or physical treatment was applied. The plants were grown for 7-36 days in a greenhouse with an approximate 14 hour photoperiod which was maintained at about 18° C. during the day and 17° C. during the night. Nutrients and water were added on a regular basis and supplemental lighting was provided with overhead metal halide 1000-Watt lamps as necessary. The plants were employed for testing when they reached the second or third true leaf stage.

Treatments consisted of the benzyl ester of 4-amino-3-chloro-5-fluoro-6-(4-chloro-2-fluoro-3-methoxy-phenyl)pyridine-2-carboxylic acid (Compound A), formulated as an SC (suspension concentrate), and a second cereal herbicide alone and in combination.

Forms of compound A (compound of formula I) tested include:

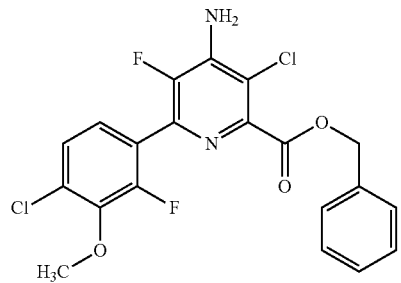

Compound A Benzyl Ester

Measured aliquots of the benzyl ester of 4-amino-3-chloro-5-fluoro-6-(4-chloro-2-fluoro-3-methoxy-phenyl)pyridine-2-carboxylic acid (Compound A) were placed in 25 milliliter (mL) glass vials and diluted in a volume of 1.25% (v/v) Agri-dex crop oil concentrated to obtain stock solutions. Compound requirements are based upon a 12 mL application volume at a rate of 187 liters per hectare (L/ha). Spray solutions of the second cereal herbicide and experimental compound mixtures were prepared by adding the stock solutions to the appropriate amount of dilution solution to form 12 mL spray solution with active ingredients in two- and three-way combinations. Formulated compounds were applied to the plant material with an overhead Mandel track sprayer equipped with an 8002E nozzle calibrated to deliver 187 L/ha over an application area of 0.503 square meters (m²) at a spray height of 18 inches (46 cm) above average plant canopy. Control plants were sprayed in the same manner with the solvent blank.

The treated plants and control plants were placed in a greenhouse as described above and watered by sub-irrigation to prevent wash-off of the test compounds. After 20-22 days, the condition of the test plants as compared with that of the control plants was determined visually and scored on a scale of 0 to 100 percent where 0 corresponds to no injury and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture.

B=observed efficacy of active ingredient B at the same concentration as used in the mixture.

The compounds tested, application rates employed, plant species tested, and results are given in Tables 49-50.

TABLE 49

Synergistic Activity of Foliar-Applied Compound A Benzyl Ester and Flufenacet Herbicidal Compositions on Weed Control in a Cereal Cropping System.

| Compound A Benzyl Ester | Flufenacet | Visual Weed Control (%) - 21 DAA | | | | | |
|---|---|---|---|---|---|---|---|
| | | CIRAR | | KCHSC | | PAPRH | |
| gai/ha | gai/ha | Obs | Exp | Obs | Exp | Obs | Exp |
| 2.5 | 0 | 48 | — | 20 | — | 48 | — |
| 5 | 0 | 39 | — | 41 | — | 28 | — |
| 10 | 0 | 60 | — | 62 | — | 35 | — |
| 0 | 60 | 0 | — | 5 | — | 0 | — |
| 0 | 120 | 0 | — | 5 | — | 5 | — |
| 0 | 240 | 17 | — | 17 | — | 7 | — |
| 2.5 | 60 | 53 | 48 | 63 | 24 | 50 | 48 |
| 2.5 | 120 | 48 | 48 | 70 | 24 | 63 | 50 |
| 5 | 60 | 60 | 39 | 55 | 44 | 40 | 28 |
| 5 | 120 | 63 | 39 | 73 | 44 | 73 | 32 |
| 5 | 240 | 70 | 49 | 84 | 51 | 43 | 33 |
| 10 | 240 | 80 | 67 | 86 | 68 | 84 | 39 |

| Compound A Benzyl Ester | Flufenacet | Visual Weed Control (%) - 21 DAA | | | |
|---|---|---|---|---|---|
| | | SASKR | | STEME | |
| gai/ha | gai/ha | Obs | Exp | Obs | Exp |
| 2.5 | 0 | 15 | — | 25 | — |
| 5 | 0 | 50 | — | 25 | — |
| 10 | 0 | 67 | — | 27 | — |
| 0 | 60 | 5 | — | 0 | — |
| 0 | 120 | 5 | — | 5 | — |
| 0 | 240 | 13 | — | 42 | — |
| 2.5 | 60 | 38 | 19 | 75 | 25 |
| 2.5 | 120 | 50 | 19 | 68 | 29 |
| 5 | 60 | 68 | 53 | 78 | 25 |
| 5 | 120 | 63 | 53 | 83 | 29 |
| 5 | 240 | 77 | 57 | 72 | 56 |
| 10 | 240 | 85 | 71 | 73 | 57 |

| Compound A Benzyl Ester | Flufenacet | Visual Weed Control (%) - 21 DAA | | | |
|---|---|---|---|---|---|
| | | CHEAL | | SINAR | |
| gai/ha | gai/ha | Obs | Exp | Obs | Exp |
| 2.5 | 0 | 50 | — | 70 | — |
| 5 | 0 | 58 | — | 73 | — |
| 0 | 60 | 0 | — | 5 | — |
| 0 | 120 | 0 | — | 8 | — |
| 2.5 | 60 | 75 | 50 | 83 | 72 |
| 2.5 | 120 | 75 | 50 | 88 | 72 |
| 5 | 60 | 83 | 58 | 84 | 74 |
| 5 | 120 | 80 | 58 | 85 | 75 |

TABLE 50

Synergistic Activity of Foliar-Applied Compound A Benzyl Ester and Prosulfocarb Herbicidal Compositions on Weed Control in a Cereal Cropping System.

| Compound A Benzyl Ester | Prosulfocarb | Visual Weed Control (%) - 21 DAA | | | |
|---|---|---|---|---|---|
| | | GALAP | | KCHSC | |
| gai/ha | gai/ha | Obs | Exp | Obs | Exp |
| 2.5 | 0 | 55 | — | 20 | — |
| 5 | 0 | 66 | — | 41 | — |
| 10 | 0 | 77 | — | 62 | — |
| 0 | 1000 | 15 | — | 10 | — |
| 0 | 2000 | 40 | — | 15 | — |
| 0 | 4000 | 67 | — | 75 | — |
| 2.5 | 1000 | 78 | 62 | 65 | 28 |
| 2.5 | 2000 | 78 | 73 | 73 | 32 |
| 5 | 1000 | 88 | 71 | 75 | 47 |
| 5 | 2000 | 88 | 80 | 78 | 50 |
| 5 | 4000 | 93 | 89 | 88 | 85 |
| 10 | 4000 | 94 | 92 | 92 | 90 |

| Compound A Benzyl Ester | Prosulfocarb | Visual Weed Control (%) - 21 DAA | | | | | |
|---|---|---|---|---|---|---|---|
| | | PAPRH | | SASKR | | STEME | |
| gai/ha | gai/ha | Obs | Exp | Obs | Exp | Obs | Exp |
| 2.5 | 0 | 48 | — | 15 | — | 25 | — |
| 5 | 0 | 28 | — | 50 | — | 25 | — |
| 10 | 0 | 35 | — | 67 | — | 27 | — |
| 0 | 1000 | 5 | — | 5 | — | 0 | — |
| 0 | 2000 | 10 | — | 5 | — | 10 | — |
| 0 | 4000 | 13 | — | 63 | — | 73 | — |
| 2.5 | 1000 | 48 | 50 | 45 | 19 | 50 | 25 |
| 2.5 | 2000 | 50 | 53 | 65 | 19 | 58 | 33 |
| 5 | 1000 | 85 | 32 | 58 | 53 | 55 | 25 |
| 5 | 2000 | 60 | 35 | 73 | 53 | 35 | 33 |
| 5 | 4000 | 63 | 38 | 80 | 82 | 91 | 80 |
| 10 | 4000 | 93 | 44 | 85 | 88 | 81 | 80 |

| Compound A Benzyl Ester | Prosulfocarb | Visual Weed Control (%) - 21 DAA | | | |
|---|---|---|---|---|---|
| | | CHEAL | | SINAR | |
| gai/ha | gai/ha | Obs | Exp | Obs | Exp |
| 2.5 | 0 | 50 | — | 70 | — |
| 5 | 0 | 58 | — | 73 | — |
| 0 | 1000 | 10 | — | 13 | — |

TABLE 50-continued

Synergistic Activity of Foliar-Applied Compound A
Benzyl Ester and Prosulfocarb Herbicidal Compositions
on Weed Control in a Cereal Cropping System.

| 0 | 2000 | 15 | — | 18 | — |
| 2.5 | 1000 | 83 | 55 | 88 | 74 |
| 2.5 | 2000 | 75 | 58 | 83 | 75 |
| 5 | 1000 | 83 | 62 | 86 | 76 |
| 5 | 2000 | 88 | 64 | 89 | 77 |

| CHEAL | *Chenopodium album* L. | lambsquarters, common |
| CIRAR | *Cirsium arvense* (L.) Scop. | thistle, Canada |
| GALAP | *Galium aparine* L. | cleavers, catchweed bedstraw |
| KCHSC | *Kochia scoparia* (L.) Schrad. | kochia |
| PAPRH | *Papaver rhoeas* L. | poppy, common |
| SASKR | *Salsola tragus* L. | thistle, Russian |
| SINAR | *Sinapis arvensis* L. | mustard, wild |
| STEME | *Stellaria media* (L.) Vill. | chickweed, common |

Example IV

Evaluation of Pre-emergence Soil-Applied Herbicidal Mixtures for Weed Control

Seeds or nutlets of the desired test plant species were planted in a soil matrix prepared by mixing a loam soil (32 percent silt, 23 percent clay, and 45 percent sand, with a pH of about 6.5 and an organic matter content of about 1.9 percent) and calcareous grit in an 80 to 20 ratio. The soil matrix was contained in plastic pots with a volume of 1 quart and a surface area of 83.6 square centimeters ($cm^2$).

Treatments consisted of the benzyl ester of 4-amino-3-chloro-5-fluoro-6-(4-chloro-2-fluoro-3-methoxy-phenyl)pyridine-2-carboxylic acid (compound A) formulated as an SC (suspension concentrate) and various herbicidal components alone and in combination. Forms of compound A were applied on an acid equivalent basis.

Forms of compound A (compound of formula I) tested include:

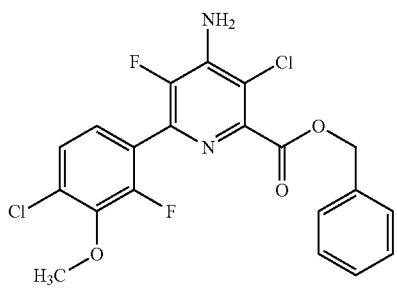

Compound A Benzyl Ester

Other herbicidal components were applied on an active ingredient basis and included very long chain fatty acid (VLCFA) synthesis-inhibiting and fatty acid/lipid synthesis-inhibiting herbicides alachlor (technical grade material), dimethenamid-P formulated as Outlook®, and S-metolachlor formulated as Dual® II Magnum.

Treatment requirements were calculated based upon the rates being tested, the concentration of active ingredient or acid equivalent in the formulation, and a 12 mL application volume at a rate of 187 L/ha.

For treatments comprised of formulated compounds, measured amounts of compounds were placed individually in 25 mL glass vials and diluted in a volume of 1.25% (v/v) Agri-Dex® crop oil concentrate (COC) to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of 10 mL of an aqueous mixture of 1.25% (v/v) COC so that the final spray solutions contained 1.25% (v/v) COC.

For treatments comprised of technical compounds, weighed amounts can be placed individually in 25 mL glass vials and dissolved in a volume of 97:3 (v/v) acetone/DMSO to obtain 12× stock solutions. If a test compound does not dissolve readily, the mixture can be warmed and/or sonicated. Application solutions can be prepared by adding an appropriate amount of each stock solution (e.g., 1 mL) and diluted to the appropriate final concentrations with the addition of 10 mL of an aqueous mixture of 1.5% (v/v) COC so that the final spray solutions contain 1.25% (v/v) COC. When technical materials are used, the concentrated stock solutions can be added to the spray solutions so that the final acetone and DMSO concentrations of the application solutions are 16.2% and 0.5%, respectively.

For treatments comprised of formulated and technical compounds, weighed amounts of the technical materials were placed individually in 25 mL glass vials and dissolved in a volume of 97:3 (v/v) acetone/DMSO to obtain 12× stock solutions, and measured amounts of the formulated compounds were placed individually in 25 mL glass vials and diluted in a volume of 1.5% (v/v) COC or water to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of an appropriate amount of an aqueous mixture of 1.5% (v/v) COC so that the final spray solutions contained 1.25% (v/v) COC. As required, additional water and/or 97:3 (v/v) acetone/DMSO was added to individual application solutions so that the final acetone and DMSO concentrations of the application solutions being compared were 8.1% and 0.25%, respectively.

All stock solutions and applications solutions were visually inspected for compound compatibility prior to application. Spray solutions were applied to the soil with an overhead Mandel track sprayer equipped with a 8002E nozzles calibrated to deliver 187 L/ha over an application area of 0.503 $m^2$ at a spray height of 18 inches (46 cm) above average pot height. Control pots were sprayed in the same manner with the solvent blank.

The treated and control pots were placed in a greenhouse and top watered as needed. When required to ensure good germination and healthy plants, a fungicide treatment and/or other chemical or physical treatment was applied. The pots were maintained in a greenhouse with an approximate 14 hr photoperiod which was maintained at about 29° C. during the day and 26° C. during the night. Nutrients (Peters® Excel 15-5-15 5-Ca 2-Mg) were applied in the irrigation solution as needed and water was added on a regular basis. Supplemental lighting was provided with overhead metal halide 1000-Watt lamps as necessary. After approximately 4 weeks, the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

Expected=$A+B-(A \times B/100)$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Tables 51-53.

TABLE 51

Synergistic Activity of Soil-applied, Pre-emergence Applications of Compound A Benzyl Ester and Alachlor Herbicidal Compositions on Weed Control

| Compound A Benzyl Ester | Alachlor | Visual Weed Control (%) - 27 DAA IPOHE | |
|---|---|---|---|
| gae/ha | gai/ha | Obs | Exp |
| 32 | 0 | 28 | — |
| 0 | 1240 | 5 | — |
| 0 | 2480 | 13 | — |
| 32 | 1240 | 35 | 31 |
| 32 | 2480 | 55 | 37 |

TABLE 52

Synergistic Activity of Soil-applied, Pre-emergence Applications of Compound A Benzyl Ester and Dimethenamid-P Herbicidal Compositions on Weed Control

| Compound A Benzyl Ester | Dimethenamid-P | Visual Weed Control (%) - 29 DAA XANST | |
|---|---|---|---|
| gae/ha | gai/ha | Obs | Exp |
| 32 | 0 | 5 | — |
| 0 | 410 | 23 | — |
| 0 | 820 | 30 | — |
| 0 | 1640 | 50 | — |
| 32 | 410 | 48 | 26 |
| 32 | 820 | 43 | 34 |
| 32 | 1640 | 68 | 53 |

TABLE 53

Synergistic Activity of Soil-applied, Pre-emergence Applications of Compound A Benzyl Ester and S-Metolachlor Herbicidal Compositions on Weed Control

| Compound A Benzyl Ester | S-metolachlor | Visual Weed Control (%) - 28 DAA IPOHE | |
|---|---|---|---|
| gae/ha | gai/ha | Obs | Exp |
| 16 | 0 | 13 | — |
| 32 | 0 | 23 | — |
| 0 | 387.5 | 25 | — |

TABLE 53-continued

Synergistic Activity of Soil-applied, Pre-emergence Applications of Compound A Benzyl Ester and S-Metolachlor Herbicidal Compositions on Weed Control

| | | | |
|---|---|---|---|
| 0 | 775 | 0 | — |
| 0 | 1550 | 33 | — |
| 16 | 387.5 | 48 | 34 |
| 32 | 387.5 | 53 | 42 |
| 16 | 775 | 45 | 13 |
| 32 | 775 | 38 | 23 |
| 16 | 1550 | 65 | 41 |
| 32 | 1550 | 53 | 48 |

| IPOHE | *Ipomoea hederacea* (L.) Jacq. | morningglory, ivyleaf |
| XANST | *Xanthium strumarium* L. | cocklebur, common | gae/ha = grams acid equivalent per hectare
gai/ha = grams active ingredient per hectare
Obs = observed value
Exp = expected value as calculated by Colby's equation
DAA = days after application Example V Evaluation of Herbicidal Activity of Mixtures Applied Under Field Conditions to Transplanted Rice Post and pre-emergence field trials were conducted in Niigata, Japan. Trial sites were located in commercially grown fields of transplanted rice (*Oryza sativa*, variety: Koshihikari) using standard herbicide small plot research methodology. The trial plot size was 2 meters (m)×2 m with 3 replications. The nursery plants were grown in the greenhouse using practical methods and transplanted into the field at the 2.5-leaf stage on May 7, 2012. The row and in-row spaces were 30 cm and 17 cm, respectively. The crop was grown using normal cultural practices for fertilization, water management and maintenance to ensure good growth of the crop and the weeds.

Treatments consisted of the benzyl ester of 4-amino-3-chloro-5-fluoro-6-(4-chloro-2-fluoro-3-methoxyphenyl) pyridine-2-carboxylic acid (Compound A) formulated as an SC (suspension concentrate) and various herbicidal components alone and in combination. Compound A benzyl ester was applied on an active ingredient basis. The herbicidal components were applied on an active ingredient basis and included very long chain fatty acid (VLCFA) synthesis-inhibiting and fatty acid/lipid biosynthesis herbicides pretilachlor formulated as a commercially available granular formulation and benfuresate formulated as a commercially available flowable formulation.

Compound A benzyl ester SC was once diluted in 100 mL water in the 200 mL bottle/plot to achieve the desired rates and applied by water injection. Water injection applications were made by hand as evenly as possible. Pretilachlor was applied by hand, and benfuresate was applied using a pipette to achieve the desired rates. Each compound in mixture treatments was applied separately and successively. Water depth was 3 cm at application. Treatments were rated at 25 and 40 days after application (DAA) for post and pre-emergence trials respectively as compared to the untreated control plants. Visual weed control was scored on a scale of 0 to 100 percent where 0 corresponds to no injury and 100 corresponds to complete kill.

All treatment results, both for the single product and mixtures, are an average of 3 replicates. The trial sites had naturally occurring populations of weeds. The weed spectrum included, but was not limited to, common barnyardgrass (*Echinochloa crus-galli*, ECHCG), *monochoria* (*Monochoria vaginalis*, MOOVA), Japanese bulrush (*Scirpus juncoides*, SCPJU), kuroguwai (*Eleocharis kuroguwai*, ELOKU), common falsepimpernel (*Lindernia pyxidaria*, LIDPY), Souchet tardif (*Cyperus serotinus*, CYPSE), smallflower flatsedge (*Cyperus difformis*, CYPDI), American waterwort (*Elatine triandra*, ELTTR), and swamp smartweed (*Polygonum hydropiperoides*, POLHP).

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

Expected=$A+B-(A \times B/100)$

A=observed efficacy of active ingredient A at the same concentration as used in the mixture.

B=observed efficacy of active ingredient B at the same concentration as used in the mixture.

Some of the compounds tested, application rates employed, plant species tested, and results for submerged (weeds have not yet emerged from the flood water) weed control are given in Table 54.

Some of the compounds tested, application rates employed, plant species tested, and results for early postemergence weed control are given in Tables 55-56.

TABLE 54

Synergistic Activity of In-Water Applied Compound A Benzyl Ester and Benfuresate Herbicidal Compositions on Submerged Weed Control in a Transplanted Rice Cropping System when Evaluated 31 DAA (Days After Application) in Japan.

| Compound A | | Visual Weed Control (%) - 31 DAA | | | |
|---|---|---|---|---|---|
| Benzyl Ester | Benfuresate | SCPJU | | POLHP | |
| gai/ha | gai/ha | Obs | Exp | Obs | Exp |
| 100 | 0 | 87.7 | — | 68.3 | — |
| 0 | 600 | 64.3 | — | 94.3 | — |
| 100 | 600 | 99.7 | 95.6 | 100.0 | 98.2 |

TABLE 55

Synergistic Activity of In-Water Applied Compound A Benzyl Ester and Benfuresate Herbicidal Compositions on Early Post-emergence Weed Control in a Transplanted Rice Cropping System when Evaluated 11-16 DAA (Days After Application) in Japan.

| Compound A | | Visual Weed Control (%) - 11 & 16 DAA | | | |
|---|---|---|---|---|---|
| Benzyl Ester | Benfuresate | ECHCG (11 DAA) | | ECHCG (16 DAA) | |
| gai/ha | gai/ha | Obs | Exp | Obs | Exp |
| 100 | 0 | 3.3 | — | 20.0 | — |
| 0 | 600 | 6.7 | — | 20.0 | — |
| 100 | 600 | 82.3 | 9.8 | 89.3 | 36.0 |

TABLE 56

Synergistic Activity of In-Water Applied Compound A Benzyl Ester and Pretilachlor Herbicidal Compositions on Early Post-emergence Weed Control in a Transplanted Rice Cropping System when Evaluated 11 DAA (Days After Application) in Japan.

| Compound A Benzyl Ester | Pretilachlor | Visual Weed Control (%) - 11 DAA ECHCG | |
|---|---|---|---|
| gai/ha | gai/ha | Obs | Exp |
| 100 | 0 | 6.7 | — |
| 0 | 400 | 46.7 | — |
| 100 | 400 | 89.3 | 50.3 |

| | | |
|---|---|---|
| ECHCG | *Echinochloa crusgalli* (L.) Beauv. | barnyardgrass |
| POLHP | *Polygonum hydropiperoides* Michx. | smartweed, swamp |
| SCPJU | *Schoenoplectus juncoides* (Roxb.) Palla | bulrush, Japanese | gai/ha = grams active ingredient per hectare
Obs = observed value
Exp = expected value as calculated by Colby's equation
DAA = days after application

What is claimed is:

1. A herbicidal composition comprising a herbicidally effective amount of (a) a compound of the formula (I)

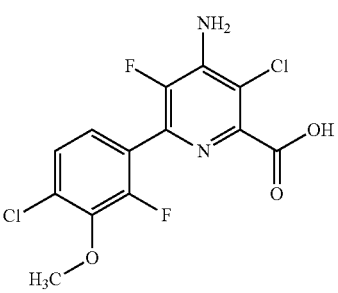

(I)

or $C_{1-4}$ alkyl or benzyl ester thereof and (b) at least one herbicide, wherein the at least one herbicide inhibits very long chain fatty acid and fatty acid synthesis, wherein (b) is selected from the group consisting of: acetochlor, alachlor, anilofos, benfuresate, cafenstrole, dimethenamid-P, fentrazamide, indanofan, flufenacet, mefenacet, s-metolachlor, molinate, pethoxamid, pretilachlor, prosulfocarb, pyroxasulfone, thenylchlor, butachlor, and thiobencarb, or an agriculturally acceptable salt thereof, wherein (a) and (b) are present in the composition in a ratio such that the composition exhibits herbicidal synergy, and wherein the ratio between (a):(b) is from about 1:1 to about 1:800.

2. The composition of claim 1, wherein (a) is a $C_{1-4}$ alkyl ester of compound (I).

3. The composition of claim 1, wherein (a) is a benzyl ester of compound (I).

4. The composition of claim 1, wherein (a) is the compound of formula (I), which is the carboxylic acid.

5. The composition of claim 1, further comprising at least one compound selected from the group consisting of agriculturally acceptable herbicide safeners, adjuvants, and carriers.

6. The composition according to claim 1, wherein the ratio between (a):(b) is selected from the group consisting of: from about 1:46 to about 1:3 when (b) is acetochlor; from about 1:78 to about 1:39 when (b) is alachlor; from about 1:50 to about 1:3 when (b) is anilofos; from about 1:57 to about 1:2 when (b) is benfuresate; from about 1:24 to about 1:2 when (b) is cafenstrole; from about 1:51 to about 1:9 when (b) is dimethenamid-P; from about 1:19 to about 1:1 when (b) is fentrazamide; from about 1:19 to about 1:2 when (b) is indanofan; from about 1:94 to about 1:12 when (b) is flufenacet; from about 1:150 to about 1:2 when (b) is mefenacet; from about 1:97 to about 1:12 when (b) is s-metolachlor; from about 1:350 to about 1:44 when (b) is molinate; from about 1:153 to about 1:38 when (b) is pethoxamid; from about 1:34 to about 1:2 when (b) is pretilachlor; from about 1:800 to about 1:200 when (b) is prosulfocarb; from about 1:15 to about 1:4 when (b) is pyroxasulfone; from about 1:34 to about 1:4 when (b) is thenylchlor; from about 1:6 to about 1:103 when (b) is butachlor, and from about 1:511 to about 1:32 when (b) is thiobencarb, and wherein any aforementioned compound for (b) may be an agriculturally acceptable salt thereof.

7. The composition of claim 1, wherein (b) is selected from the group consisting of: acetochlor, alachlor, anilofos, benfuresate, cafenstrole, dimethenamid-P, fentrazamide, indanofan, flufenacet, mefenacet, s-metolachlor, molinate, pethoxamid, pretilachlor, prosulfocarb, pyroxasulfone, thenylchlor, and thiobencarb, or an agriculturally acceptable salt thereof.

8. A method of controlling undesirable vegetation, comprising the steps of: contacting a plant, wherein the plant is undesirable vegetation, or the locus thereof, soil or water, wherein the soil or the water allows for the growth of the undesirable vegetation, with a herbicidally effective amount of a combination comprising (a) a compound of the formula (I):

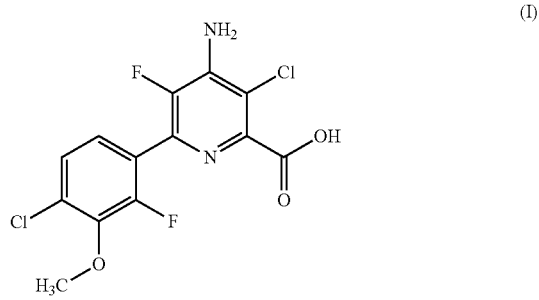 [SMILES: COc1c(Cl)ccc(-c2nc(C(=O)O)c(Cl)c(N)c2F)c1F]

or $C_{1-4}$ alkyl or benzyl ester thereof and (b) at least one herbicide, wherein the at least one herbicide inhibits very long chain fatty acid and fatty acid synthesis, wherein (b) is selected from the group consisting of: acetochlor, alachlor, anilofos, benfuresate, cafenstrole, dimethenamid-P, fentrazamide, indanofan, flufenacet, mefenacet, s-metolachlor, molinate, pethoxamid, pretilachlor, prosulfocarb, pyroxasulfone, thenylchlor, butachlor, and thiobencarb, or an agriculturally acceptable salt thereof, wherein (a) and (b) are present in the composition in a ratio such that the composition exhibits herbicidal synergy, and wherein the ratio between (a):(b) is from about 1:1 to about 1:800.

9. The method of claim 8, wherein the undesirable vegetation is controlled in direct-seeded, water-seeded and transplanted rice, cereals, wheat, barley, oats, rye, sorghum, corn/maize, sugarcane, sunflower, rapeseed, canola, sugar beet, soybean, cotton, pineapple, pastures, grasslands, rangelands, fallowland, turf, tree and vine orchards, aquatics, industrial vegetation management (IVM) or rights of way (ROW).

10. The method of claim 8, wherein the (a) and (b) are applied to water.

11. The method of claim 10 wherein the water is part of a flooded rice paddy.

12. The method of claim 8, wherein the (a) and (b) are applied pre-emergently to undesirable vegetation.

13. The method of claim 8, wherein the (a) and (b) are applied post-emergently to undesirable vegetation.

14. The method of claim 8, wherein the undesirable vegetation is controlled in glyphosate-, 5-enolpyruvylshikimate-3-phosphate synthase inhibitor-, glufosinate-, glutamine synthetase inhibitor-, dicamba-, phenoxy auxin-, pyridyloxy auxin-, synthetic auxin-, auxin transport inhibitor-, aryloxyphenoxypropionate-, cyclohexanedione-, phenylpyrazoline-, acetyl CoA carboxylase inhibitor-, imidazolinone-, sulfonylurea-, pyrimidinylthiobenzoate-, triazolopyrimidine-, sulfonylaminocarbonyltriazolinone-, acetolactate synthase or acetohydroxy acid synthase inhibitors-, 4-hydroxyphenyl-pyruvate dioxygenase inhibitor-, phytoene desaturase inhibitor-, carotenoid biosynthesis inhibitor-, protoporphyrinogen oxidase inhibitor-, cellulose biosynthesis inhibitor-, mitosis inhibitor-, microtubule inhibitor-, very long chain fatty acid inhibitor-, fatty acid and lipid biosynthesis inhibitor-, photosystem I inhibitor-, photosystem II inhibitor-, triazine-, or bromoxynil-tolerant crops.

15. The method of claim 13, wherein the undesirable vegetation possesses multiple or stacked traits conferring tolerance to multiple herbicides or herbicides that exhibit multiple modes of action.

16. The method of claim 8, wherein the undesirable vegetation comprises a herbicide resistant or tolerant weed.

17. The method of claim 15, wherein the undesirable vegetation is a biotype with resistance or tolerance to multiple herbicides, multiple chemical classes, multiple herbicide modes-of-action or via multiple resistance mechanisms.

18. The method of claim 15, wherein the undesirable vegetation is a biotype resistant or tolerant to acetolactate synthase or acetohydroxy acid synthase inhibitors, photosystem II inhibitors, acetyl CoA carboxylase inhibitors, synthetic auxins, auxin transport inhibitors, photosystem I inhibitors, 5-enolpyruvylshikimate-3-phosphate synthase inhibitors, microtubule assembly inhibitors, fatty acid and lipid synthesis inhibitors, protoporphyrinogen oxidase inhibitors, carotenoid biosynthesis inhibitors, very long chain fatty acid inhibitors, phytoene desaturase inhibitors, glutamine synthetase inhibitors, 4-hydroxyphenyl-pyruvate-dioxygenase inhibitors, mitosis inhibitors, cellulose biosynthesis inhibitors, herbicides with multiple modes-of-action, quinclorac, arylaminopropionic acids, difenzoquat, endothall, or organoarsenicals.

19. The method according to claim 8, wherein the ratio between (a):(b) is selected from the group consisting of: from about 1:46 to about 1:3 when (b) is acetochlor; from about 1:78 to about 1:39 when (b) is alachlor; from about 1:50 to about 1:3 when (b) is anilofos; from about 1:57 to about 1:2 when (b) is benfuresate; from about 1:24 to about 1:2 when (b) is cafenstrole; from about 1:51 to about 1:9 when (b) is dimethenamid-P; from about 1:19 to about 1:1 when (b) is fentrazamide; from about 1:19 to about 1:2 when (b) is indanofan; from about 1:94 to about 1:12 when (b) is flufenacet; from about 1:150 to about 1:2 when (b) is mefenacet; from about 1:97 to about 1:12 when (b) is s-metolachlor; from about 1:350 to about 1:44 when (b) is molinate; from about 1:153 to about 1:38 when (b) is pethoxamid; from about 1:34 to about 1:2 when (b) is pretilachlor; from about 1:800 to about 1:200 when (b) is prosulfocarb; from about 1:15 to about 1:4 when (b) is pyroxasulfone; from about 1:34 to about 1:4 when (b) is thenylchlor; from about 1:6 to about 1:103 when (b) is butachlor, and from about 1:511 to about 1:32 when (b) is thiobencarb, and wherein any aforementioned compound for (b) may be an agriculturally acceptable salt thereof.

20. The method according to claim 8, wherein (b) is selected from the group consisting of: acetochlor, alachlor, anilofos, benfuresate, cafenstrole, dimethenamid-P, fentrazamide, indanofan, flufenacet, mefenacet, s-metolachlor, molinate, pethoxamid, pretilachlor, prosulfocarb, pyroxasulfone, thenylchlor, and thiobencarb, or an agriculturally acceptable salt thereof.

* * * * *